United States Patent
Verploegen et al.

(10) Patent No.: US 9,540,433 B2
(45) Date of Patent: Jan. 10, 2017

(54) HUMAN ANTIBODIES AND ANTIBODY-DRUG CONJUGATES AGAINST CD74

(75) Inventors: Sandra Verploegen, Nieuwegein (NL); Marije Overdijk, Utrecht (NL); Riemke Van Dijkhuizen, Zeist (NL); Willem Karel Bleeker, Amsterdam (NL); Patrick Van Berkel, Utrecht (NL); Paul Parren, Odijk (NL); Steen Lisby, Frederiksberg (DK)

(73) Assignee: GENMAB A/S, Copenhagen (DK)

( * ) Notice: Subject to any disclaimer, the term of this patent is extended or adjusted under 35 U.S.C. 154(b) by 260 days.

(21) Appl. No.: 13/982,959

(22) PCT Filed: Feb. 1, 2012

(86) PCT No.: PCT/EP2012/051679
§ 371 (c)(1),
(2), (4) Date: Oct. 7, 2013

(87) PCT Pub. No.: WO2012/104344
PCT Pub. Date: Aug. 9, 2012

(65) Prior Publication Data
US 2014/0030273 A1 Jan. 30, 2014

Related U.S. Application Data

(60) Provisional application No. 61/438,383, filed on Feb. 1, 2011.

(30) Foreign Application Priority Data

Feb. 1, 2011 (DK) .................... 2011 00064

(51) Int. Cl.
| | |
|---|---|
| A61K 39/395 | (2006.01) |
| C07K 16/28 | (2006.01) |
| C07K 16/30 | (2006.01) |
| C07K 16/42 | (2006.01) |
| C07K 16/18 | (2006.01) |
| A61K 47/48 | (2006.01) |
| A61K 51/10 | (2006.01) |
| A61K 31/7088 | (2006.01) |
| A61K 35/17 | (2015.01) |
| A61K 35/76 | (2015.01) |
| A61K 38/16 | (2006.01) |
| A61K 38/19 | (2006.01) |
| A61K 45/06 | (2006.01) |
| A61K 39/00 | (2006.01) |

(52) U.S. Cl.
CPC .......... *C07K 16/18* (2013.01); *A61K 31/7088* (2013.01); *A61K 35/17* (2013.01); *A61K 35/76* (2013.01); *A61K 38/162* (2013.01); *A61K 38/19* (2013.01); *A61K 39/39533* (2013.01); *A61K 45/06* (2013.01); *A61K 47/48561* (2013.01); *A61K 51/1027* (2013.01); *C07K 16/2833* (2013.01); *A61K 2039/505* (2013.01); *C07K 2317/21* (2013.01); *C07K 2317/33* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,772,373 B2 | 8/2010 | Hansen et al. | |
| 2005/0226876 A1* | 10/2005 | Graus | C07K 16/2854 424/144.1 |
| 2006/0193865 A1* | 8/2006 | Govindan | 424/155.1 |

FOREIGN PATENT DOCUMENTS

| | | |
|---|---|---|
| WO | 03/074567 A2 | 9/2003 |
| WO | 2004/054622 A1 | 7/2004 |
| WO | 2007112193 A2 | 10/2007 |
| WO | 2007/140371 A2 | 12/2007 |

OTHER PUBLICATIONS

MacCallum et al. (Journal of Molecular. Biology, 1996, vol. 262, pp. 732-745).*
Pascalis et al (Journal of Immunology, 2002, vol. 169, pp. 3076-3084).*
Casset et al (Biochemical and Biophysical Research Communications, 2003, vol. 307, pp. 198-205).*
Rudikoff et al (Proc Natl Acad Sci USA 1982 vol. 79 p. 1979).*
Zeimet and Marth (The Lancet Oncology, 2003, vol. 4, pp. 415-422).*
Robinson (PLoS Biology, 2004, vol. 1, pp. 0018-0020).*
Iyer et al (Journal of Clinical Investigation, 1998, vol. 101, pp. 847-854).*
Stein et al (Blood, 2004, vol. 104, pp. 3705-3711).*
Okeley, N. et al, "Intracellular Activation of SGN-35, a Potent Anti-CD30 Antibody Drug Conjugate," Clin. Cancer Res., 16(3):888-897 (2010).
Borghese et al., "CD74: an emerging opportunity as a therapeutic target in cancer and autoimmune disease," Expert Opin. Ther. Targets 15(3):237-251 (2011).
Chang CH et al., "Effective therapy of human lymphoma xenografts with a novel recombinant ribonuclease/anti-CD74 humanized IgG4 antibody immunotoxin," Blood, 106(13):4308-4314 (2005).
Gupta P. et al., "Dual-targeting immunotherapy of lymphoma: potent cytotoxicity of anti-CD20/CD74 bispecific antibodies in mantle cell and other lymphomas," Blood 119(16):3767-3778 (2012).

(Continued)

*Primary Examiner* — Karen Canella
(74) *Attorney, Agent, or Firm* — Nelson Mullins Riley & Scarborough LLP; Jane E. Remillard, Esq.; Christopher L. Frank

(57) ABSTRACT

Isolated human monoclonal antibodies which bind to human CD74 and related antibody-drug conjugates are disclosed. Pharmaceutical compositions comprising the antibodies or antibody-drug conjugates, and therapeutic and diagnostic methods for using the antibodies and/or antibody-drug conjugates, are also disclosed.

43 Claims, 13 Drawing Sheets

(56) References Cited

OTHER PUBLICATIONS

Mark T. et al., "Milatuzumab: a promising new agent for the treatment of lymphoid malignancies," 18(1):99-104 (2009).
Sapra P. et al., "Anti-CD74 antibody-doxorubicin conjugate, IMMU-110, in a human multiple myeloma xenograft and in monkeys," Clin. Cancer Res. 11(14):5257-5264 (2005).
Younes A. et a., "Brentuximab vedotin (SGN-35) for relapsed CD30-positive lymphomas," N. Engl. J. Med. 363 (19):1812-1821 (2010).

* cited by examiner

Figure 1A  CD74v1 (296 aa; SEQ ID NO:1)

```
  1 mhrrrsrscr edqkpvmddq rdlisnneql pmlgrrpgap eskcsrgaly
 51 tgfsilvtll lagqattayf lyqqqgrldk ltvtsqnlql enlrmklpkp
101 pkpvskmrma tpllmqalpm galpqgpmqn atkygnmted hvmhllqnad
151 plkvypplkg sfpenlrhlk ntmetidwkv feswmhhwll femsrhsleq
201 kptdappkvl tkcqeevshi pavhpgsfrp kcdengnylp lqcygsigyc
251 wcvfpngtev pntrsrghhn cseslelepd ssglgvtkqd lgpvpm
```

Figure 1B  CD74v2 (232 aa; SEQ ID NO:2))

```
  1 mhrrrsrscr edqkpvmddq rdlisnneql pmlgrrpgap eskcsrgaly
 51 tgfsilvtll lagqattayf lyqqqgrldk ltvtsqnlql enlrmklpkp
101 pkpvskmrma tpllmqalpm galpqgpmqn atkygnmted hvmhllqnad
151 plkvypplkg sfpenlrhlk ntmetidwkv feswmhhwll femsrhsleq
201 kptdappkes leledpssgl gvtkqdlgpv pm
```

Figure 1C  CD74v1del2-36 (261 aa; SEQ ID NO:3)

```
  1 mpgapeskcs rgalytgfsi lvtlllagqa ttayflyqqq grldkltvts
 51 qnlqlenlrm klpkppkpvs kmrmatpllm qalpmgalpq gpmqnatkyg
101 nmtedhvmhl lqnadplkvy pplkgsfpen lrhlkntmet idwkvfeswm
151 hhwllfemsr hsleqkptda ppkvltkcqe evshipavhp gsfrpkcden
201 gnylplqcyg sigycwcvfp ngtevpntrs rghhncsesl eledpssglg
251 vtkqdlgpvp m
```

Figure 1D  CD74v2del2-36 (197 aa; SEQ D NO:4)

```
  1 mpgapeskcs rgalytgfsi lvtlllagqa ttayflyqqq grldkltvts
 51 qnlqlenlrm klpkppkpvs kmrmatpllm qalpmgalpq gpmqnatkyg
101 nmtedhvmhl lqnadplkvy pplkgsfpen lrhlkntmet idwkvfeswm
151 hhwllfemsr hsleqkptda ppkesleled pssglgvtkq dlgpvpm
```

Figure 1E  HisCD74v1 (230 aa; SEQ ID NO:5)

```
  1 hhhhhhqqqg rldkltvtsq nlqlenlrmk lpkppkpvsk mrmatpllmq
 51 alpmgalpqg pmqnatkygn mtedhvmhll qnadplkvyp plkgsfpenl
101 rhlkntmeti dwkvfeswmh hwllfemsrh sleqkptdap pkvltkcqee
151 vshipavhpg sfrpkcdeng nylplqcygs igycwcvfpn gtevpntrsr
201 ghhncsesle ledpssglgv tkqdlgpvpm
```

Figure 1F  HisCD74v2 (166 aa; SEQ ID NO:6)

```
  1 hhhhhhqqqg rldkltvtsq nlqlenlrmk lpkppkpvsk mrmatpllmq
 51 alpmgalpqg pmqnatkygn mtedhvmhll qnadplkvyp plkgsfpenl
101 rhlkntmeti dwkvfeswmh hwllfemsrh sleqkptdap pkesleledp
151 ssglgvtkqd lgpvpm
```

Figure 2A $V_H$:

```
                    |---CDR1---|                         |---CDR2----|                                                           |------CDR3-------|
QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCASGRXYGSGXYSSXFDIWGQGTLVTVSS VH2013-005 (7)
QVQLVESGGGVVQPGRSLRLSCAASGFTFSSYAMHWVRQAPGKGLEWVAVSYDGSNKYYADSVKGRFTISRDNSKNTLYLQMNSLRAEDTAVFYCARGRETTSQRTVILDYWGQGTLVTVTS VH2013-006 (11)
QVQLVESGGGVVQPGRSLRLSCAASGFTFSSYAMHWVRQAPGKGLEWVAVSYDGSNKYYADSVKGRFTISRDNSKNTLYLQMNSLRAEDTAVYYCARGRETTSQRIVILDYWGQGTLVTVSS VH2013-008 (15)
QVQLVESGGGVVQPGRSLRLSCAASGFTFSSYKMHWVRQAPDKGLEWVAVWRDSNKYYADSVKGRFTISRDNSKNTLYLQMNSLRAEDTAVYYCARGELYFG-AMYGIEWWGQGTTVTVSS VH2013-011 (19)
```

Figure 2B $V_L$:

```
                 |---CDR1---|                                      CDR2                                           |----CDR3----|
DIQMTQSPSSLSASVGDRVTITCRASQGIGSMLAWFQQKPEKAPKSLIYAASSLQSGVPSRFSGSGSGTDFTLTISSLQPEDFATYYCQQYNSYPLTFGGGTKVEIK VL2013-005 (23)
DIQMTQSPSSLSASVGDRVTITCRASQGISSMLAWYQQKPEKAPKSLIYAASSLQSGVPSRFSGSGSGTDFTLTISSLQPEDFATYYCQQYNSYPIHFGGGTKVEIK VL2013-006 (26)
DIQMTQSPSSLSASVGDRVTITCRASQGISSMLAWYQQKPEKAPKSLIYAASSLQSGVPSRFSGSGSGTDFTLTISSLQPEDFATYYCQQTNSYPLTFGGGTKVEIK VL2013-008 (26)
DIQMTQSPSSLSASVGDRVTITCRASQGISSMLAWYQQKPEKAPKSLIYAASSLQSGVPSRFSGSGSGTDFTLTISSLQPEDFATYYCQQYNSYPLTFGGGTKVEIK VL2013-011 (26)
```

○ HuMab-CD74-005
■ HuMab-CD74-005-vcMMAE
◉ HuMab-CD74-005-mcMMAF
□ HuMab-CD74-006
■ HuMab-CD74-006-vcMMAE
▣ HuMab-CD74-006-mcMMAF

△ HuMab-CD74-011
▲ HuMab-CD74-011-vcMMAE
▲ HuMab-CD74-011-mcMMAF
▽ IgG1-b12
▼ IgG1-b12-vcMMAE
▼ IgG1-b12-mcMMAF

SEQUENCE LISTING

<160> NUMBER OF SEQ ID NOS: 27

<210> SEQ ID NO 1
<211> LENGTH: 296
<212> TYPE: PRT
<213> ORGANISM: Artificial Sequence
<220> FEATURE:
<223> OTHER INFORMATION: Synthetic partial sequence

<400> SEQUENCE: 1

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

```
Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Val Leu Thr Lys Cys Gln Glu Val Ser His Ile Pro Ala Val His
    210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Asp Pro Ser Ser Gly Leu Gly Val Thr Lys
        275                 280                 285

Gln Asp Leu Gly Pro Val Pro Met
    290                 295

<210> SEQ ID NO 2
<211> LENGTH: 232
<212> TYPE: PRT
<213> ORGANISM: Artificial sequence
<220> FEATURE:
<223> OTHER INFORMATION: Synthetic partial sequence

<400> SEQUENCE: 2

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205
```

Glu Ser Leu Glu Leu Glu Asp Pro Ser Ser Gly Leu Gly Val Thr Lys
    210                 215                 220

Gln Asp Leu Gly Pro Val Pro Met
225                 230

<210> SEQ ID NO 3
<211> LENGTH: 261
<212> TYPE: PRT
<213> ORGANISM: Artificial sequence
<220> FEATURE:
<223> OTHER INFORMATION: Synthetic partial sequence

<400> SEQUENCE: 3

Met Pro Gly Ala Pro Glu Ser Lys Cys Ser Arg Gly Ala Leu Tyr Thr
1               5                   10                  15

Gly Phe Ser Ile Leu Val Thr Leu Leu Leu Ala Gly Gln Ala Thr Thr
            20                  25                  30

Ala Tyr Phe Leu Tyr Gln Gln Gln Gly Arg Leu Asp Lys Leu Thr Val
        35                  40                  45

Thr Ser Gln Asn Leu Gln Leu Glu Asn Leu Arg Met Lys Leu Pro Lys
    50                  55                  60

Pro Pro Lys Pro Val Ser Lys Met Arg Met Ala Thr Pro Leu Leu Met
65                  70                  75                  80

Gln Ala Leu Pro Met Gly Ala Leu Pro Gln Gly Pro Met Gln Asn Ala
                85                  90                  95

Thr Lys Tyr Gly Asn Met Thr Glu Asp His Val Met His Leu Leu Gln
            100                 105                 110

Asn Ala Asp Pro Leu Lys Val Tyr Pro Pro Leu Lys Gly Ser Phe Pro
        115                 120                 125

Glu Asn Leu Arg His Leu Lys Asn Thr Met Glu Thr Ile Asp Trp Lys
    130                 135                 140

Val Phe Glu Ser Trp Met His Trp Leu Leu Phe Glu Met Ser Arg
145                 150                 155                 160

His Ser Leu Glu Gln Lys Pro Thr Asp Ala Pro Pro Lys Val Leu Thr
                165                 170                 175

Lys Cys Gln Glu Glu Val Ser His Ile Pro Ala Val His Pro Gly Ser
            180                 185                 190

Phe Arg Pro Lys Cys Asp Glu Asn Gly Asn Tyr Leu Pro Leu Gln Cys
        195                 200                 205

Tyr Gly Ser Ile Gly Tyr Cys Trp Cys Val Phe Pro Asn Gly Thr Glu
    210                 215                 220

Val Pro Asn Thr Arg Ser Arg Gly His His Asn Cys Ser Glu Ser Leu
225                 230                 235                 240

Glu Leu Glu Asp Pro Ser Ser Gly Leu Gly Val Thr Lys Gln Asp Leu
                245                 250                 255

Gly Pro Val Pro Met
            260

<210> SEQ ID NO 4
<211> LENGTH: 197
<212> TYPE: PRT
<213> ORGANISM: Artificial sequence
<220> FEATURE:
<223> OTHER INFORMATION: Synthetic partial sequence

<400> SEQUENCE: 4

Met Pro Gly Ala Pro Glu Ser Lys Cys Ser Arg Gly Ala Leu Tyr Thr
1               5                   10                  15

Gly Phe Ser Ile Leu Val Thr Leu Leu Leu Ala Gly Gln Ala Thr Thr
            20                  25                  30

Ala Tyr Phe Leu Tyr Gln Gln Gln Gly Arg Leu Asp Lys Leu Thr Val
        35                  40                  45

Thr Ser Gln Asn Leu Gln Leu Glu Asn Leu Arg Met Lys Leu Pro Lys
50                  55                  60

Pro Pro Lys Pro Val Ser Lys Met Arg Met Ala Thr Pro Leu Leu Met
65                  70                  75                  80

Gln Ala Leu Pro Met Gly Ala Leu Pro Gln Gly Pro Met Gln Asn Ala
                85                  90                  95

Thr Lys Tyr Gly Asn Met Thr Glu Asp His Val Met His Leu Leu Gln
            100                 105                 110

Asn Ala Asp Pro Leu Lys Val Tyr Pro Pro Leu Lys Gly Ser Phe Pro
        115                 120                 125

Glu Asn Leu Arg His Leu Lys Asn Thr Met Glu Thr Ile Asp Trp Lys
130                 135                 140

Val Phe Glu Ser Trp Met His His Trp Leu Leu Phe Glu Met Ser Arg
145                 150                 155                 160

His Ser Leu Glu Gln Lys Pro Thr Asp Ala Pro Pro Lys Glu Ser Leu
                165                 170                 175

Glu Leu Glu Asp Pro Ser Ser Gly Leu Gly Val Thr Lys Gln Asp Leu
            180                 185                 190

Gly Pro Val Pro Met
            195

<210> SEQ ID NO 5
<211> LENGTH: 230
<212> TYPE: PRT
<213> ORGANISM: Artificial sequence
<220> FEATURE:
<223> OTHER INFORMATION: Synthetic partial sequence with His-tag

<400> SEQUENCE: 5

His His His His His His Gln Gln Gln Gly Arg Leu Asp Lys Leu Thr
1               5                   10                  15

Val Thr Ser Gln Asn Leu Gln Leu Glu Asn Leu Arg Met Lys Leu Pro
            20                  25                  30

Lys Pro Pro Lys Pro Val Ser Lys Met Arg Met Ala Thr Pro Leu Leu
        35                  40                  45

Met Gln Ala Leu Pro Met Gly Ala Leu Pro Gln Gly Pro Met Gln Asn
50                  55                  60

Ala Thr Lys Tyr Gly Asn Met Thr Glu Asp His Val Met His Leu Leu
65                  70                  75                  80

Gln Asn Ala Asp Pro Leu Lys Val Tyr Pro Pro Leu Lys Gly Ser Phe
                85                  90                  95

Pro Glu Asn Leu Arg His Leu Lys Asn Thr Met Glu Thr Ile Asp Trp
            100                 105                 110

Lys Val Phe Glu Ser Trp Met His His Trp Leu Leu Phe Glu Met Ser
        115                 120                 125

Arg His Ser Leu Glu Gln Lys Pro Thr Asp Ala Pro Pro Lys Val Leu
130                 135                 140

Thr Lys Cys Gln Glu Glu Val Ser His Ile Pro Ala Val His Pro Gly
145                 150                 155                 160

Ser Phe Arg Pro Lys Cys Asp Glu Asn Gly Asn Tyr Leu Pro Leu Gln
                165                 170                 175

```
Cys Tyr Gly Ser Ile Gly Tyr Cys Trp Cys Val Phe Pro Asn Gly Thr
            180                 185                 190

Glu Val Pro Asn Thr Arg Ser Arg Gly His His Asn Cys Ser Glu Ser
        195                 200                 205

Leu Glu Leu Glu Asp Pro Ser Ser Gly Leu Gly Val Thr Lys Gln Asp
    210                 215                 220

Leu Gly Pro Val Pro Met
225                 230

<210> SEQ ID NO 6
<211> LENGTH: 166
<212> TYPE: PRT
<213> ORGANISM: Artificial sequence
<220> FEATURE:
<223> OTHER INFORMATION: Synthetic partial sequence with His-tag

<400> SEQUENCE: 6

His His His His His His Gln Gln Gln Gly Arg Leu Asp Lys Leu Thr
1               5                   10                  15

Val Thr Ser Gln Asn Leu Gln Leu Glu Asn Leu Arg Met Lys Leu Pro
            20                  25                  30

Lys Pro Pro Lys Pro Val Ser Lys Met Arg Met Ala Thr Pro Leu Leu
        35                  40                  45

Met Gln Ala Leu Pro Met Gly Ala Leu Pro Gln Gly Pro Met Gln Asn
    50                  55                  60

Ala Thr Lys Tyr Gly Asn Met Thr Glu Asp His Val Met His Leu Leu
65                  70                  75                  80

Gln Asn Ala Asp Pro Leu Lys Val Tyr Pro Pro Leu Lys Gly Ser Phe
                85                  90                  95

Pro Glu Asn Leu Arg His Leu Lys Asn Thr Met Glu Thr Ile Asp Trp
            100                 105                 110

Lys Val Phe Glu Ser Trp Met His His Trp Leu Leu Phe Glu Met Ser
        115                 120                 125

Arg His Ser Leu Glu Gln Lys Pro Thr Asp Ala Pro Pro Lys Glu Ser
    130                 135                 140

Leu Glu Leu Glu Asp Pro Ser Ser Gly Leu Gly Val Thr Lys Gln Asp
145                 150                 155                 160

Leu Gly Pro Val Pro Met
                165

<210> SEQ ID NO 7
<211> LENGTH: 124
<212> TYPE: PRT
<213> ORGANISM: Homo sapiens

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Ser Gly Arg Tyr Tyr Gly Ser Gly Ser Tyr Ser Ser Tyr Phe Asp
            100                 105                 110

Tyr Trp Gly Gln Gly Thr Leu Val Thr Val Ser Ser
        115                 120

<210> SEQ ID NO 8
<211> LENGTH: 8
<212> TYPE: PRT
<213> ORGANISM: Homo sapiens

<400> SEQUENCE: 8

Gly Phe Thr Phe Ser Ser Tyr Ala
1               5

<210> SEQ ID NO 9
<211> LENGTH: 8
<212> TYPE: PRT
<213> ORGANISM: Homo sapiens

<400> SEQUENCE: 9

Ile Ser Tyr Asp Gly Ser Asn Lys
1               5

<210> SEQ ID NO 10
<211> LENGTH: 17
<212> TYPE: PRT
<213> ORGANISM: Homo sapiens

<400> SEQUENCE: 10

Ala Ser Gly Arg Tyr Tyr Gly Ser Gly Ser Tyr Ser Ser Tyr Phe Asp
1               5                   10                  15

Tyr

<210> SEQ ID NO 11
<211> LENGTH: 124
<212> TYPE: PRT
<213> ORGANISM: Homo sapiens

<400> SEQUENCE: 11

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Phe Tyr Cys
                85                  90                  95

Ala Arg Gly Arg Glu Ile Thr Ser Gln Asn Ile Val Ile Leu Leu Asp
            100                 105                 110

Tyr Trp Gly Gln Gly Thr Leu Val Thr Val Thr Ser
        115                 120

<210> SEQ ID NO 12
<211> LENGTH: 8
```

```
<212> TYPE: PRT
<213> ORGANISM: Homo sapiens

<400> SEQUENCE: 12

Gly Phe Thr Phe Ser Ser Tyr Ala
1               5

<210> SEQ ID NO 13
<211> LENGTH: 8
<212> TYPE: PRT
<213> ORGANISM: Homo sapiens

<400> SEQUENCE: 13

Ile Ser Tyr Asp Gly Ser Ile Lys
1               5

<210> SEQ ID NO 14
<211> LENGTH: 17
<212> TYPE: PRT
<213> ORGANISM: Homo sapiens

<400> SEQUENCE: 14

Ala Arg Gly Arg Glu Ile Thr Ser Gln Asn Ile Val Ile Leu Leu Asp
1               5                   10                  15

Tyr

<210> SEQ ID NO 15
<211> LENGTH: 124
<212> TYPE: PRT
<213> ORGANISM: Homo sapiens

<400> SEQUENCE: 15

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Glu Ile Thr Ser Gln Asn Ile Val Ile Leu Leu Asp
            100                 105                 110

Tyr Trp Gly Gln Gly Thr Leu Val Thr Val Ser Ser
        115                 120

<210> SEQ ID NO 16
<211> LENGTH: 8
<212> TYPE: PRT
<213> ORGANISM: Homo sapiens

<400> SEQUENCE: 16

Gly Phe Thr Phe Ser Ser Tyr Ala
1               5

<210> SEQ ID NO 17
<211> LENGTH: 8
<212> TYPE: PRT
```

```
<213> ORGANISM: Homo sapiens

<400> SEQUENCE: 17

Ile Ser Tyr Asp Gly Ser Asn Lys
1               5

<210> SEQ ID NO 18
<211> LENGTH: 17
<212> TYPE: PRT
<213> ORGANISM: Homo sapiens

<400> SEQUENCE: 18

Ala Arg Gly Arg Glu Ile Thr Ser Gln Asn Ile Val Ile Leu Leu Asp
1               5                   10                  15

Tyr

<210> SEQ ID NO 19
<211> LENGTH: 123
<212> TYPE: PRT
<213> ORGANISM: Homo sapiens

<400> SEQUENCE: 19

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Thr Leu Val Arg Gly Ala Met Tyr Gly Thr Asp Val
            100                 105                 110

Trp Gly Gln Gly Thr Thr Val Thr Val Ser Ser
        115                 120

<210> SEQ ID NO 20
<211> LENGTH: 8
<212> TYPE: PRT
<213> ORGANISM: Homo sapiens

<400> SEQUENCE: 20

Gly Phe Thr Phe Ser Ser Tyr Gly
1               5

<210> SEQ ID NO 21
<211> LENGTH: 8
<212> TYPE: PRT
<213> ORGANISM: Homo sapiens

<400> SEQUENCE: 21

Ile Trp Tyr Asp Gly Ser Asn Lys
1               5

<210> SEQ ID NO 22
<211> LENGTH: 16
<212> TYPE: PRT
<213> ORGANISM: Homo sapiens
```

```
<400> SEQUENCE: 22

Ala Arg Gly Gly Thr Leu Val Arg Gly Ala Met Tyr Gly Thr Asp Val
1               5                   10                  15

<210> SEQ ID NO 23
<211> LENGTH: 107
<212> TYPE: PRT
<213> ORGANISM: Homo sapiens

<400> SEQUENCE: 23

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Phe Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 24
<211> LENGTH: 6
<212> TYPE: PRT
<213> ORGANISM: Homo sapiens

<400> SEQUENCE: 24

Gln Gly Ile Ser Ser Trp
1               5

<210> SEQ ID NO 25
<211> LENGTH: 9
<212> TYPE: PRT
<213> ORGANISM: Homo sapiens

<400> SEQUENCE: 25

Gln Gln Tyr Asn Ser Tyr Pro Leu Thr
1               5

<210> SEQ ID NO 26
<211> LENGTH: 107
<212> TYPE: PRT
<213> ORGANISM: Homo sapiens

<400> SEQUENCE: 26

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Ser Tyr Pro Leu
                85                  90                  95
Thr Phe Gly Gly Gly Thr Lys Val Glu Ile Lys
            100                 105

<210> SEQ ID NO 27
<211> LENGTH: 3
<212> TYPE: PRT
<213> ORGANISM: Homo sapiens

<400> SEQUENCE: 27

Ala Ala Ser
1
```

HUMAN ANTIBODIES AND ANTIBODY-DRUG CONJUGATES AGAINST CD74

RELATED APPLICATIONS

This application is a 35 U.S.C. 371 national stage filing of International Application No. PCT/EP2012/051679 filed Feb. 1, 2012, which claims priority to 61/438,383 filed Feb. 1, 2011; and PA 2011 00064 filed Feb. 1, 2011. The entire contents of the aforementioned applications are incorporated herein by reference.

FIELD OF THE INVENTION

The present invention relates to CD74-specific antibodies and antibody-drug conjugates (ADCs) thereof, pharmaceutical compositions of such antibodies or ADCs, and their use in therapeutic applications.

BACKGROUND OF THE INVENTION

Human leukocyte antigen (HLA) class II histocompatibility antigen gamma chain, also called HLA-DR antigen-associated invariant chain, Ia antigen-associated invariant chain, Ii and CD74, is a transmembrane protein with a short cytoplasmic tail. The primary function of CD74 is to regulate peptide loading onto the major histocompatibility complex (MHC) class II heterodimers in intracellular compartments.

Only a small portion of the total cell CD74 content is expressed on the cell surface. Cell surface CD74 is very rapidly internalized both with and without CD74 antibodies bound (Roche P A et al., PNAS 1993; 90: 8581-8585; Hansen H J et al., Biochem J 1996; 320: 293-300; Ong G L et al., Immunology 1999; 98:296-302). The steady-state level of cell surface CD74 is therefore rather low, varying in monocytes from a few hundred to a few thousand molecules per cell.

The exact function of cell surface-expressed CD74 is not known, but studies have documented CD74 as a membrane receptor for the pro-inflammatory cytokine macrophage migration inhibitory factor (MIF). MIF binding to CD74 activates downstream signaling through the MAPK and Akt pathways and promotes cell proliferation and survival. This interaction is likely regulated also by the presence of CD44, CXCR2 or CXCR4 as co-receptors.

Upregulation of CD74 expression has been observed in many types of cancer, as well as in certain infections and inflammatory conditions. Various formats of a humanized CD74-specific monoclonal antibody, hLL1, have been proposed for treatment of CD74-positive tumors (Chang C H et al., Blood 2005;106:4308-4314; Sapra P et al., Clin Can Res 2005;11:5257-5264; Stein R et al., Blood 2004;104:3705-11; Govindan S V et al. J Nucl Med 2000;41:2089-2097; Hertlein E et al., Blood 2010; 116: 2554-2558; Stein R et al., Clin Cancer Res 2009; 15: 2808-2817; Sharkey R M et al., J Nucl Med 2009; 50: 444-453; Lundberg B B et al., Drug Deliv 2007; 14: 171-175; Griffiths G L et al., Int J Cancer 1999; 81: 985-992; Griffiths G L et al., Cancer Res 2003; 9: 6567-6571; Ochakovskaya R et al., Clin Cancer Res 2001; 7: 1505-1510; Shih L et al., Cancer Immunol Immunother; Burton J D et al., Clin Cancer Res 2004; 10: 6606-6611; Lundberg B B et al., J Control Release 2004; 94: 155-161).

Although much progress has been made, there remains a need for improved methods of treating serious diseases, e.g. improved treatment of cancer, based on therapeutic antibodies and ADCs.

SUMMARY OF THE INVENTION

It is an object of the present invention to provide novel highly specific and effective monoclonal CD74-specific antibodies and ADCs of such CD74-specific antibodies. The antibodies or ADCs of the invention exhibit CD74 binding characteristics or other effects on CD74-expressing cells that differ from antibodies described in the art. Particularly, the antibodies are characterized by rapid internalization upon binding to CD74 antigen, making them suitable for therapeutic applications in the form of ADCs and for other applications where rapid internalization is an advantage. The novel ADCs are characterized by a high efficiency in killing CD74-expressing tumor cells.

The antibodies and corresponding ADCs can be provided in a variety of formats, including, but not limited to, antibody fragment and bispecific antibody formats. In preferred embodiments, the antibodies are human.

It is also an object of the present invention to provide ADCs based on such CD74-specific antibodies for medical use, providing an efficient and selective way of causing cell death of tumor cells.

These and other aspects of the invention are described in further detail below.

BRIEF DESCRIPTION OF THE DRAWINGS

FIGS. 1A-1F: Amino acid sequences of recombinant CD74 proteins used in the Examples. CD74v1 and v2, CD74del2-36v1 and v2, and HisCD74v1 and v2 correspond to SEQ ID NOS: 1-6, respectively.

FIGS. 2A and 2B: Alignment of variable heavy (VH) and variable light (VL) chain sequences of the antibodies of the present invention. The SEQ ID NO of each VH/VL sequence is listed within parentheses to the right of the sequence. Complementarity-determining regions (CDRs) according to IMGT nomenclature are highlighted as follows: sequences in italics represent CDR1, underlined sequences represent CDR2, and bold sequences represent CDR3.

(FIG. 15A) or 37° C. (FIG. 15B). Raji cells (FIG. 15C) and M4A4 cells (FIG. 15D) were incubated at 37° C.

DETAILED DESCRIPTION OF THE INVENTION

Definitions

Figure 3A:
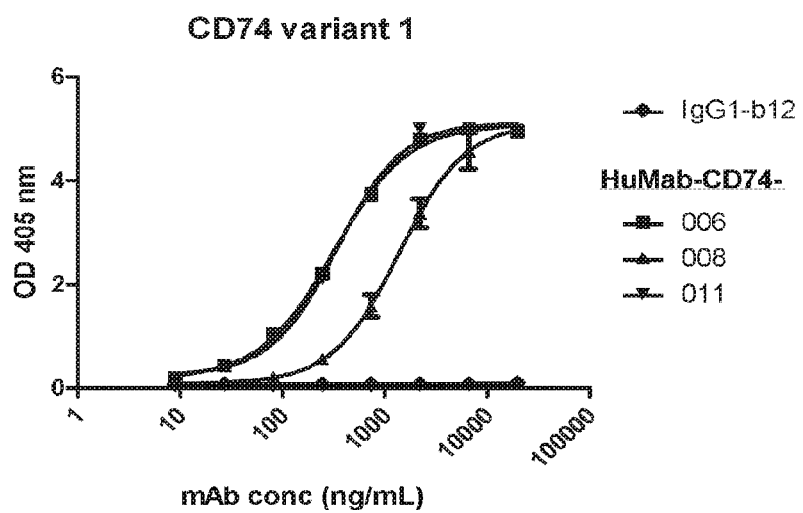
FIGS. 3A and 3B: Binding of CD74-specific antibodies to recombinant protein representing the extracellular domain of the variant 1 and 2 isoforms (CD74v1 and CD74v2), determined by ELISA. All human antibodies were produced by transiently co-transfecting HEK-293F cells with relevant heavy and light chain expression vectors.

The terms "CD74" and "CD74 antigen" are used interchangeably herein. Unless specified otherwise, the terms include any variants, isoforms and species homologs of human CD74 which are naturally expressed by cells or are expressed on cells transfected with the CD74 gene. At least four human isoforms are known to exist; p43, p41, p35 and pp33 (Borghese F et al., Expert Opin Ther Targets 2011; 15(3): 237-251). These result from alternative transcript splicing and two translation start sites. p43 (also known as CD74 isoform 1, isoform a, or "long"; see UniProt entry P04233-1 and NCBI Reference Sequence NP 001020330) contains 296 amino acids, with residues 73-296 forming the extracellular portion. Protein constructs of CD74 having the extracellular part of isoform 1 are herein referred to as "variant 1" or "CD74v1." p35 (also known as CD74 isoform 2, isoform b or "short"; see Uniprot entry P04233-2 and NCBI Reference Sequence NP 004346) lacks residues 209-272 from the extracellular part due to alternative splicing. Protein constructs of CD74 having the extracellular part of isoform 2 are herein referred to as "variant 2" or "CD74v2." p41 and p33 arise from an alternative translation start site (48 by downstream; 16 amino acids shorter protein) leading to variants lacking the endoplasmic reticulum (ER) retention signal that is present within these 16 amino acids, but having an identical extracellular part as p43 and p35, respectively. The sequence of another isoform (known as isoform 3 and isoform c), in which residues 148-160 are replaced and residues 161-296 are lacking, is provided in NP 001020329. The sequences of cynomolgus CD74 homologs are provided in, e.g., NCBI Reference Sequence: XP_001099491.2 and NCBI Reference Sequence: XP_002804624.1.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., $2^{nd}$ ed. Raven Press, N.Y. (1989)). Briefly, each heavy chain typically is comprised of a heavy chain variable region (abbreviated herein as $V_H$ or VH) and a heavy chain constant region ($C_H$ or CH). The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$ or CL. Typically, the numbering of amino acid residues in the constant region is performed according to the EU-index as described in Kabat et al., Sequences of Proteins of Immunological Interest, 5th Ed. Public Health Service, National Institutes of Health, Bethesda, Md. (1991). The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)).

The term "antibody" or "Ab" in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about eight hours, at least about 12 hours, about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An antibody may also be multispecific, having specificities for two or more different epitopes, typically non-overlapping. Examples of multispecific antibodies include bispecific antibodies, diabodies, and similar antibody molecules. As indicated above, the term antibody herein, unless otherwise stated or clearly contradicted by context, includes fragments of an antibody that retain the ability to specifically bind to the antigen. It has been shown that the antigen-binding function of an antibody may be performed by fragments of a full-length antibody, e.g., Fab and F(ab')$_2$ fragments. It also should be understood that the term antibody, unless specified otherwise, also includes polyclonal antibodies, monoclonal antibodies (mAbs), antibody-like polypeptides such as chimeric antibodies and humanized antibodies. An antibody as generated can possess any isotype.

The terms "human antibody", "human Ab" or "HuMab", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or transchromosomal non-human animal, such as a transgenic mouse, having a genome comprising a human heavy chain transgene and a light chain transgene, fused to an immortalized cell.

As used herein, "isotype" refers to the immunoglobulin class (for instance IgG1, IgG2, IgG3, IgG4, IgD, IgA, IgE, or IgM) that is encoded by heavy chain constant region genes.

The term "full-length antibody" when used herein, refers to an antibody which contains all heavy and light chain constant and variable domains that are normally found in an antibody of that isotype.

When used herein, unless contradicted by context, the term "Fab-arm" or "arm" refers to one heavy chain-light chain pair.

When used herein, unless contradicted by context, the term "Fc region" refers to an antibody region comprising at least one hinge region, a $C_H2$ domain, and a $C_H3$ domain.

An "antibody deficient in effector function" or an "effector function-deficient antibody" refers to an antibody which has a significantly reduced or no ability to activate one or more effector mechanisms, such as complement activation or Fc receptor binding. Thus, effector-function deficient antibodies have significantly reduced or no ability to mediate antibody-dependent cell-mediated cytotoxicity (ADCC) and/or complement-dependent cytotoxicity (CDC). An example of such an antibody is an antibody of IgG4 isotype or a hinge-stabilized form thereof. Another example is the introduction of mutations in Fc region which can strongly reduce the interaction with complement proteins and Fc receptors. See, for example, Bolt S et al., Eur J Immunol 1993, 23:403-411; Oganesyan, Acta Crys. 2008, D64, 700-704; and Shields et al., JBC 2001, 276: 6591-6604.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, mast cells and granulocytes, such as neutrophils, eosinophils and basophils. Some effector cells express specific Fc receptors (FcRs) and carry out specific immune functions. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell.

In the context of the present invention, an "ADC" refers to an antibody-drug conjugate, in the context of the present invention typically referring to a CD74-specific antibody, which is coupled to another moiety as described in the present application.

A "CD74 antibody", "anti-CD74 antibody", "CD74 Ab", "CD74-specific antibody" or "anti-CD74 Ab" is an antibody as described above, which binds specifically to the antigen CD74.

In a preferred embodiment, the antibody of the invention is isolated. An "isolated Ab," as used herein, is intended to refer to an antibody which is substantially free of other antibodies having different antigenic specificities (for instance an isolated antibody that specifically binds to CD74 is substantially free of antibodies that specifically bind antigens other than CD74). An isolated antibody that specifically binds to an epitope, isoform or variant of human CD74 may, however, have cross-reactivity to other related antigens, for instance from other species (such as CD74 species homologs). Moreover, an isolated antibody may be substantially free of other cellular material and/or chemicals. In one embodiment of the present invention, two or more "isolated" monoclonal antibodies having different antigen-binding specificities are combined in a well-defined composition.

When used herein in the context of two or more antibodies, the term "competes with" or "cross-competes with" indicates that the two or more antibodies compete for binding to CD74, e.g., to CD74 variants 1, 2 or both. For example, the constructs described in Example 1 can be used in such an assay. In one exemplary type of assay, CD74 is coated on a plate and allowed to bind the first antibody, after which the second, labeled antibody is added. If the presence of the first antibody reduces binding of the second antibody, the antibodies compete. The term "competes with" when used herein is also intended to cover combinations of antibodies where one antibody reduces binding of another antibody, but where no competition is observed when the antibodies are added in the reverse order.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. The epitope may comprise amino acid residues which are directly involved in the binding, and other amino acid residues, which are not directly involved in the binding, such as amino acid residues which are effectively blocked or covered by the specifically antigen binding peptide (in other words, the amino acid residue is within the footprint of the specifically antigen binding peptide).

As used herein, the term "binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using a soluble form of the antigen as the ligand and the antibody as the analyte. Typically, an antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein), which is not identical or closely related to the predetermined antigen. When the $K_D$ of the antibody is very low (that is, the antibody has a high affinity), then the $K_D$ with which it binds the antigen is typically at least 10.000-fold lower than its $K_D$ for a non-specific antigen.

The term "$k_d$" (sec$^{-1}$), as used herein, refers to the dissociation rate constant of a particular Ab-antigen interaction. Said value is also referred to as the $k_{off}$ value.

The term "$k_a$" (M$^{-1}$×sec$^{-1}$), as used herein, refers to the association rate constant of a particular Ab-antigen interaction.

The term "$K_D$" (M), as used herein, refers to the dissociation equilibrium constant of a particular Ab-antigen interaction.

The term "$K_A$" (M$^{-1}$), as used herein, refers to the association equilibrium constant of a particular Ab-antigen interaction and is obtained by dividing the $k_a$ by the $k_d$.

As used herein, "internalization", when used in the context of a CD74 antibody includes any mechanism by which the antibody is internalized from the cell-surface into a CD74-expressing cell. The internalization of an antibody can be evaluated in an indirect assay measuring the effect of an internalized Ab-toxin conjugate or a toxin specifically bound to an antibody by pre-incubation (such as, e.g., the anti-kappa-ETA' assay of Example 14).

As used herein, the term "inhibits growth" (e.g. referring to cells, such as tumor cells) is intended to include any measurable decrease in the cell growth when contacted with a CD74 antibody or ADC as compared to the growth of the same cells not in contact with a CD74 antibody or ADC, e.g., the inhibition of growth of a cell culture by at least about 10%, 20%, 30%, 40%, 50%, 60%, 70%, 80%, 90%, 99%, or 100%. Such a decrease in cell growth can occur by a variety of mechanisms, e.g. internalization, antibody-dependent cellular phagocytosis (ADCP), antibody-dependent cell-mediated cytotoxicity (ADCC), complement-dependent cytotoxicity (CDC), drug-mediated cell-kill and/or apoptosis.

The present invention also provides antibodies comprising functional variants of the $V_L$ region, $V_H$ region, or one or more CDRs of the antibodies of the examples. A functional variant of a $V_L$, $V_H$, or CDR used in the context of a CD74 antibody still allows the antibody to retain at least a substantial proportion (at least about 50%, 60%, 70%, 80%, 90%, 95% or more) of the affinity/avidity and/or the specificity/selectivity of the parent antibody and in some cases such a CD74 antibody may be associated with greater affinity, selectivity and/or specificity than the parent Ab.

Such functional variants typically retain significant sequence identity to the parent Ab. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The percent identity between two nucleotide sequences may be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences may also be determined using the algorithm described by E. Meyers and W. Miller (Comput. Appl. Biosci 4, 11-17 (1988)), which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch algorithm (Needleman and Wunsch, J. Mol. Biol. 48, 444-453 (1970)), which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, (e.g., about 65-95%, such as about 92%, 93% or 94%) of the substitutions in the variant are conservative amino acid residue replacements.

The sequences of CDR variants may differ from the sequence of the CDRs of the parent antibody sequences through mostly conservative substitutions; for instance at least 10, such as at least 9, 8, 7, 6, 5, 4, 3, 2 or 1 of the substitutions in the variant are conservative amino acid residue replacements.

The term "stabilized IgG4 antibody" refers to an IgG4 antibody which has been modified to reduce half-molecule exchange (see, e.g., international patent application publication WO2008145142 or van der Neut Kolfschoten M et al. (2007) Science 14;317(5844) and references therein.

In the context of the present invention, conservative substitutions may be defined by substitutions within the classes of amino acids reflected in one or more of the following three tables:

Amino Acid Residue Classes for Conservative Substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in e.g. Creighton (1984) Proteins: Structure and Molecular Properties (2d Ed. 1993), W.H. Freeman and Company.

Conservation in terms of hydropathic/hydrophilic properties and residue weight/size also is substantially retained in a variant CDR as compared to a CDR of an antibody of the examples (e.g., the weight class, hydropathic score, or both, of the sequences are at least about 50%, at least about 60%, at least about 70%, at least about 75%, at least about 80%, at least about 85%, at least about 90%, at least about 95%, or more (e.g., about 65-99%) retained). For example, conservative residue substitutions may also or alternatively be based on the replacement of strong or weak weight-based conservation groups, which are known in the art.

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 70-99%) similarity to the parent peptide.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication-defective retroviruses, adenoviruses and adeno-associated viruses), which serve equivalent functions.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NSO cells, and lymphocytic cells, and prokaryotic cells such as E. coli.

The term "transfectoma", as used herein, includes recombinant eukaryotic host cells expressing the Ab, such as CHO cells, PER.C6, NSO cells, HEK-293 cells, plant cells, or fungi, including yeast cells.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human Abs. For example, a transgenic mouse can have a human light chain transgene and either a human heavy chain transgene or human heavy chain transchromosome, such that the mouse produces human CD74 antibodies when immunized with CD74 antigen and/or cells expressing CD74. The human heavy chain transgene may be integrated into the chromosomal DNA of the mouse, as is the case for transgenic mice, for instance HuMAb® mice, such as HCo7 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, non-human animal can also be used for production of antibodies against a specific antigen by introducing genes encoding such specific Ab, for example by operatively linking the genes to a gene which is expressed in the milk of the animal.

"Treatment" refers to the administration of an effective amount of a therapeutically active compound of the present invention with the purpose of easing, ameliorating, arresting or eradicating (curing) symptoms or disease states.

An "effective amount" refers to an amount effective, at dosages and for periods of time necessary, to achieve a desired therapeutic result. A therapeutically effective amount of a CD74 antibody may vary according to factors such as the disease state, age, sex, and weight of the individual, and the ability of the CD74 antibody to elicit a desired response in the individual. A therapeutically effective amount is also one in which any toxic or detrimental effects of the antibody or antibody portion are outweighed by the therapeutically beneficial effects.

An "anti-idiotypic" (Id) antibody is an antibody which recognizes unique determinants generally associated with the antigen-binding site of an Ab.

Further Aspects and Embodiments of the Invention

The invention provides an isolated antibody, such as a human monoclonal antibody, which binds to human CD74 isoforms 1 and 2. The antibody may additionally bind to other CD74 isoforms or species homologs, such as the cynomolgus homolog. In particular, the antibody of the invention efficiently internalizes after binding to CD74 expressed on the surface of a cell, which is advantageous for therapeutic applications of an ADC approach. As shown in Examples 19 to 22, ADCs of CD74 antibodies and linker-drug combinations vcMMAE or mcMMAF effectively reduced the size of tumors in several in vivo tumor models. CD74 ADCs were surprisingly effective despite the low surface expression of the CD74 target on the tumor cells (Example 22). Further, CD74 antibodies were shown effective in preventing the outgrowth of tumors in an in vivo model of tumor prophylaxis (Example 25).

The antibody can be further characterized by one or more functional properties such that it binds to one or more human CD74 variants with high affinity, inhibits MIF binding to CD74, or any combination of the foregoing properties.

In one aspect, the antibody of the invention binds with high affinity to human CD74 variants 1 and/or 2 or to human cells naturally expressing CD74. For example, in one embodiment, the antibody (a) binds to the extracellular domain of CD74 variant 1 with an $EC_{50}$ (apparent affinity) of less than about 500 ng/mL, less than about 400 ng/mL, less than about 350 ng/mL, or less than about 330 ng/mL; b) binds to the extracellular domain of CD74 variant 2 with an $EC_{50}$ of less than about 400 ng/mL, less than about 300 ng/mL, less than about 250 ng/mL, or less than about 220 ng/mL; or (c) both of (a) and (b), when determined as described in Example 11. Also, or alternatively, the antibody may bind to CD74 on Raji cells with an $EC_{50}$ of less than about 400 ng/mL, less than about 300 ng/mL, less than about 250 ng/mL, or less than about 200 ng/mL, when determined as described in Example 12. Also, or alternatively, the antibody may bind to CD74 variants 1, 2 or both with a $K_D$ of about $10^{-8}$ M or less, such as about $10^{-9}$ M or less, or even about $10^{-10}$ M or less.

In one aspect, the antibody is internalized after binding to CD74 expressed on the surface of a cell. This can be determined according to the assay described in Example 24 using fluorescently labeled antibodies, according to the assay described in Example 14, using an ADC approach reflecting antibody internalization, or using a method described in Ong G L et al., Immunology 1999;98:296-302; Hansen H J et al., Biochem J 1996; 320: 293-300; Koch N G et al., J Immunol 1991; 147: 2643-2651; Roche P A et al., PNAS 1993; 90: 8581-8585). The cell may be from a B cell line, such as Raji cells, or from another type of tumor cell line induced to express high levels of CD74 by treatment with IFNγ (for example HT-29 colon cancer cells or SK-MEL-37 melanoma cells). In one embodiment, the cell is a Raji cell. In another embodiment, the antibody has an $EC_{50}$ of less than about 60 ng/mL, less than about 40 ng/mL, less than about 30 ng/mL, or about 25 ng/mL or less in inducing killing of Raji cells in an anti-kappa ETA' assay, when determined as described in Example 14. Alternatively, the antibody has an $EC_{50}$ between about 25 to about 60 ng/L about 25 to 40 ng/mL, or about 25 to about 30 ng/mL in such an assay.

In one aspect, an antibody of the invention has an $EC_{50}$ of less than 30 ng/mL, or an $EC_{50}$ of about 25 ng/mL or less, when determined as described in Example 14.

In one aspect, the antibody is characterized by its off-rate from CD74 antigen, optionally expressed on the surface of a cell. The off-rate can be determined, for example, using a cellular assay such as the one in Example 23, typically using fluorescently (or otherwise) labeled antibodies and determining the off-rate at 0° C. The cell may be from a B cell line, such as, e.g., Daudi or Raji cells, or from another suitable type of tumor cell line (e.g., M4A4 cells or NCI-H747 cells). In one embodiment, the cell is a Daudi cell. In one embodiment, the antibody has an off-rate in the range of 0.02 to 1.0 $min^{-1}$, such as about 0.03 to about 0.30 $min^{-1}$, such as 0.04 to 0.10 or 0.15 to 0.30 $min^{-1}$. In one embodiment, the antibody has an off-rate of about 0.07 $min^{-1}$. In one embodiment, the antibody has an off-rate of about 0.20 or 0.24 $min^{-1}$.

The antibody of the invention may also, or alternatively, be characterized by cross-competing with, or binding to the same epitope as, a reference antibody to human CD74 variant 1, variant 2, or both of variants 1 and 2.

An assay testing for competitive binding of the antibody with a reference antibody can utilize, e.g., the extracellular domain of a CD74 variant (e.g., the constructs described in Example 1), CD74-expressing cells and/or cell-membranes prepared from CD74-expressing cells. In an exemplary assay, CD74-expressing cells are pre-incubated with the test antibody at different concentrations, ranging from 1 to 100 µg/mL, subsequently incubated with a fluorophore-labeled reference antibody at a concentration of 10 µg/mL. Binding of the reference antibody is determined using FACS analysis.

In one aspect, the antibody competes for binding to variants 1 and 2 of human CD74 with at least one reference antibody selected from
(a) an antibody comprising a VH region comprising the sequence of SEQ ID NO:7 and a VL region comprising the sequence of SEQ ID NO:23 [005];
(b) an antibody comprising a VH region comprising the sequence of SEQ ID NO:11 and a VL region comprising the sequence of SEQ ID NO:26 [006];
(c) an antibody comprising a VH region comprising the sequence of SEQ ID NO:15 and a VL region comprising the sequence of SEQ ID NO:26 [008]; and
(d) an antibody comprising a VH region comprising the sequence of SEQ ID NO:19 and a VL region comprising the sequence of SEQ ID NO:26 [011].

In separate and specific embodiments, the antibody competes with the antibody of (a) and (b), (a) and (c), (a) and (d), (b) and (c), (b) and (d), (c) and (d), at least three of (a) to (d), or all of (a), (b), (c) and (d).

In one embodiment, the antibody binds to the same epitope on human CD74 as at least one of the reference antibodies defined in (a), (b), (c), and (d). This can be determined using known techniques for epitope determination, such as, e.g., testing for antibody binding to CD74 variants with differing point-mutations, or phage display techniques (see, e.g., Binder et al., Cancer Res 2007;67: 3518-3523; Carter J M et al., Curr Protocols Immunol 2004; Ch 9: Unit 9.4; Hjelm B et al., N Biotechnol 2010; 27: 129-137; Rockberg J et al., Curr Protocols Immunol 2010; Ch 9: Unit 9.9; Benjamin D C et al., Methods 1996; 9: 508-515).

An antibody or immunoglobulin of the invention may also or alternatively be characterized by comprising specific $V_H$, $V_L$, or CDR sequences, or specific combinations thereof.

In one aspect, the antibody or immunoglobulin comprises the $V_H$ CDR3 region of any one of HuMab-CD74-005, -006, -008, and -011. The invention thus provides for an antibody or immunoglobulin comprising a $V_H$ CDR3 comprising or consisting of a sequence selected from SEQ ID NOS:10, 14, 18, and 22. In one embodiment, the antibody or immunoglobulin comprises SEQ ID NO:22.

In one aspect, the antibody or immunoglobulin comprises a $V_L$ region comprising the CDR1, 2 and 3 sequences of SEQ ID NO:24, SEQ ID NO:27 and SEQ ID NO:26 and
a) a $V_H$ region comprising the CDR1, 2 and 3 sequences of SEQ ID NOS:8, 9 and 10 (005);
b) a $V_H$ region comprising the CDR1, 2 and 3 sequences of SEQ ID NO:12, 13 and 14 (006);
c) a $V_H$ region comprising the CDR1, 2 and 3 sequences of SEQ ID NO:16, 17 and 18 (008);
d) a $V_H$ region comprising the CDR1, 2 and 3 sequences of SEQ ID NO:20, 21 and 22 (011), or e) a variant of any of said antibodies or immunoglobulins, wherein said variant preferably has at most 1, 2 or 3 amino acid modifications, more preferably amino acid substitutions, such as conservative amino acid substitutions in any of said sequences.

In one aspect, the antibody comprises a $V_H$ region comprising the CDR1, 2 and 3 sequences of SEQ ID NO:20, 21 and 22 and a $V_L$ region comprising the CDR1, 2 and 3 sequences of SEQ ID NO:24, 27 and 25, with at most 3 amino acid modifications as compared to the original sequences. In one embodiment, the antibody comprises a $V_H$ region comprising the CDR1, 2 and 3 sequences of SEQ ID NO: 20, 21 and 22 and a $V_L$ region comprising the CDR1, 2 and 3 sequences of SEQ ID NO:24, SEQ ID NO:27 and SEQ ID NO:25, with at most 1 amino acid modification. In a particular embodiment of (e), the variant comprises an amino acid-substitution of residue 7 of the $V_H$ CDR2 of (d), such as a conservative amino acid substitution.

In one aspect, the antibody or immunoglobulin comprises a $V_H$ having
a) at least 80% identity, such as at least 90%, at least 95%, or at least 98% or 100% identity to a $V_H$ region sequence selected from the group consisting of SEQ ID NO:7, 11, 15 and 19, or
b) at most 20, such as 15, or 10, or 5, 4, 3, 2 or 1 amino acid modifications, more preferably amino acid substitutions, such as conservative amino acid substitutions as compared to a $V_H$ region sequence selected from the group consisting of SEQ ID NO:7, 11, 15 and 19.

In one aspect, the antibody or immunoglobulin comprises a $V_L$ having
a) at least 80% identity, such as at least 90%, at least 95%, or at least 98% or 100% identity to a $V_L$ region sequence selected from the group consisting of: SEQ ID NO:23 and 26 or
b) at most 20, such as 15, or 10, or 5, 4, 3, 2 or 1 amino acid modifications, more preferably amino acid substitutions, such as conservative amino acid substitutions as compared to a $V_L$ region sequence selected from the group consisting of: SEQ ID NO:23 and 26.

In one embodiment of (b), the $V_L$ region comprises an amino acid substitution in the position corresponding to residue 36 in SEQ ID NO:23 and 26. In SEQ ID NOS: 23 and 26, the amino acid at this position is F and Y, respectively.

In separate and specific aspects, the antibody or immunoglobulin comprises a $V_H$ and a $V_L$ region selected from any one of the following combinations:
a) a $V_H$ region comprising the sequence of SEQ ID NO:7 and a $V_L$ region comprising the sequence of SEQ ID NO:23 (005);
b) a $V_H$ region comprising the sequence of SEQ ID NO:11 and a $V_L$ region comprising the sequence of SEQ ID NO:26 (006);
c) a $V_H$ region comprising the sequence of SEQ ID NO:15 and a $V_L$ region comprising the sequence of SEQ ID NO:26 (008),
d) a $V_H$ region comprising the sequence of SEQ ID NO:19 and a $V_L$ region comprising the sequence of SEQ ID NO:26 (011), and
e) a $V_H$ region comprising the sequence of SEQ ID NO:7 and a $V_L$ region comprising the sequence of SEQ ID NO:26 (005/011); and
f) a variant of any of said antibodies or immunoglobulins, wherein said variant preferably has at most 1, 2 or 3 amino acid modifications, more preferably amino acid substitutions, such as conservative amino acid substitutions in any of said VH and/or VL region sequences.

In one aspect, the invention provides an antibody or immunoglobulin comprising a $V_L$ region comprising the sequence of SEQ ID NO: 26. In one embodiment, the antibody or immunoglobulin comprises the $V_H$ CDR3 of SEQ ID NO: 22. In another embodiment, the antibody comprises the $V_H$ CDR1, 2 and 3 sequences of SEQ ID NOS: 20, 21 and 22, respectively.

The antibody of the invention can be characterized by one or more of the functional or structural features of the aspects described above, or by any combination of selected functional and structural features. For example, in one embodiment, the antibody or immunoglobulin of the invention is characterized by any one of the following characteristics:
 a) an $EC_{50}$ of less than 30 ng/mL, or an $EC_{50}$ of about 25 ng/mL or less in an anti-kappa-ETA' assay, when determined as described in Example 14;
 b) competing with, or binding the same epitope as, an antibody having the $V_H$ and $V_L$ sequences of SEQ ID NOS:19 and 26, respectively;
 c) an off-rate in the range of 0.03 to 0.30 $min^{-1}$, when determined according to Example 23;
 d) a $V_H$ CDR3 comprising SEQ ID NO:22;
 e) a combination of (a) and (b);
 f) a combination of (a) and (c);
 g) a combination of (a) and (d);
 h) a combination of (b) and (c);
 i) a combination of (b) and (d);
 j) a combination of (c) and (d); or
 k) a combination of (a), (b), (c) and (d).

The antibodies of the invention are preferably monoclonal. Monoclonal antibodies of the present invention may e.g. be produced by the hybridoma method first described by Kohler et al. (Nature 256, 495 (1975)), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic and lymph node B cells obtained from mice immunized with an antigen of interest, for instance in the form of cells expressing an antigen of interest on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody of the invention is a human antibody. Human monoclonal antibodies directed against CD74 may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene minilocus that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and, in response to immunization, the introduced human heavy and light chain transgenes undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci. 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa; K) genes (as described in Chen et al., EMBO J. 12, 821-830 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the Hco7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-BALB/C mice can be generated by crossing HCo12 to KCo5[J/K]-Balb/C as described in WO 097006.

Splenocytes and lymph node cells from these transgenic mice may be used to generate hybridomas that secrete human monoclonal antibodies according to well known techniques.

Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of a CD74-specific antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1,κ.

In one embodiment, the antibody of the invention is a full-length antibody.

In one embodiment, the full-length antibody is an IgG1 antibody, such as an IgG1,κ antibody.

In another embodiment, the full-length antibody is an IgG4 antibody.

In a particular embodiment, the CD74-specific IgG4 antibody is a stabilized IgG4 antibody. Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, preferably lysine (described in WO2006033386) and/or wherein the hinge region comprises a Cys-Pro-Pro-Cys sequence. Other suitable stabilized IgG4 antbodies are disclosed in WO2008145142, which is hereby incorporated by reference in its entirety.

In one embodiment, the stabilized IgG4 CD74-specific antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys sequence in the hinge region. Preferably, said antibody comprises a Lys or Ala residue at the position corresponding to 409 or the $C_H3$ region of the antibody has been replaced by the $C_H3$ region of human IgG1, of human IgG2 or of human IgG3.

In another embodiment, the stabilized IgG4 CD74-specific antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions and wherein said antibody comprises a Cys-Pro-Pro-Cys sequence in the hinge region. Preferably, said antibody comprises a Lys or Ala residue at the position corresponding to 409 or the $C_H3$ region of the antibody has been replaced by the $C_H3$ region of human IgG1, of human IgG2 or of human IgG3.

In another embodiment, the CD74-specific antibody is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J. Immunol. 177(2):1129-1138 (2006) and Hezareh M, J. Virol. 75(24):12161-12168 (2001).

In one embodiment, the respective isotypes and/or sequences of the two heavy chain constant (Fc) regions are the same. In another embodiment, the respective isotypes and/or sequences of the two heavy-chain constant (Fc) regions of a single CD74-specific antibody are different. This is particularly applicable to multispecific, such as bispecific, CD74-specific antibodies, which are described in further detail below.

In another aspect, the antibody is an antigen-binding fragment. Antibody fragments can be obtained by conventional techniques, such as by fragmentation of full-length antibodies or by expression of nucleic acids encoding antibody fragments in recombinant cells (see, for instance Evans et al., J. Immunol. Meth. 184, 123-38 (1995)). The fragments can then be tested or screened for their properties in the same manner as described herein for full-length antibodies. The following describe exemplary formats for CD74-specific antigen-binding fragments of the invention:

F(ab')$_2$ fragments, which are bivalent fragments comprising two Fab fragments linked by a disulfide bridge at the hinge region. These can be generated by, e.g., treating a full-length antibody with pepsin.

Fab' or Fab fragments, which are monovalent fragments consisting of the $V_L$, $V_H$, $C_L$ and $C_H1$ domains. Fab fragments can be obtained, e.g., by treating an IgG antibody with papain. Fab' fragments can be obtained, e.g., by reducing the disulfide bridges of a F(ab')$_2$ fragment using a reducing agent such as dithiothreitol.

Monovalent antibodies or "antibody half-molecules", which exist in aqueous solutions as a heterodimer of a single light and single heavy chain, described in WO2007059782 (Genmab A/S).

Fd fragments, which consist essentially of the $V_H$ and $C_H1$ domains.

Fv fragments, which consist essentially of the $V_L$ and $V_H$ domains of a single arm of an antibody and single-chain antibodies thereof. Single-chain antibodies (also known as single chain Fv (scFv) antibodies) are constructs where the $V_L$ and $V_H$ domains of an Fv fragment are joined, using recombinant methods, by a synthetic linker that enables them to be expressed as a single protein chain in which the $V_L$ and $V_H$ regions pair to form monovalent molecules (see for instance Bird et al., Science 242, 423-426 (1988) and Huston et al., PNAS USA 85, 5879-5883 (1988)).

Domain antibodies (also called dAb fragments), which consists essentially of a $V_H$ domain (see, e.g., Ward et al., Nature 341, 544-546 (1989); Holt et al; Trends Biotechnol. 2003 November; 21(11):484-90).

Other exemplary formats include camelids or nanobodies (see, e.g., Revets et al; Expert Opin Biol Ther. 2005 January; 5(1):111-24).

Multispecific Antibody Formats

In another embodiment, the invention provides a multispecific antibody comprising a first antigen binding site from a CD74-specific antibody molecule described herein above and at least one second antigen binding site.

In a particular embodiment, the second antigen-binding site is used for recruiting a killing mechanism such as, for example, by binding an antigen on a human effector cell or by binding a cytotoxic agent or a second therapeutic agent. Exemplary effector cells include a T cell such as, for example, a cytolytic T cell (CTL)), a natural killer (NK) cell, a macrophage, a monocyte, a mast cell, and a granulocyte, such as, for example, a neutrophil, an eosinophil and a basophil. Exemplary effector cell-antigens include, but are not limited to, CD1, CD3, CD4, CD8, CD16, CD25, CD28, CD32, CD40, CD64, CD89, FcεRI and HLA-DR. Suitable cytotoxic agents and second therapeutic agents are exemplified below, and include toxins (such as radiolabeled peptides), chemotherapeutic agents and prodrugs.

In another particular embodiment, the second antigen-binding site binds to an antigen on a human B cell, such as, e.g., CD19, CD20, CD21, CD22, CD23, CD46, CD80, CD138 and HLA-DR.

In another particular embodiment, the second antigen-binding site binds a tissue-specific antigen, promoting localization of the bispecific antibody to a specific tissue.

In another particular embodiment, the second antigen-binding site binds to an antigen located on the same type of cell as the CD74-expressing cell, typically a tumor-associated antigen (TAA), but has a binding specificity different from that of the first antigen-binding site. Such multi- or bispecific antibodies can enhance the specificity of the tumor cell binding and/or engage multiple effector pathways. Exemplary TAAs include carcinoembryonic antigen (CEA), prostate specific antigen (PSA), RAGE (renal antigen), α-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, c-Met, C-myc, Marti., MelanA, MUM-1, MUM-2, MUM-3, HLA-B7, Ep-CAM or a cancer-associated integrin, such as a5133 integrin. Alternatively, the second antigen-binding site binds to a different epitope of CD74. The second antigen-binding site may alternatively bind an angiogenic factor or other cancer-associated growth factor, such as a vascular endothelial growth factor, a fibroblast growth factor, epidermal growth factor, angiogenin or a receptor of any of these, particularly receptors associated with cancer progression.

In another particular embodiment, the second antigen-binding site is from a second CD74-specific antibody, such as a CD74-specific antibody of the invention.

Exemplary formats for the multispecific antibody molecules of the invention include, but are not limited to (i) two antibodies cross-linked by chemical heteroconjugation, one with a specificity to CD74 and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')$_2$ fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody.

Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), Biclonic (Merus) and DuoBody (Genmab A/S) technologies.

In one embodiment, the bispecific antibody is obtained or obtainable via a controlled Fab-arm exchange, typically using DuoBody technology. In vitro methods for producing bispecific antibodies by controlled Fab-arm exchange have been described in WO 2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two mono-specific antibodies, both comprising IgG4-like $C_H3$ regions, upon incubation under reducing conditions. The resulting product is a bispecific antibody having two Fab arms which may comprise different sequences. In another exemplary method, described in WO 2011131746, bispecific antibodies of the present invention are prepared by a method comprising the following steps, wherein at least one of the first and second antibodies is a CD74 antibody of the present invention:

a) providing a first antibody comprising an Fc region of an immunoglobulin, said Fc region comprising a first CH3 region;

b) providing a second antibody comprising an Fc region of an immunoglobulin, said Fc region comprising a second CH3 region;

wherein the sequences of said first and second CH3 regions are different and are such that the heterodimeric interaction between said first and second CH3 regions is stronger than each of the homodimeric interactions of said first and second CH3 regions;

c) incubating said first antibody together with said second antibody under reducing conditions; and d) obtaining said bispecific antibody, wherein the first antibody is a CD74 antibody of the present invention and the second antibody has a different binding specificity, or vice versa.

The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting.

Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such assymetrical mutations, optionally wherein one or both Fc-regions are of the IgG1 isotype.

In one embodiment, the first Fc region has an amino acid substitution at a position selected from the group consisting of: 366, 368, 370, 399, 405, 407 and 409, and the second Fc region has an amino acid substitution at a position selected from the group consisting of: 366, 368, 370, 399, 405, 407 and 409, and wherein the first and second Fc regions are not substituted in the same positions.

In one embodiment, the first Fc region has an amino acid substitution at position 405, and said second Fc region has an amino acid substitution at a position selected from the group consisting of: 366, 368, 370, 399, 407 and 409, optionally 409.

In one embodiment, the first Fc region has an amino acid substitution at position 409, and said second Fc region has an amino acid substitution at a position selected from the group consisting of: 366, 368, 370, 399, 405, and 407, optionally 405 or 368.

In a particular embodiment, both the first and second Fc regions are of the IgG1 isotype, with the first Fc region having a Leu at position 405, and the second Fc region having an Arg at position 409.

Conjugates

The present invention provides a CD74-specific antibody conjugated to a therapeutic moiety, i.e. a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

Accordingly, in one aspect, the antibody according to any above-described aspect or embodiment is conjugated to a therapeutic moiety. Exemplary therapeutic moieties include a cytotoxic moiety, a radioisotope, a cytokine, and a lytic peptide.

In one embodiment, the antibody is capable of inducing cytotoxicity in a Raji cell by internalization of the antibody conjugated to or associated with a therapeutic moiety in the Raji cell, e.g., as described in Example 14 or a similar type of assay. In one embodiment, the antibody induces cytotoxicity by internalization as described in Example 14, with an $EC_{50}$ value between about 25 ng/mL and about 60 ng/ml, such as between 25 ng/mL and 30 ng/mL, or an $EC_{50}$ value less than 60 ng/mL, such as less than 40 ng/mL, or less than 30 ng/mL for inducing killing of Raji cells in an anti-kappa ETA' assay. In another embodiment, an ADC according to the present invention induces cytotoxicity with an $EC_{50}$ value less than 10 ng/mL, such as less than 5 ng/mL, less than 1 ng/mL, less than 0.5 ng/mL or less than 0.1 ng/mL in inducing killing of Raji cells or other CD74-expressing cells.

In one embodiment, the antibody is conjugated to a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, Aleurites fordii proteins, dianthin proteins, *Phytolacca americana* proteins such as PAPI, PAPII, and PAP-S, *momordica charantia* inhibitor, curcin, crotin, sapaonaria officinalis inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin.

In one embodiment, the antibody is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (US5663149) and anti-fungal activity (Pettit et al., (1998) Antimicrob. Agents and Chemother. 42:2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In one embodiment, the antibody is conjugated to pyrrolo [2,1-c][1,4]-benzodiazepine (PDB) or an analog, derivative or prodrug thereof. Suitable PDBs and PDB derivatives, and related technologies are described in, e.g., Hartley J. A. et al., Cancer Res 2010; 70(17): 6849-6858; Antonow D. et al., Cancer J 2008; 14(3):154-169; Howard P. W. et al., Bioorg Med Chem Lett 2009; 19: 6463-6466 and Sagnou et al., Bioorg Med Chem Lett 2000; 10(18): 2083-2086.

In one embodiment, the antibody is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof.

In a particular embodiment, the antibody is conjugated to an anthracycline or an analog, derivative or prodrug thereof. In another particular embodiment, the antibody is conjugated to maytansine or an analog, derivative or prodrug thereof. In another particular embodiment, the antibody is conjugated to calicheamicin or an analog, derivative or prodrug thereof. In another particular embodiment, the antibody is conjugated to duocarmycin or an analog, derivative or prodrug thereof. In another particular embodiment, the antibody is conjugated to rachelmycin (CC-1065) or an analog, derivative or prodrug thereof. In another particular embodiment, the antibody is conjugated to dolastatin 10 or an analog, derivative or prodrug thereof. In another particular embodiment, the antibody is conjugated to dolastatin 15 or an analog, derivative or prodrug thereof. In another particular embodiment, the antibody is conjugated to monomethyl auristatin E or an analog, derivative or prodrug thereof. In another particular embodiment, the antibody is conjugated to monomethyl auristatin F or an analog, derivative or prodrug thereof. In another particular embodiment, the antibody is conjugated to pyrrolo[2,1-c][1,4]-benzodiazepine or an analog, derivative or prodrug thereof. In another particular embodiment, the antibody is conjugated to irinotecan or an analog, derivative or prodrug thereof.

In one embodiment, a CD74-specific antibody of the invention is conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In another embodiment, a CD74-specific antibody of the invention is conjugated to an aptamer or a ribozyme.

In one embodiment, a CD74-specific antibody of the invention is conjugated, e.g., as a fusion protein, to a lytic peptide such as CLIP, Magainin 2, mellitin, Cecropin and P18.

In one embodiment, the antibody is conjugated to a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFN$\alpha$, IFN$\beta$, IFN$\gamma$, GM-CSF, CD40L, Flt3 ligand, stem cell factor, ancestim, and TNF$\alpha$.

In one embodiment, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecules. A radiolabeled CD74-specific antibody may be used for both diagnostic and therapeutic purposes. Non-limiting examples of radioisotopes include $^3$H, $^{14}$C, $^{15}$N, $^{35}$S, $^{90}$Y, $^{99}$Tc, $^{125}$I, $^{111}$In, $^{131}$I, $^{186}$Re, $^{213}$Bi, $^{225}$Ac and $^{227}$Th. For therapeutic purposes, a radioisotope emitting beta- or alpha-particle radiation can be used, e.g., $^{131}$I, $^{90}$Y, $^{211}$At, $^{212}$Bi, $^{67}$Cu, $^{186}$Re, $^{188}$Re, and $^{212}$Pb.

A therapeutic agent that may be administered in combination with a CD74-specific antibody of the present invention as described elsewhere herein, such as, e.g., a chemotherapeutic agent, anti-cancer cytokine or chemokine, is also a candidate for a therapeutic moiety useful for conjugation to an antibody of the present invention.

A CD74-specific antibody of the present invention may also be chemically modified by covalent conjugation to a polymer to, for instance, increase its circulating half-life. Exemplary polymers, and methods to attach them to polypeptides, are illustrated in for instance U.S. Pat. Nos. 4,766,106, 4,179,337, 4,495,285 and 4,609,546. Additional polymers include polyoxyethylated polyols and polyethylene glycol (PEG) (e.g., a PEG with a molecular weight of between about 1,000 and about 40,000, such as between about 2,000 and about 20,000).

A therapeutic or other agent may be conjugated either directly or indirectly to a CD74-specific antibody of the present invention, according to methods known in the art. One example of indirect conjugation of a second agent is via a spacer moiety to cysteine or lysine residues in the antibody. The therapeutic or other moiety may also or alternatively be conjugated to an N-(amino-) terminal or C-(carboxy-) terminal residue of a CD74-specific antibody polypeptide or fragment thereof (e.g., a CD74-specific antibody H or L chain) (see, e.g., Antibody Engineering Handbook, edited by Osamu Kanemitsu, published by Chijin Shokan (1994)). Conjugated antibody derivatives may also be generated by conjugation at internal residues or sugars, where appropriate. Exemplary methods are also described in, e.g., Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982).

In one embodiment, a CD74-specific antibody is conjugated to a prodrug molecule via a spacer or linker that can be activated in vivo to a therapeutic drug. For example, the prodrug moiety may be attached to the antibody via a linker, through the N- or C-terminus of the peptidic or non-peptidic drug moiety. After administration, the spacers or linkers are cleaved by tumor cell-associated enzymes or other tumor-specific conditions, by which the active drug is formed. Examples of such prodrug techologies and linkers are described in WO02083180, WO2004043493, WO2007018431, WO2007089149, WO2009017394 and WO201062171 by Syntarga B V, et al. (all incorporated herein by reference) Suitable antibody-prodrug technology and duocarmycin analogs can also be found in U.S. Pat. No. 6,989,452 (Medarex) (incorporated herein by reference). Suitable prodrug technology for auristatins is described in WO03026577 (Seatte Genetics) and other auristatin references mentioned above.

In one embodiment, a CD74-specific antibody is conjugated to a therapeutic moiety or prodrug via a linker sensitive to changes in pH or reducing conditions. Suitable linker technologies are known in the art, and include those described in, e.g., Ducry, L and Stump, Bioconjugate Chem. 2010; 21:5-13; Senter P. D., Current Opinion in Chemical Biology 2009; 13:235-244; and Carter, P. J. and Senter, P. D., The Cancer Journal 2010; 14:154-169.

In some embodiments, the linker is cleavable under intracellular conditions, such that the cleavage of the linker releases the drug unit from the antibody in the intracellular environment. In some embodiments, the linker is cleavable by a cleavable agent that is present in the intracellular environment (e.g. within a lysosome or endosome or caveolus). The linker can be, e.g. a peptidyl linker that is cleaved by an intracellular peptidase or protease enzyme, including but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside the target cells (see e.g. Dubowchik and Walker, 1999, Pharm. Therapeutics 83:67-123). In a specific embodiment, the peptidyl linker cleavable by an intracellular protease is a Val-Cit (valine-citrulline) linker or a Phe-Lys (phenylalanine-lysine) linker (see e.g. US6214345, which describes the synthesis of doxorubicin with the Val-Cit linker and different examples of Phe-Lys linkers). Examples of the structures of a Val-Cit and a Phe-Lys linker include but are not limited to MC-vc-PAB described below, MC-vc-GABA, MC-Phe-Lys-PAB or MC-Phe-Lys-GABA, wherein MC or mc is an abbreviation for maleimido caproyl, vc is an abbreviation for Val-Cit, PAB is an abbreviation for p-aminobenzylcarbamate and GABA is an abbreviation for γ-aminobutyric acid. An advantage of using intracellular proteolytic release of the therapeutic agent is that the agent is typically attenuated when conjugated and the serum stabilities of the conjugates are typically high.

In yet another embodiment, the linker unit is not cleavable and the drug is released by antibody degradation (see, e.g., US 2005/0238649). Typically, such a linker is not substantially sensitive to the extracellular environment. As used herein, "not substantially sensitive to the extracellular environment" in the context of a linker means that no more than 20%, typically no more than about 15%, more typically no more than about 10%, and even more typically no more than about 5%, no more than about 3%, or no more than about 1% of the linkers, in a sample of antibody-drug conjugate compound, are cleaved when the antibody-drug conjugate compound presents in an extracellular environment (e.g. plasma). Whether a linker is not substantially sensitive to the extracellular environment can be determined for example by incubating with plasma the antibody-drug conjugate for a predetermined time period (e.g. 2, 4, 8, 16 or 24 hours) and then quantitating the amount of free drug present in the plasma.

In a specific embodiment, the CD74-specific antibody is conjugated to MMAE (formula I):

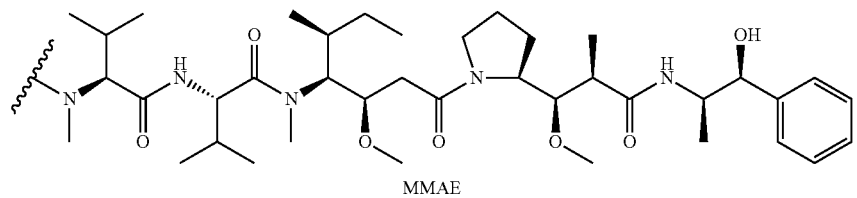 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE wherein the wavy line indicates the covalent attachment site for the linker.

In another specific embodiment, the CD74-specific antibody is conjugated to MMAF (formula II):

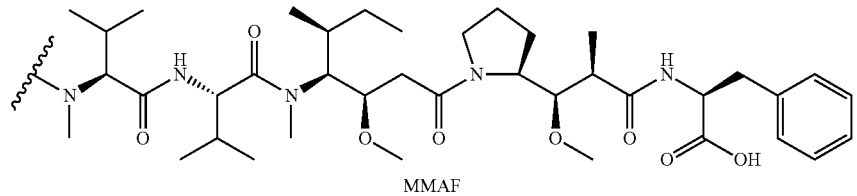

MMAF wherein the wavy line indicates the covalent attachment site for the linker.

In a particular embodiment, the linker to MMAE or MMAF is attached to sulfhydryl groups (free cysteine residues) of the CD74-specific antibody, obtained by (partial) reduction of the CD74-specific antibody.

In another particular embodiment, the linker-auristatin is MC-vc-PAB-MMAF (also designated as vcMMAF) or MC-vc-PAB-MMAE (also designated as vcMMAE (formula III and IV, respectively):

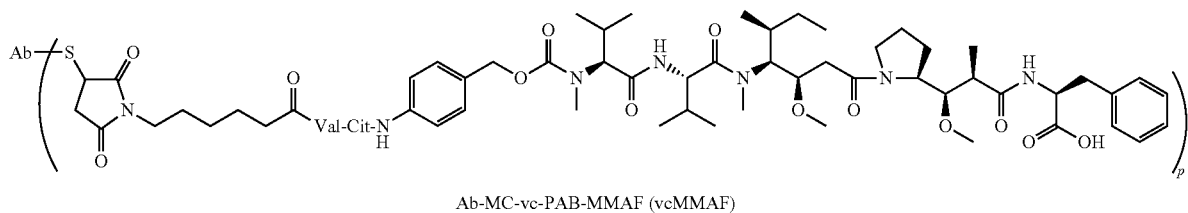

Ab-MC-vc-PAB-MMAF (vcMMAF)

-continued

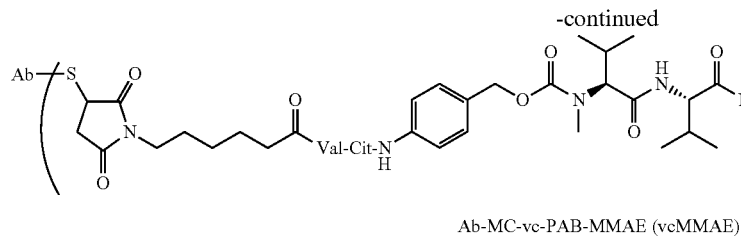

Ab-MC-vc-PAB-MMAE (vcMMAE)

wherein p denotes a number of from 1 to 8, S represents a free cysteine thiol residue of the CD74-specific antibody, and Ab designates the CD74-specific antibody. In one embodiment thereof, the linker-auristatin is vcMMAE. The vcMMAE drug linker moiety and conjugation methods are disclosed in WO2004010957, U.S. Pat. Nos. 7,659,241, 7,829,531, 7,851,437 and U.S. Ser. No. 11/833,028 (Seattle Genetics, Inc.), (which are incorporated herein by reference), and the vcMMAE drug linker moiety can be bound to the CD74-specific antibodies at the cysteines using a method similar to those disclosed in therein.

In another particular embodiment, the linker-conjugate is mcMMAF (formula V):

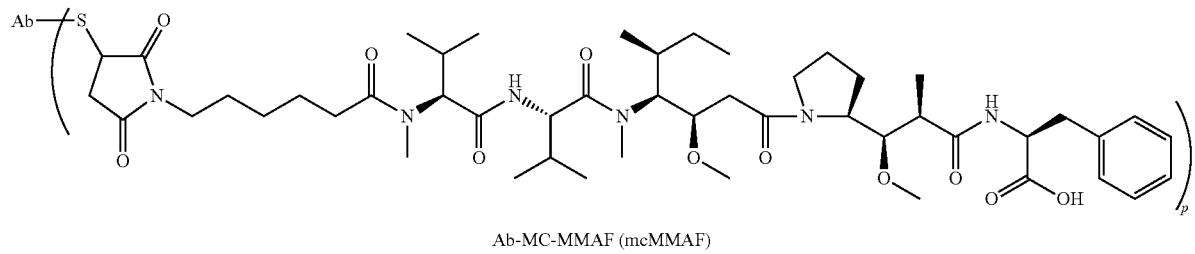

Ab-MC-MMAF (mcMMAF)

wherein p denotes a number of from 1 to 8, S represents a free cysteine thiol residue of the CD74-specific antibody, and Ab designates the CD74-specific antibody. The mcMMAF drug linker moiety and conjugation methods are disclosed in U.S. Pat. No. 7,498,298, U.S. Ser. No. 11/833,954, and WO2005081711 (Seattle Genetics, Inc.) (which are incorporated herein by reference), and the mcMMAF drug linker moiety can be bound to the CD74-specific antibodies at the cysteines using a method similar to those disclosed in therein.

In one aspect, the invention provides a CD74-specific ADC comprising an antibody binding to the same epitope as an antibody selected from 005, 006, 008 and 011, and a drug which is auristatin or an analog, derivative or prodrug thereof. In one embodiment, the $EC_{50}$ of the ADC in binding to the extracellular domain of CD47v1 is lower than about 0.2 µg/mL, such as lower than 0.1 µg/mL, or lower than about 0.05 µg/mL, optionally higher than 0.01 µg/mL, such as higher than 0.02 µg/mL, when determined in an assay as described in Example 16. In one embodiment, the CD74-specific ADC induces a cell kill higher than 70%, 80% or 90% when measured for Raji, Daudi or M4A4 cells in an assay as described in Example 18. In one embodiment, the CD74-specific ADC has an $IC_{50}$ of less than about 0.5 µg/mL, less than about 0.3 µg/mL, less than about 0.2 µg/mL, or less than about 0.1 µg/mL, and optionally higher than 0.005 µg/mL or about 0.01 µg/mL, in inducing killing of Raji, Daudi or M4A4 cells, when determined in an assay as described in Example 18. In one embodiment, the antibody comprises at least the VH CDR3, such as the VH CDR1, 2 and 3, optionally the VH CDR1, 2 and 3 and VL CDR1, 2 and 3 of 005, described in Table 3. In one embodiment, the antibody comprises at least the VH CDR3, such as the VH CDR1, 2 and 3, optionally the VH CDR1, 2 and 3 and VL CDR1, 2 and 3 of 006, described in Table 3. In one embodiment, the antibody comprises at least the VH CDR3, such as the VH CDR1, 2 and 3, optionally the VH CDR1, 2 and 3 and VL CDR1, 2 and 3 of 011, described in Table 3. In one embodiment, the drug is a monomethyl auristatin derivative, optionally selected from MMAE and MMAF.

In one aspect, the invention provides a CD74-specific ADC comprising an antibody comprising the CDR, VH and/or VL sequences of an antibody selected from the group consisting of 005, 006 and 011, and a drug selected from MMAE and MMAF. In one embodiment, the antibody is 005. In one embodiment, the antibody is 006. In one embodiment, the antibody is 011. In one particular embodiment, the antibody is 005 and the drug is MMAE, optionally vcMMAE. In one particular embodiment, the antibody is 005 and the drug is MMAF, optionally mcMMAF. In one particular embodiment, the antibody is 006 and the drug is MMAE, optionally vcMMAE. In one particular embodiment, the antibody is 006 and the drug is MMAF, optionally mcMMAF. In one particular embodiment, the antibody is 011 and the drug is MMAE, optionally vcMMAE. In one particular embodiment, the antibody is 011 and the drug is MMAF, optionally mcMMAF.

In specific and separate embodiments, the invention provides the following CD74-specific ADCs: 011-vcMMAE, 006-vcMMAE, 005-vcMMAE, 011-mcMMAF, 006-mcMMAF and 005-mcMMAF.

The cytostatic drug loading is represented by p and is the average number of cytostatic drug moieties per antibody in a molecule (also designated as the drug to antibody ratio, DAR). The cytostatic drug loading may range from 1 to 20 drug moieties per antibody and may occur on amino acids with useful functional groups such as, but not limited to, amino or sulfhydryl groups, as in lysine or cysteine.

Depending on the way of conjugation, p may be limited by the number of attachment sites on the antibody, for example where the attachment is a cysteine thiol, i.e., a sulphydryl group. Generally, antibodies do not contain many free and reactive cysteine thiol groups, i.e., sulphydryl groups, which may be linked to a drug moiety, as most cysteine thiol residues in antibodies exist as disulfide bridges. Therefore, in certain embodiments, an antibody may be reduced with a reducing agent such as dithiothreitol (DTT) or tricarbonylethylphosphine (TCEP), under partially or fully reducing conditions, to generate reactive sulphydryl groups. In certain embodiments, the drug loading for an ADC of the invention ranges from 1 to about 8, such as about 2 to 5, such as about 3 to 5, such as about 4. A maximum of 8 free sulphydryl groups can become available after (partial) reduction of the antibody (there are 8 cysteines involved in inter-chain disulfide bonding).

Expression Constructs

In further and separate aspects, the invention relates to nucleic acids encoding a sequence of an antibody of the invention, to expression vectors encoding the sequences of an antibody of the invention, to host cells comprising such expression vectors, to hybridomas which produce antibodies of the invention, and to methods of producing an antibody of the invention by culturing such host cells or hybridomas under appropriate conditions whereby the antibody is produced and, optionally, retrieved.

In one embodiment, the invention provides an expression vector comprising a nucleotide sequence encoding one or more amino acid sequences selected from SEQ ID NOS: 7-26. In one embodiment, the expression vector comprises one or more nucleotide sequences encoding one or more of the amino acid sequences selected from the group consisting of SEQ ID NOS: 7, 11, 15, 19, 23 and 26, or any combination thereof. In another embodiment, the expression vector comprises a nucleotide sequence encoding any one or more of the $V_H$ CDR3 amino acid sequences of SEQ ID NOS: 10, 14, 18 or 22. In another embodiment, the expression vector comprises a nucleotide sequence encoding a $V_H$ amino acid sequence selected from SEQ ID NOS: 7, 11, 15 and 19. In another embodiment, the expression vector comprises a nucleotide sequence encoding a $V_L$ amino acid sequence selected from SEQ ID NOS: 23 and 26. In another embodiment, the expression vector further comprises a nucleotide sequence encoding the constant region of a human antibody light chain, of a human antibody heavy chain, or both.

In a particular embodiment, the expression vector of the invention comprises a nucleotide sequence encoding variants of one or more of the above amino acid sequences, said variants having at most 25 amino acid modifications, such as at most 20, such as at most 15, 14, 13, 12 or 11 amino acid modifications, such as 10, 9, 8, 7, 6, 5, 4, 3, 2 or 1 amino acid modifications, such as deletions or insertions, preferably substitutions, such as conservative substitutions or at least 80% identity to any of said sequences, such as at least 85% identity or 90% identity or 95% identity, such as 96% identity or 97% identity or 98% identity or 99% identity to any of the afore-mentioned amino acid sequences.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a CD74-specific antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a $CaPO_4^-$-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the CD74-specific antibody in a bacterial cell. Examples of such vectors include expression vectors such as BlueScript (Stratagene), pIN vectors (Van Heeke & Schuster, J Biol Chem 264, 5503-5509 (1989)), pET vectors (Novagen, Madison Wis.) and the like.

An expression vector may also, or alternatively, be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

A nucleic acid and/or vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle-targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

In an expression vector of the invention, CD74-specific antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In one embodiment, the CD74-specific antibody-encoding expression vector is positioned in and/or delivered to the host cell or host animal via a viral vector.

Such expression vectors may be used for recombinant production of antibodies of the invention.

In one aspect, the invention provides a recombinant eukaryotic or prokaryotic host cell which produces the antibody of any aspect or embodiment described herein. Accordingly, the invention provides a recombinant eukaryotic or prokaryotic host cell, such as a transfectoma, which produces an antibody or immunoglobulin of the invention as defined herein. Examples of host cells include yeast, bacterial and mammalian cells, such as CHO or HEK-293 cells. For example, in one embodiment, the present invention provides a cell comprising a nucleic acid stably integrated into the cellular genome that comprises a sequence coding for expression of a CD74-specific antibody of the present invention. In another embodiment, the present invention provides a cell comprising a non-integrated nucleic acid, such as a plasmid, cosmid, phagemid, or linear expression element, which comprises a sequence coding for expression of a CD74-specific antibody of the invention.

In a further aspect, the invention relates to a hybridoma which produces an antibody of the invention as defined herein. In an even further aspect, the invention relates to a transgenic non-human animal or plant comprising nucleic acids encoding a human heavy chain and a human light chain, wherein the animal or plant produces an antibody of the invention. Generation of such hybridomas and transgenic animals or plants has been described above, and is further described in the Examples.

In a further aspect, the invention relates to a method for producing a CD74-specific antibody of the invention, said method comprising the steps of
a) culturing a hybridoma or a host cell of the invention as described herein above, and
b) retrieving and/or purifying the antibody of the invention from the culture media and, optionally,
c) preparing an ADC from the CD74-specific antibody.

In a further aspect, the nucleotide sequence encoding a sequence of an antibody of the invention further encodes a second moiety, such as a therapeutic polypeptide. Exemplary therapeutic polypeptides are described elsewhere herein. In one embodiment, the invention relates to a method for producing a CD74-specific antibody fusion protein, said method comprising the steps of
a) culturing a host cell comprising an expression vector comprising such a nucleotide sequence, and
b) retrieving and/or purifying the CD74-specific antibody fusion protein from the culture media.

Pharmaceutical Compositions

In one aspect, the invention provides a pharmaceutical composition comprising an antibody or ADC as defined in any of the above aspects and embodiments, and a pharmaceutically acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the antibody or antibody conjugate of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) on antigen binding).

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intra-arterial, intrathecal, intracapsular, intraorbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption-delaying agents, and the like that are physiologically compatible with a compound of the present invention.

Examples of suitable aqueous and nonaqueous carriers which may be employed in the pharmaceutical compositions of the present invention include water, saline, phosphate-buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-ortho-esters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Other active or therapeutic compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

The pharmaceutical composition of the present invention may contain one antibody or ADC of the present invention, a combination of an antibody or ADC according to the invention with another therapeutic compound, or a combination of compounds of the present invention.

Therapeutic Applications

In another aspect, the invention relates to the antibody or ADC of the invention, as defined in any aspect or embodiment herein, for use as a medicament.

The CD74-specific antibodies of the present invention can be used in the treatment or prevention of disorders involving cells expressing CD74. For example, the antibodies may be administered to cells in culture, e.g., in vitro or ex vivo, or to human subjects, e.g., in vivo, to treat or prevent disorders involving CD74-expressing cells. As used herein, the term "subject" is typically a human who responds to the CD74-specific antibody or ADC. Subjects may for instance include human patients having disorders that may be corrected or ameliorated by modulating CD74 function or by killing of the cell, directly or indirectly.

In one embodiment, the invention provides a method for modulating CD74-associated signaling in a CD74-expressing cell by contacting the cell with a CD74-specific antibody. A CD74-specific antibody of the invention may, for example, interfere with MIF-binding to CD74, which is a non-limiting example of how an antibody of the invention can modulate CD74-associated signaling.

In one embodiment, the invention provides a method for killing a CD74-expressing cell by contacting the cell with a CD74-specific antibody of the invention. Without being limited to theory, antibody-mediated crosslinking or clustering (e.g., due to the Fc-region of CD74-bound antibodies binding to FcR-expressing cells) of CD74 molecules on the surface of a cell can lead to apoptosis of the cell.

In one embodiment, the invention provides a method for killing a CD74-expressing cell by contacting the cell with a CD74-specific antibody of the invention in the presence of effector cells capable of inducing an Fc-mediated effector cell response such as a CDC, ADCC or ADCP response. In this embodiment, the antibody is typically full-length and of an isotype leading to a CDC or ADCC response, such as, e.g., an IgG1,κ isotype.

The CD74-specific antibodies of the invention are characterized by efficient internalization upon binding to CD74, making them suitable for an ADC approach using an ADC as described in any aspect or embodiment described herein.

Accordingly, in one embodiment, the invention provides a method for killing a CD74-expressing cell by contacting the cell with an ADC of the invention which requires internalization and trafficking to lysosomes for specific (i.e. cleavable linker) or non-specific (non-cleavable linker) proteolytic cleavage of the antibody-linker-drug complex. In another embodiment, the invention provides for a method of killing a CD74-expressing cell by contacting the cell with an ADC of the invention wherein the CD74-specific antibody is linked to a therapeutic moiety via a linker allowing for release of the drug once the ADC is internalized, e.g., by a change in pH or reducing conditions. Suitable linker technology is known in the art, as described above.

In another aspect, the present invention provides methods for treating or preventing a disorder involving cells expressing CD74 in a subject, which method comprises administration of a therapeutically effective amount of a CD74-specific antibody or ADC of the present invention to a subject in need thereof. The method typically involves administering to a subject a CD74-specific antibody or ADC in an amount effective to treat or prevent the disorder.

In a particular aspect, a CD74-specific antibody or ADC is administered prophylactically in order to reduce the risk of developing cancer, delay the onset of an event in cancer progression or reduce the risk of recurrence when a cancer is in remission and/or a primary tumor has been surgically removed. In the latter case, the CD74-specific antibody could, for example, be administered in association with (i.e., before, during, or after) the surgery. Prophylactic administration may also be useful in patients wherein it is difficult to locate a tumor that is believed to be present due to other biological factors.

Cells over-expressing CD74, such as cancer cells, are particularly good targets for the CD74-specific antibodies or ADCs of the invention, since more antibodies or ADCs may be bound per cell. Thus, in one aspect, the disorder involving cells expressing CD74 is cancer, i.e., a tumorigenic disorder, such as a disorder characterized by the presence of tumor cells expressing CD74 including, for example, disorders where the cells are from a solid tumor or hematological tumor. CD74 expression has been described in, e.g., breast cancer (Koretz K et al., Int J Cancer 1989; 44: 816-822), colorectal cancer (Cuthbert R J et al., Eur J Cancer 2009; 45:1654-1663), endometrial/cervical cancer (Glew S S et al., Cancer Res 1992; 52:4009-4016), gastric cancer (Tamori Y et al, Oncol Rep 2005; 14:873-877), squamous cell carcinoma of the head and neck (SCCHN) (Han J et al., Head Neck Oncol 2009; 1:27), lung cancer (McClelland M et al., Am J Pathol 2009; 174:638-646), glioblastoma (Kitange G J et al., J Neurooncol 2010; 100: 177-186), malignant lymphoma (Momburg F et al., Int J Cancer 1987; 40:598-603), B cell chronic lymhocytic leukemia (B-CLL) (Narni F et al., Blood 1986; 68:372-377), non-Hodgkin's lymphoma (NHL), monocytoid B cell lymphoma (MBCL) (Stroup R et al, Hum Pathol 1992; 23:172-177), hairy-cell leukemia (HCL) (Spiro R C et al., Leuk Res 1984; 8: 55-62), malignant melanoma (Weeraratna A T et al., Oncogene 2004; 23:2264-2274), ovarian cancer (Rangel L B et al., Cancer Biol Ther 2004; 3:1021-1027), prostate cancer (Meyer-Siegler K L et al., BMC Cancer 2005; 5:73), pancreatic cancer (Koide N et al., Clin Cancer Res 2006; 12:2419-2426), renal cancer (Saito T et al., Cancer Lett 1997; 115:121-127), thymic epithelial neoplasms (Datta M W et al., Appl Immunohistochem Mol Morphol 2000; 8:210-215), malignant fibrous histiosarcomas (Lazova R et al., Cancer 1997; 79:2115-2124), and pituitary adenomas (Rossi M L et al., Tumori 1990; 76:543-547). CD74 has also been found to be up-regulated in e.g., gastric epithelium during *H. pylori* infection and ulcerative colitis (Beswick, World J. Gastroenterol. 2009; 15(23):2855-61).

Exemplary cells expressing CD74 thus include cancer cells such as, e.g., cells from NHL, multiple myeloma (MM), ovarian cancer, breast cancer, pancreatic cancer, prostate cancer, gastric cancer, colorectal carcinoma and liver cancer.

In one aspect, the present invention provides methods for treating or preventing a hematological malignancy, which method comprises administration of a therapeutically effective amount of a CD74-specific antibody or ADC of the present invention to a subject in need thereof, and wherein the hematological malignancy is selected from a lymphoma, myeloma and/or a leukemia. In one embodiment, the hematological malignancy is selected from the group consisting of malignant lymphoma, B cell chronic lymphocytic leukemia (B-CLL), chronic myeloid leukemia (CML) in blast phase, NHL, MM, MBCL, HCL and T cell lymphoma.

In one embodiment, the hematological malignancy is NHL. The CD74-specific antibodies and ADCs of the present invention can, for example, be used in the treatment of both indolent and aggressive forms of NHL. Examples of B cell NHLs include lymphomatoid granulomatosis, follicular lymphoma, diffuse large B-cell lymphoma, mantle cell lymphoma, primary effusion lymphoma, intravascular large B cell lymphoma, mediastinal large B cell lymphoma, heavy chain diseases (including γ, μ, and α disease), lymphomas induced by therapy with immunosuppressive agents, such as cyclosporine-induced lymphoma, and methotrexate-induced lymphoma. In one embodiment, the hematological malignancy is multiple myeloma, such as, e.g., myeloma light chain disease and monoclonal gammapathy of undetermined significance (MGUS). In other separate and specific embodiments, the hematological malignancy is malignant lymphoma, B-CLL (such as, e.g., small lymphocytic lymphoma; SLL), CML in blast phase, MBCL, or HCL. In one embodiment, the hematological malignancy is a T cell lymphoma, such as, e.g., mycosis fungoides, peripheral T cell lymphomas unspecified, angioimmunoblastic T cell lymphoma, anaplastic large cell lymphoma (ALCL), enteropathy-associated T cell lymphoma, or hepatosplenic T cell lymphoma. In another embodiment, the hematological malignancy is Hodgkin's lymphoma. In another embodiment, the hematological malignancy is Waldenstrom's macroglobulinemia. In one embodiment, the hematological malignancy is CLL, such as B-CLL (e.g., small lymphocytic lymphoma; SLL).

In one aspect, the present invention provides methods for treating or preventing a solid tumor, which method comprises administration of a therapeutically effective amount of a CD74-specific antibody or ADC of the present invention to a subject in need thereof, and wherein the solid tumor is a melanoma, carcinoma, sarcoma, adenoma and/or a glioma. In one embodiment, the cancer is selected from the group consisting of breast cancer (such as, e.g., primary or metastatic breast cancer), colorectal cancer, endometrial/cervical cancer, gastric cancer, head and neck cancer (such as, e.g., SCCHN), hepatocellular carcinoma, lung cancer (such as, e.g., small cell lung cancer or non-small cell lung cancer), malignant glioma (such as, e.g., anaplastic astrocytoma and glioblastoma multiforme), malignant melanoma (such as, e.g., primary or metastatic melanoma), ovarian cancer (such as, e.g., serous, endometrioid or clear cell adenocarcinoma), pancreatic cancer, prostate cancer, renal cancer, bladder cancer, thymic cancer (such as, e.g., thymic carcinoma and invasive thymoma), malignant fibrous histiosarcoma, acoustic schwannoma, pituitary adenoma, and a soft tissue tumor.

In one embodiment, the cancer is ovarian cancer. In another embodiment, the cancer is selected from primary or metastatic breast cancer. In another embodiment, the cancer is pancreatic cancer, such as unresectable advanced or metastatic pancreatic cancer. In another embodiment, the cancer is prostate cancer. In another embodiment, the cancer is gastric cancer. In another embodiment, the cancer is colorectal carcinoma, such as metastatic colorectal carcinoma. In another embodiment, the cancer is hepatocellular carcinoma. In other separate and specific embodiments, the cancer is endometrial/cervical cancer, head and neck cancer, lung cancer, malignant glioma, malignant melanoma, ovarian cancer, renal cancer, thymic cancer, malignant fibrous histiosarcoma, acoustic schwannoma, pituitary adenoma, or a soft tissue tumor.

In one aspect, the present invention provides methods for treating or preventing an autoimmune disease, which method comprises administration of a therapeutically effective amount of a CD74-specific antibody or ADC of the present invention to a subject in need thereof. In one embodiment, the autoimmune disease is selected from an immune-mediated thrombocytopenia (such as acute idiopathic thrombocytopenic purpura and chronic idiopathic thrombocytopenic purpura), dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, poststreptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, primary biliary cinhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyofrophic lateral sclerosis, tabes dorsalis, giant cell arteritis/polymyalgia, pernicious anemia, rapidly progressive glomerulonephritis and fibrosing alveolitis.

In one embodiment, the autoimmune disease is rheumatoid arthritis. In another embodiment, the autoimmune disease is systemic sclerosis. In another embodiment, the autoimmune disease is multiple sclerosis. In another embodiment, the autoimmune disease is an inflammatory bowel disease, such as, e.g., Crohn's disease or ulcerative colitis.

In one embodiment, the invention provides a method of treatment of any one of the disorders of the above aspects and embodiments by administration to an individual in need thereof, of a CD74-specific antibody or ADC of any of the above aspects or embodiments. The invention also relates to CD74-specific antibodies or ADCs of the invention for use as a therapeutic, e.g., in the treatment of cancer or other disorder mentioned herein.

In an embodiment selection of patients to be treated with CD74-specific antibodies is based on the level of CD74 expression in a sample, such as a sample containing tumor cells, or by detecting CD74-expressing tumors using labeled CD74-specific antibodies or antibody fragments, e.g., those of the invention. Exemplary diagnostic assays for determining CD74-expression using CD74 antibodies or antibody fragment of the invention are described herein.

The efficient dosages and dosage regimens for the CD74-specific antibody or ADC depend on the disease or condition to be treated and may be determined by the persons skilled in the art.

A physician having ordinary skill in the art may readily determine and prescribe the effective amount of the pharmaceutical composition required. For example, the physician could start doses of the CD74-specific antibody employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above.

For example, an "effective amount" for therapeutic use may be measured by its ability to stabilize the progression of disease. The ability of a compound to inhibit cancer may, for example, be evaluated in an animal model system predictive of efficacy in human tumors. Alternatively, this property of a composition may be evaluated by examining the ability of the compound to inhibit cell growth or to induce cytotoxicity by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

An exemplary, non-limiting range for a therapeutically effective amount of a CD74-specific antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg.

An exemplary, non-limiting range for a therapeutically effective amount of a CD74-specific ADC of the invention is 0.02-100 mg/kg, such as about 0.02-30 mg/kg, such as about 0.05-10 mg/kg or 0.1-3 mg/kg, for example about 0.5-2 mg/kg.

Administration may e.g. be intravenous, intramuscular, intraperitoneal, or subcutaneous, and for instance administered proximal to the site of the target.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation.

In one embodiment, the efficacy-safety window is optimized by lowering specific toxicity such as for example by lowering the drug-antibody ratio (DAR) and/or mixing of CD74-specific ADC with unlabeled CD74-specific antibody.

In one embodiment, the efficacy of the treatment is monitored during the therapy, e.g. at predefined points in time. In one embodiment, the efficacy may be monitored by measuring the level of CD74 in a sample containing tumor cells, by visualization of the disease area, or by other diagnostic methods described further herein, e.g. by performing one or more PET-CT scans, for example using a labeled CD74-specific antibody, fragment or mini-antibody derived from the CD74-specific antibody of the present invention.

If desired, an effective daily dose of a pharmaceutical composition may be administered as two, three, four, five, six or more sub-doses administered separately at appropriate intervals throughout the day, optionally, in unit dosage forms. In another embodiment, the CD74-specific antibodies are administered by slow continuous infusion over a long period, such as more than 24 hours, in order to minimize any unwanted side effects.

While it is possible for a compound of the present invention to be administered alone, it is preferable to administer the compound as a pharmaceutical composition as described above.

An effective dose of a CD74-specific antibody or ADC of the invention may also be administered using a weekly, biweekly or triweekly dosing period. The dosing period may be restricted to, e.g., 8 weeks, 12 weeks or until clinical progression has been established.

For example, in one embodiment, the CD74-specific antibody or ADC is administered by infusion in a weekly dosage of between 10 and 500 mg/m$^2$, such as between 200 and 400 mg/m$^2$. Such administration may be repeated, e.g., 1 to 8 times, such as 3 to 5 times. The administration may be performed by continuous infusion over a period of from 1 to 24 hours, such as of from 1 to 12 hours.

In another embodiment, the CD74-specific antibody or ADC is administered by infusion every three weeks in a dosage of between 10 and 500 mg/m$^2$, such as between 50-200 mg/m$^2$. Such administration may be repeated, e.g., 1 to 8 times, such as 3 to 5 times. The administration may be performed by continuous infusion over a period of from 1 to 24 hours, such as of from 1 to 12 hours.

In one embodiment, a CD74-specific ADC is administered as a single dose of about 0.1-10 mg/kg, such as about 1-3 mg/kg, every week or every third week for up to twelve times, up to eight times, or until clinical progression. The administration may be performed by continuous infusion over a period of from 1 to 24 hours, such as of from 1 to 12 hours. Such regimens may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the CD74-specific antibodies of the present invention.

In one embodiment, the CD74-specific antibodies are administered as maintenance therapy, such as, e.g., once a week for a period of six months or more.

As non-limiting examples, treatment according to the present invention may be provided as a daily dosage of a compound of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Combinations

The invention also provides for therapeutic applications where an antibody or ADC of the invention is used in combination with at least one further therapeutic agent relevant for the disease or disorder to be treated, as described above. Such administration may be simultaneous, separate or sequential. For simultaneous administration the agents may be administered as one composition or as separate compositions, as appropriate.

Accordingly, the present invention provides methods for treating a disorder involving cells expressing CD74 as described above, which methods comprise administration of a CD74-specific antibody or ADC of the present invention combined with one or more additional therapeutic agents. The present invention also provides for the use of a CD74-specific antibody or ADC of the present invention for the preparation of a pharmaceutical composition to be administered with at least one chemotherapeutic agent for treating such a disorder.

The further therapeutic agent is typically relevant for the disorder to be treated. Exemplary therapeutic agents include other anti-cancer antibodies or ADCs, cytotoxic agents, chemotherapeutic agents, anti-angiogenic agents, anti-cancer immunogens, cell cycle control/apoptosis regulating agents, hormonal regulating agents, and other agents described below.

In one aspect, the further therapeutic agent is at least one second antibody or ADC which binds another target such as, e.g., CD4, CD5, CD8, CD14, CD15, CD19, CD21, CD22, CD23, CD25, CD30, CD33, CD37, CD38, CD40, CD40L, CD46, CD52, CD54, CD80, CD126, B7, MUC1, tenascin, HM1.24, or HLA-DR. For example, the second antibody may bind to a B cell antigen, including, but not limited to CD20, CD19, CD21, CD23, CD38, CD46, CD80, CD138, HLA-DR, CD22, or to another epitope on CD74. In another embodiment, the second antibody binds vascular endothelial growth factor A (VEGF-A). In separate and specific embodiments, the further therapeutic agent is a CD20- or a CD138-specific antibody.

In one embodiment, the CD74-specific antibody or ADC of the invention is for use in combination with a specific therapeutic antibody, such as veltuzumab, bevacizumab (Avastin®), zalutumumab, cetuximab (Erbitux®), panitumumab (Vectibix™), ofatumumab (Arzerra™), ocrelizumab, zanolimumab, daratumumab, ranibizumab (Lucentis®), Zenapax, Simulect, Remicade, Humira, Tysabri, Xolair, raptiva, nimotuzumab, rituximab and/or trastuzumab (Herceptin®). In one embodiment, the CD74-specific antibody or ADC of the present invention is administered in combination with a CD20-specific antibody such as, e.g., veltuzumab, ocrelizumab or ofatumumab (Arzerra™). In another embodiment, the CD74-specific antibody or ADC of the present invention is administered in combination with bevacizumab (Avastin®).

In one aspect, the invention provides an antibody or ADC of any of the above aspects or embodiments for the treatment of a disorder involving CD74-expressing cells, such as cancer, in combination with at least one chemotherapeutic agent.

In one embodiment, the chemotherapeutic agent is selected from an antimetabolite, such as methotrexate, 6-mercaptopurine, 6-thioguanine, cytarabine, floxuridine (FudR), 3',5'-O-dioleoyl-FudR, fludarabine, 5-fluorouracil, dacarbazine, hydroxyurea, asparaginase, gemcitabine, cladribine and similar agents.

In one embodiment, the chemotherapeutic agent is selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, and a platinum derivative such as cisplatin, carboplatin, and similar agents.

In one embodiment, the chemotherapeutic agent is selected from an anti-mitotic agent, such as taxanes, for instance docetaxel, and paclitaxel, and vinca alkaloids, for instance vindesine, vincristine, vinblastine, and vinorelbine.

In one embodiment, the chemotherapeutic agent is selected from a topoisomerase inhibitor, such as topotecan or irinotecan.

In one embodiment, the chemotherapeutic agent is selected from a cytostatic drug, such as etoposide and teniposide.

In one embodiment, the chemotherapeutic agent is selected from a growth factor receptor inhibitor, such as an inhibitor of ErbB1 (EGFR) (such as Iressa, erbitux (cetuximab), tarceva and similar agents), an inhibitor of ErbB2 (Her2/neu) (such as herceptin and similar agents) and similar agents.

In one embodiment, the chemotherapeutic agent is selected from a tyrosine kinase inhibitor, such as imatinib (Glivec, Gleevec STI571), lapatinib, PTK787/ZK222584 and similar agents.

In one aspect, the present invention provides a method for treating a disorder involving cells expressing CD74 in a subject, such as a cancer patient, which method comprises administration of a therapeutically effective amount of a CD74-specific antibody or ADC of the present invention and at least one inhibitor of angiogenesis, neovascularization, and/or other vascularization to a subject in need thereof.

Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other inhibitors of angiogenic tyrosine kinases (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF cDNA, cDNA coding for angiostatin, cDNA coding for p53 and cDNA coding for deficient VEGF receptor-2) and similar agents.

Other examples of such inhibitors of angiogenesis, neovascularization, and/or other vascularization are anti-angiogenic heparin derivatives and related molecules (e.g., heperinase III), temozolomide, NK4, cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combretastatin, canstatin, avastatin, antibodies against other relevant targets (such as anti-alpha-v/beta-3 integrin and anti-kininostatin mAbs) and similar agents.

In one embodiment, the therapeutic agent for use in combination with a CD74-specific antibody or ADC for treating the disorders as described above is an anti-cancer immunogen, such as a cancer antigen/tumor-associated antigen (e.g., epithelial cell adhesion molecule (EpCAM/TAC-STD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines), tumor-derived heat shock proteins, and similar agents. A number of other suitable cancer antigens/tumor-associated antigens known in the art may also or alternatively be used in such embodiment. Anti-cancer immunogenic peptides also include anti-idiotypic "vaccines" such as BEC2 anti-idiotypic antibodies (Mitumomab), CeaVac and related anti-idiotypic antibodies, anti-idiotypic antibody to MG7 antibody, and other anti-cancer anti-idiotypic antibodies (see for instance Birebent et al., Vaccine. 21(15), 1601-12 (2003), Li et al., Chin Med J (Engl). 114(9), 962-6 (2001), Schmitt et al., Hybridoma. 13(5), 389-96 (1994), Maloney et al., Hybridoma. 4(3), 191-209 (1985), Raychardhuri et al., J. Immunol. 137(5), 1743-9 (1986), Pohl et al., Int J. Cancer. 50(6), 958-67 (1992), Bohlen et al., Cytokines Mol. Ther. 2(4), 231-8 (1996) and Maruyama, J Immunol Methods. 264(1-2), 121-33 (2002)). Such anti-idiotypic antibodies may optionally be conjugated to a carrier, which may be a synthetic (typically inert) molecule carrier, a protein (for instance keyhole limpet hemocyanin (KLH) (see for instance Ochi et al., Eur J. Immunol. 17(11), 1645-8 (1987)), or a cell (for instance a red blood cell—see for instance Wi et al., J Immunol Methods. 122(2), 227-34 (1989)).

In one embodiment, the therapeutic agent for use in combination with a CD74-specific antibody or ADC for treating the disorders as described above is a cytokine, chemokine or cytokine/chemokine combination with cancer growth inhibitory properties. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1a from the human CXC and C-C chemokine families. Suitable cytokines include cytokine derivatives, cytokine variants, cytokine fragments, and cytokine fusion proteins. These and other methods or uses involving naturally occurring peptide-encoding nucleic acids herein may alternatively, or additionally, be performed by "gene activation" and homologous recombination gene upregulation techniques, such as those described in U.S. Pat. Nos. 5,968, 502, 6,063,630 and 6,187,305 and EP 0505500.

In one embodiment, the therapeutic agent for use in combination with a CD74-specific antibody or ADC for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxy-staurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In one embodiment, the therapeutic agent for use in combination with a CD74-specific antibody or ADC for treating the disorders as described above is a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an anti-androgene (such as flutaminde/eulexin), a progestin (such as such as hydroxy-progesterone caproate, medroxyprogesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane), a hormone inhibitor (such as octreotide/sandostatin) and similar agents.

In one embodiment, the therapeutic agent for use in combination with a CD74-specific antibody or ADC for treating the disorders as described above is an anti-anergic agent (for instance small molecule compounds, proteins, glycoproteins, or antibodies that break tolerance to tumor and cancer antigens). Examples of such compounds are molecules that block the activity of CTLA-4, such as MDX-010 (ipilimumab, Yervoy™) (Phan et al., PNAS USA 100, 8372 (2003)).

In one embodiment, the therapeutic agent for use in combination with a CD74-specific antibody or ADC for treating the disorders as described above is a tumor suppressor gene-containing nucleic acid or vector such as a replication-deficient adenovirus encoding human recombinant wild-type p53/SCH58500, etc.; antisense nucleic acids targeted to oncogenes, mutated, or deregulated genes; or siRNA targeted to mutated or deregulated genes. Examples of tumor suppressor targets include, for example, BRCA1, RB1, BRCA2, DPC4 (Smad4), MSH2, MLH1, and DCC.

In one embodiment, a therapeutic agent for use in combination with a CD74-specific antibody or ADC for treating the disorders as described above is an anti-cancer nucleic acid. Exemplary anti-cancer nucleic acids include genasense (augmerosen/G3139), LY900003 (ISIS 3521), ISIS 2503, OGX-011 (ISIS 112989), LE-AON/LEraf-AON (liposome encapsulated c-raf antisense oligonucleotide/ISIS-5132), MG98, and other antisense nucleic acids that target PKCa, clusterin, IGFBPs, protein kinase A, cyclin D1, or Bcl-2.

In one embodiment, the therapeutic agent for use in combination with a CD74-specific antibody or ADC for treating the disorders as described above is an anti-cancer inhibitory RNA molecule (see for instance Lin et al., Curr Cancer Drug Targets. 1(3), 241-7 (2001), Erratum in: Curr Cancer Drug Targets. 3(3), 237 (2003), Lima et al., Cancer Gene Ther. 11(5), 309-16 (2004), Grzmil et al., Int J. Oncol. 4(1), 97-105 (2004), Collis et al., Int J Radiat Oncol Biol Phys. 57(2 Suppl), S144 (2003), Yang et al., Oncogene. 22(36), 5694-701 (2003) and Zhang et al., Biochem Biophys Res Commun. 303(4), 1169-78 (2003)).

Compositions and combination administration methods of the present invention also include the administration of nucleic acid vaccines, such as naked DNA vaccines encoding such cancer antigens/tumor-associated antigens (see for instance U.S. Pat. Nos. 5,589,466, 5,593,972, 5,703,057, 5,879,687, 6,235,523, and 6,387,888). In one embodiment, the combination administration method and/or combination composition comprises an autologous vaccine composition. In one embodiment, the combination composition and/or combination administration method comprises a whole cell vaccine or cytokine-expressing cell (for instance a recombinant IL-2 expressing fibroblast, recombinant cytokine-expressing dendritic cell, and the like) (see for instance Kowalczyk et al., Acta Biochim Pol. 50(3), 613-24 (2003), Reilly et al., Methods Mol. Med. 69, 233-57 (2002) and Tirapu et al., Curr Gene Ther. 2(1), 79-89 (2002). Another example of such an autologous cell approach that may be useful in combination methods of the present invention is the MyVax® Personalized Immunotherapy method (previously referred to as GTOP-99) (Genitope Corporation—Redwood City, Calif., USA).

In one embodiment, a CD74-specific antibody or ADC according to the invention is combined or co-administered with a virus, viral proteins, or the like. Replication-deficient viruses, that generally are capable of one or only a few rounds of replication in vivo, and that are targeted to tumor cells, may for instance be useful components of such compositions and methods. Such viral agents may comprise or be associated with nucleic acids encoding immunostimulants, such as GM-CSF and/or IL-2. Both naturally oncolytic and such recombinant oncolytic viruses (for instance HSV-1 viruses, reoviruses, replication-deficient and replication-sensitive adenovirus, etc.) may be useful components of such methods and compositions. Accordingly, in one embodiment, the present invention provides combination compositions and combination administration methods wherein a CD74-specific antibody is combined or co-administered with an oncolytic virus. Examples of such viruses include oncolytic adenoviruses and herpes viruses, which may or may not be modified viruses (see for instance Shah et al., J. Neurooncol. 65(3), 203-26 (2003), Stiles et al., Surgery. 134(2), 357-64 (2003), Sunarmura et al., Pancreas. 28(3), 326-9 (2004), Teshigahara et al., J Surg Oncol. 85(1), 42-7 (2004), Varghese et al., Cancer Gene Ther. 9(12), 967-78 (2002), Wildner et al., Cancer Res. 59(2), 410-3 (1999), Yamanaka, Int J. Oncol. 24(4), 919-23 (2004) and Zwiebel et al., Semin Oncol. 28(4), 336-43 (2001).

Combination compositions and combination administration methods of the present invention may also involve "whole cell" and "adoptive" immunotherapy methods. For instance, such methods may comprise infusion or re-infusion of immune system cells (for instance tumor-infiltrating lymphocytes (TILS), such as CD4$^+$ and/or CD8$^+$ T cells (for instance T cells expanded with tumor-specific antigens and/or genetic enhancements), antibody-expressing B cells or other antibody-producing or -presenting cells, dendritic cells (e.g., dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In one embodiment, a CD74-specific antibody or ADC is delivered to a patient in combination with the application of an internal vaccination method. Internal vaccination refers to induced tumor or cancer cell death, such as drug-induced or radiation-induced, cryo-ablation-induced or radiofrequency ablation-induced cell death of tumor cells, in a patient, that typically leads to elicitation of an immune response directed towards (i) the tumor cells as a whole or (ii) parts of the tumor cells including (a) secreted proteins, glycoproteins or other products, (b) membrane-associated proteins or glycoproteins or other components associated with or inserted in membranes, and/or (c) intracellular proteins or other intracellular components. An internal vaccination-induced immune response may be humoral (i.e. antibody—complement-mediated) or cell-mediated (e.g., the development and/or increase of endogenous cytotoxic T lymphocytes that recognize the internally killed tumor cells or parts thereof). In addition to radiotherapy, non-limiting examples of drugs and agents that may be used to induce said tumor cell death and internal vaccination are conventional chemotherapeutic agents, cell-cycle inhibitors, anti-angiogenesis drugs, monoclonal antibodies, apoptosis-inducing agents, and signal transduction inhibitors.

Examples of other anti-cancer agents, which may be relevant as therapeutic agents for use in combination with a CD74-specific antibody or ADC for treating the disorders as described above are differentiation inducing agents, retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRalpha, PDGFRbeta, Flk2, Flt4, FGFR1, FGFR2, FGFR3, FGFR4, TRKA, TRKC, c-met, Ron, Sea, Tie, Tie2, Eph, Ret, Ros, Alk, LTK, PTK7 and similar agents.

Examples of other anti-cancer agents, which may be relevant as therapeutic agents for use in combination with a CD74-specific antibody or ADC for treating the disorders as described above are cathepsin B, modulators of cathepsin D dehydrogenase activity, glutathione-S-transferase (such as glutacylcysteine synthetase and lactate dehydrogenase), and similar agents.

Examples of other anti-cancer agents, which may be relevant as therapeutic agents for use in combination with a CD74-specific antibody for treating the disorders as described above are estramustine and epirubicin.

Examples of other anti-cancer agents, which may be relevant as therapeutic agents for use in combination with a CD74-specific antibody for treating the disorders as described above are a HSP90 inhibitors like 17-(Allylamino)-17-demethoxygeldanamycin, antibodies directed against a tumor antigen such as PSA, CA125, KSA, etc., integrins like integrin [3], inhibitors of VCAM and similar agents.

Examples of other anti-cancer agents, which may be relevant as therapeutic agents for use in combination with a CD74-specific antibody or ADC for treating the disorders as described above are calcineurin-inhibitors (such as valspodar, PSC 833 and other MDR-1 or p-glycoprotein inhibitors), TOR-inhibitors (such as sirolimus, everolimus and rapamcyin) and inhibitors of "lymphocyte homing" mechanisms (such as FTY720), and agents with effects on cell signaling such as adhesion molecule inhibitors (for instance anti-LFA, etc.).

In one embodiment, a CD74-specific antibody or ADC may be administered in connection with the delivery of one or more agents that promote access of the CD74-specific antibody or combination composition to the interior of a tumor. Such methods may for example be performed in association with the delivery of a relaxin, which is capable of relaxing a tumor (see for instance U.S. Pat. No. 6,719, 977). In one embodiment, a CD74-specific antibody or ADC of the present invention may be bonded to a cell penetrating peptide (CPP). Cell penetrating peptides and related peptides (such as engineered cell penetrating antibodies) are described in for instance Zhao et al., J Immunol Methods. 254(1-2), 137-45 (2001), Hong et al., Cancer Res. 60(23), 6551-6 (2000). Lindgren et al., Biochem J. 377(Pt 1), 69-76 (2004), Buerger et al., J Cancer Res Clin Oncol. 129(12), 669-75 (2003), Pooga et al., FASEB J. 12(1), 67-77 (1998) and Tseng et al., Mol. Pharmacol. 62(4), 864-72 (2002).

In yet another embodiment, the CD74-specific antibody or ADC is administered in conjunction with a CD74 up-regulating agent, such as, e.g., IFNγ or inactivated *H. pylori*.

In one embodiment, the present invention provides a method for treating a disorder involving cells expressing CD74 in a subject, which method comprises administration of a therapeutically effective amount of a CD74-specific antibody or ADC and at least one anti-inflammatory, immunosuppressive and/or immunomodulatory agent to a subject in need thereof.

In one embodiment such an anti-inflammatory agent may be selected from aspirin and other salicylates, Cox-2 inhibitors (such as rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL-6R antibodies, anti-IL-8 antibodies (e.g. antibodies described in WO2004058797, such as 10F8), anti-IL-15 antibodies (e.g. antibodies described in WO03017935 and WO2004076620), anti-IL-15 receptor Abs, anti-CD4 antibodies (e.g. zanolimumab), anti-CD11a antibodies (e.g., efalizumab), anti-alpha-4/beta-1 integrin (VLA4) antibodies (e.g. natalizumab), CTLA4-Ig for the treatment of inflammatory diseases, prednisolone, prednisone, disease modifying antirheumatic drugs (DMARDs) such as methotrexate, hydroxychloroquine, sulfasalazine, pyrimidine synthesis inhibitors (such as leflunomide), IL-1 receptor blocking agents (such as anakinra), TNF-α blocking agents (such as etanercept, infliximab, and adalimumab) and similar agents.

In one embodiment, such an immunosuppressive and/or immunomodulatory agent may be selected from cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), thymopentin, thymosin-α and similar agents.

In one embodiment, such an immunosuppressive and/or immunomodulatory agent may be selected from immunosuppressive Abs, such as antibodies binding to p75 of the IL-2 receptor, antibodies against CD25 (e.g. those described in WO2004045512, such as AB1, AB7, AB11, and AB12), antibodies against thymocyte globulin, or antibodies binding to for instance MHC, CD2, CD3 (such as, e.g., OKT3), CD4, CD7, CD28, B7, CD40, CD45, IFNγ, TNF-α, IL-4, IL-5, IL-6R, IL-7, IL-8, IL-10, CD11a, or CD58, or antibodies binding to their respective receptor(s) or ligand(s).

In one embodiment, such an immunosuppressive and/or immunomodulatory agent may be selected from soluble IL-15R, IL-10, B7 molecules (B7-1, B7-2, variants thereof, and fragments thereof), ICOS, and OX40, an inhibitor of a negative T cell regulator (such as an antibody against CTLA4) and similar agents.

In one embodiment, the present invention provides a method for treating a disorder involving cells expressing CD74 in a subject, which method comprises administration of a therapeutically effective amount of a CD74-specific antibody or ADC and an anti-C3b(i) antibody to a subject in need thereof.

In one embodiment, a therapeutic agent for use in combination with CD74-specific antibodies or ADCs for treating the disorders as described above may be selected from histone deacetylase inhibitors (for instance phenylbutyrate) and/or DNA repair agents (for instance DNA repair enzymes and related compositions such as dimericine).

Methods of the present invention for treating a disorder as described above comprising administration of a therapeutically effective amount of a CD74-specific antibody or ADC may also comprise anti-cancer directed photodynamic therapy (for instance anti-cancer laser therapy—which optionally may be practiced with the use of photosensitizing agent, see, for instance Zhang et al., J Control Release. 93(2), 141-50 (2003)), anti-cancer sound-wave and shock-wave therapies (see for instance Kambe et al., Hum Cell. 10(1), 87-94 (1997)), and/or anti-cancer nutraceutical therapy (see for instance Roudebush et al., Vet Clin North Am Small Anim Pract. 34(1), 249-69, viii (2004) and Rafi, Nutrition. 20(1), 78-82 (2004). Likewise, a CD74-specific antibody may be used for the preparation of a pharmaceutical composition for treating a disorder as described above to be administered with anti-cancer directed photodynamic therapy (for instance anti-cancer laser therapy—which optionally may be practiced with the use of photosensitizing agent), anti-cancer sound-wave and shock-wave therapies, and/or anti-cancer nutraceutical therapy.

In one embodiment, the present invention provides a method for treating a disorder involving cells expressing CD74 in a subject, which method comprises administration of a therapeutically effective amount of a CD74-specific antibody or ADC of the present invention, and radiotherapy to a subject in need thereof.

In one embodiment, the present invention provides a method for treating or preventing cancer, which method comprises administration of a therapeutically effective amount of a CD74-specific antibody or ADC of the present invention, and radiotherapy to a subject in need thereof.

In one embodiment, the present invention provides the use of a CD74-specific antibody or ADC of the present invention, for the preparation of a pharmaceutical composition for treating cancer to be administered in combination with radiotherapy.

Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In a further embodiment, the present invention provides a method for treating or preventing cancer, which method comprises administration to a subject in need thereof of a therapeutically effective amount of a CD74-specific antibody or ADC of the present invention, in combination with surgery.

As described above, a pharmaceutical composition of the present invention may be administered in combination therapy, i.e., combined with one or more agents relevant for the disease or condition to be treated either as separate pharmaceutical compositions or with a compound of the present invention co-formulated with one or more additional therapeutic agents as described above. Such combination therapies may require lower dosages of the compound of the present invention and/or the co-administered agents, thus avoiding possible toxicities or complications associated with the various monotherapies.

In one embodiment, the further therapeutic agent for a particular therapeutic use is selected from the following:

A CD20-specific antibody, particulary for treatment of a hematological malignancy such as, e.g., B-CLL or follicular lymphoma;

A CD138-specific antibody, particularly for treatment of a hematological malignancy such as, e.g., myeloma;

A CD38-specific antibody, particularly for treatment of a hematological malignancy such as, e.g., myeloma or CLL;

Melphalan (or melphalan hydrochloride) for treatment of a hematological malignancy such as, e.g., myeloma;

An anti-VEGF-A antibody such as, e.g., bevacizumab, particularly for treatment of a cancer such as, e.g., breast cancer;

Lenalidomide or bortezomib, particularly for treatment of a hematological malignancy such as, e.g., myeloma;

Fluorouracil or gemticabine, particularly for treatment of a cancer such as, e.g., pancreatic cancer;

Irinotecan, particularly for treatment of cancer such as, e.g., colorectal cancer, and Cisplatin or other platinum-derivative, particularly for treatment of a cancer such as, e.g., SCCHN.

Diagnostic Applications

The CD74-specific antibodies of the invention may also be used for diagnostic purposes, using a composition comprising a CD74-specific antibody as described herein. Accordingly, the invention provides diagnostic methods and compositions using the CD74-specific antibodies described herein. Such methods and compositions can be used for purely diagnostic purposes, such as detecting or identifying a disease involving CD74-expressing cells, as well as for monitoring of the progress of therapeutic treatments, monitoring disease progression, assessing status after treatment, monitoring for recurrence of disease, evaluating risk of developing a disease, and the like.

In one aspect, the CD74-specific antibodies of the present invention are used ex vivo, such as in diagnosing a disease in which cells expressing CD74 are indicative of disease or involved in the pathogenesis, by detecting levels of CD74 or levels of cells which express CD74 on their cell surface in a sample taken from a patient. This may be achieved, for example, by contacting the sample to be tested, optionally along with a control sample, with the CD74-specific antibody under conditions that allow for binding of the antibody to CD74. Complex formation can then be detected (e.g., using an ELISA). When using a control sample along with the test sample, the level of CD74-specific antibody or CD74-specific antibody-CD74 complex is analyzed in both samples and a statistically significant higher level of CD74-specific antibody or CD74-specific antibody-CD74 complex in the test sample indicates a higher level of CD74 in the test sample compared with the control sample.

Examples of conventional immunoassays in which CD74-specific antibodies of the present invention can be used include, without limitation, ELISA, RIA, FACS assays, plasmon resonance assays, chromatographic assays, tissue immunohistochemistry, Western blot, and/or immunoprecipitation.

In one embodiment, the invention relates to a method for detecting the presence of CD74 antigen, or a cell expressing CD74, in a sample comprising:
contacting the sample with a CD74-specific antibody of the invention under conditions that allow for binding of the CD74-specific antibody to CD74 in the sample; and
analyzing whether a complex has been formed. Typically, the sample is a biological sample.

In one embodiment, the sample is a tissue sample known or suspected of containing CD74 antigen and/or cells expressing CD74. For example, in situ detection of CD74 expression may be accomplished by removing a histological specimen from a patient, and providing the antibody of the present invention to such a specimen. The antibody may be provided by applying or by overlaying the antibody to the specimen, which is then detected using suitable means. It is then possible to determine not only the presence of CD74 or CD74-expressing cells, but also the distribution of CD74 or CD74-expressing cells in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

In the above assays, the CD74-specific antibody can be labeled with a detectable substance to allow CD74-bound antibody to be detected. Alternatively, bound (primary) CD74-specific antibody may be detected by a secondary antibody which is labeled with a detectable substance and which binds to the primary antibody.

The level of CD74 in a sample can also be estimated by a competition immunoassay utilizing CD74 standards labeled with a detectable substance and an unlabeled CD74-specific antibody. In this type of assay, the biological sample, the labeled CD74 standard(s) and the CD74-specific antibody are combined, and the amount of labeled CD74 standard bound to the unlabeled CD74-specific antibody is determined. The amount of CD74 in the biological sample is inversely proportional to the amount of labeled CD74 standard bound to the CD74-specific antibody.

Suitable labels for the CD74-specific antibody, secondary antibody and/or CD74 standard used in in vitro diagnostic techniques include, without limitation, various enzymes, prosthetic groups, fluorescent materials, luminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; and examples of suitable radioactive material include $^{125}$I, $^{131}$I, $^{35}$S, and $^{3}$H.

In one aspect, the CD74-specific antibodies of the invention are used in the in vivo imaging of CD74-expressing tissues such as tumors. For in vivo methods, antibody fragments such as, e.g., (Fab')$_2$, Fab and Fab' fragments, are particularly advantageous because of their rapid distribution kinetics.

In vivo imaging can be performed by any suitable technique. For example, a CD74-specific antibody (such as, e.g., a fragment) labeled with $^{99}$Tc, $^{131}$I, $^{111}$In or other gamma-ray emitting isotope may be used to image CD74-specific antibody accumulation or distribution in CD74-expressing tissues such as tumors with a gamma scintillation camera (e.g., an Elscint Apex 409ECT device), typically using low-energy, high resolution collimator or a low-energy all-purpose collimator. Alternatively, labeling with $^{89}$Zr, $^{76}$Br, $^{18}$F or other positron-emitting radionuclide may be used to image CD74-specific antibody or antibody fragment distribution in tumors using positron emission tomography (PET). The images obtained by the use of such techniques may be used to assess biodistribution of CD74 in a patient, mammal, or tissue, for example in the context of using CD74 as a biomarker for the presence of cancer cells. Variations on this technique may include the use of magnetic resonance imaging (MRI) to improve imaging over gamma camera techniques. Conventional immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in *Remington's Pharmaceutical Sciences*, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993). Moreover, such images may also, or alternatively, serve as the basis for surgical techniques to remove tumors. Furthermore, such in vivo imaging techniques may allow for the identification and localization of a tumor in a situation where a patient is identified as having a tumor (due to the presence of other biomarkers, metastases, etc.), but the tumor cannot be identified by traditional analytical techniques. All of these methods are features of the present invention.

The in vivo imaging and other diagnostic methods provided by the present invention are particularly useful in the detection of micrometastases in a human patient (e.g., a patient not previously diagnosed with cancer or a patient in a period of recovery/remission from a cancer).

In one embodiment, the present invention provides an in vivo imaging method wherein a CD74-specific antibody of the present invention is conjugated to a detection-promoting radio-opaque agent, the conjugated antibody is administered to a host, such as by injection into the bloodstream, and the presence and location of the labeled antibody in the host is assayed. Through this technique and any other diagnostic method provided herein, the present invention provides a method for screening for the presence of disease-related cells in a human patient or a biological sample taken from a human patient and/or for assessing the distribution of CD74-specific antibody prior to CD74-specific ADC therapy.

For diagnostic imaging, radioisotopes may be bound to a CD74-specific antibody either directly or indirectly by using an intermediary functional group. Useful intermediary functional groups include chelators, such as ethylenediaminetetraacetic acid and diethylenetriaminepentaacetic acid (see for instance U.S. Pat. No. 5,057,313).

In addition to radioisotopes and radio-opaque agents, diagnostic methods may be performed using CD74-specific antibodies that are conjugated to dyes (such as with the biotin-streptavidin complex), contrast agents, fluorescent compounds or molecules and enhancing agents (e.g. paramagnetic ions) for magnetic resonance imaging (MRI) (see, e.g., U.S. Pat. No. 6,331,175, which describes MRI techniques and the preparation of antibodies conjugated to a MRI enhancing agent). Such diagnostic/detection agents may be selected from agents for use in MRI, and fluorescent compounds. In order to load a CD74-specific antibody with radioactive metals or paramagnetic ions, it may be necessary to react it with a reagent having a long tail to which a multiplicity of chelating groups are attached for binding the ions. Such a tail may be a polymer such as a polylysine, polysaccharide, or another derivatized or derivatizable chain having pendant groups to which may be bound chelating groups such as, e.g., porphyrins, polyamines, crown ethers, bisthiosemicarbazones, polyoximes, and like groups known to be useful for this purpose. Chelates may be coupled to CD74-specific antibodies using standard chemistries.

Thus, the present invention provides a diagnostic CD74-specific antibody, wherein the CD74-specific antibody is conjugated to a contrast agent (such as for magnetic resonance imaging, computed tomography, or ultrasound contrast-enhancing agent) or a radionuclide that may be, for example, a gamma-, beta-, alpha-, Auger electron-, or positron-emitting isotope.

In a further aspect, the invention relates to a kit for detecting the presence of CD74 antigen or a cell expressing CD74, in a sample, comprising:

A CD74-specific antibody or ADC of the invention; and
Instructions for use of the kit.

In one embodiment, the present invention provides a kit for diagnosis of cancer comprising a container comprising a CD74-specific Ab, and one or more reagents for detecting binding of the CD74-specific antibody to CD74. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more CD74-specific Abs, of the present invention in labeled or unlabeled form in suitable container(s), reagents for the incubations for an indirect assay, and substrates or derivatizing agents for detection in such an assay, depending on the nature of the label. Control reagent(s) and instructions for use also may be included.

Diagnostic kits may also be supplied for use with a CD74-specific Ab, such as a conjugated/labeled CD74-specific Ab, for the detection of the presence of CD74 in a tissue sample or host. In such diagnostic kits, as well as in kits for therapeutic uses described elsewhere herein, a CD74-specific antibody typically may be provided in a lyophilized form in a container, either alone or in conjunction with additional antibodies specific for a target cell or peptide. Typically, a pharmaceutically acceptable carrier (e.g., an inert diluent) and/or components thereof, such as a Tris, phosphate, or carbonate buffer, stabilizers, preservatives, biocides, inert proteins, e.g., serum albumin, or the like, also are included (typically in a separate container for mixing) and additional reagents (also typically in separate container(s)). In certain kits, a secondary antibody capable of binding to the CD74-specific Ab, which typically is present in a separate container, is also included. The second antibody is typically conjugated to a label and formulated in a manner similar to the CD74-specific antibody of the present invention. Using the methods described above and elsewhere herein, CD74-specific antibodies may be used to define subsets of cancer/tumor cells and characterize such cells and related tumor tissues.

Anti-Idiotypic Antibodies

In a further aspect, the invention relates to an anti-idiotypic antibody which binds to a CD74-specific antibody of the invention as described herein.

An anti-idiotypic (Id) antibody is an antibody which recognizes unique determinants generally associated with the antigen-binding site of an antibody. An anti-Id antibody may be prepared by immunizing an animal of the same species and genetic type as the source of a CD74-specific monoclonal antibody with the monoclonal antibody to which an anti-Id is being prepared. The immunized animal typically can recognize and respond to the idiotypic determinants of the immunizing antibody by producing an antibody to these idiotypic determinants (the anti-Id antibody). Such antibodies are described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id antibody may be epitopically identical to the original mAb, which induced the anti-Id antibody. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein with respect to CD74-specific antibodies of the present invention. For example, a monoclonal anti-Id antibody may be coupled to a carrier such as keyhole limpet hemocyanin (KLH) and used to immunize BALB/c mice. Sera from these mice typically will contain anti-anti-Id antibodies that have the binding properties similar, if not identical, to an original/parent CD74-specific antibody.

The present invention is further illustrated by the following examples which should not be construed as further limiting.

EXAMPLES

Example 1

Construction of CD74v1 and -v2, His-CD74v1 and -v2 and CD74de12-36v1 and -v2 Expression Vectors The encoding sequences for human CD74 variant 1 (CD74v1) (identical to Genbank sequence NP_001020330) and human CD74 variant 2 (CD74v2) (identical to Genbank sequence AAV383110330) were made synthetically and fully codon optimized (GeneArt, Regensburg, Germany). The constructs were cloned in the mammalian expression vector pEE13.4 (Lonza Biologics, Slough, UK). These constructs were named pEE13.4CD74v1 and pEE13.4CD74v2. To enhance the expression level of CD74 on the cell surface, the cytoplasmic ER retention signal (aa2-36) was removed as described (Khalil H et al., J Cell Sci 2005; 118: 4679-4687). To this end, new constructs were made by amplifying the CD74-encoding regions from pEE13.4CD74v1 and pEE13.4CD74v2, and removing the aa2-36 encoding regions in the process. These PCR fragments were recloned in pEE13.4 and fully sequenced to confirm the correctness of the new constructs. These expression vectors were named pEE13.4CD74v1de12-36 and pEE13.4CD74v2de12-36.

The encoding regions for the extracellular domains of CD74v1 (aa 73-296) and -v2 (aa 73-232) were amplified by PCR from pEE13.4CD74v1 and pEE13.4CD74v2, in the process introducing the encoding region for a hexameric N-terminal His tag. The PCR fragments were cloned in mammalian expression vector pEE12.4 (Lonza Biologics) containing the encoding region of an efficient signal peptide (HMM38 [Barash S et al., Biochem Biophys Res Commun 2002; 294: 835-842). The expression vectors were fully sequenced and named pEE12.4SPH is CD74v1 and pEE12.4SPH is CD74v2. The resulting proteins were named H is CD74v1 and H is CD74v2.

The protein sequences of CD74 variants are shown in FIG. 1.

Example 2

Transient Expression in HEK-293F Cells and in CHO-S Cells

Freestyle™ 293-F (a HEK-293 subclone adapted to suspension growth and chemically defined Freestyle medium; HEK-293F) cells were obtained from Invitrogen and transfected with pEE13.4CD74v1, pEE13.4CD74v2, pEE13.4CD74de12-36v1, pEE13.4CD74de12-36v2, pEE12.4SPH is CD74v1 or pEE12.4SPH is CD74v2, using 293fectin (Invitrogen) according to the manufacturer's instructions.

Cell culture supernatants, in the case of pEE12.4SPH is CD74v1 or pEE12.4CD74v2, were harvested and soluble His CD74v1 or His CD74v2 was purified by metal affinity chromatography, as described below.

In the case of pEE13.4CD74v1, pEE13.4CD74v2, pEE13.4CD74v1de12-36 or pEE13.4CD74v2de12-36, cells were harvested 1-2 days post transfection and used in subsequent assays. These cells were named TH2013-CD74v1, TH2013-CD74v2, TH2013-CD74v1de12-36 and TH2013-CD74v2de12-36.

A suspension-adapted CHO-K1SV cell line (CHO-S, Invitrogen) was transfected with pEE13.4CD74v1, pEE13.4CD74v2, pEE13.4CD74v1de12-36 or pEE13.4CD74v2de12-36, according to the manufacturer's protocol using the CHO-Max reagent (Invitrogen). Transfected CHO-S cells were harvested 1-2 days post transfection and used in subsequent assays. These cells were named TC2013-CD74v1, TC2013-CD74v2, TC2013-CD74v1de12-36 and TC2013-CD74v2de12-36.

In the case of antibody expression, the appropriate heavy chain and light chain vectors, as described in Example 9, were co-expressed in HEK-293F cells as described supra.

Example 3

Stable Expression in NSO Cells

The pEE13.4CD74v1de12-36 plasmid was transfected in NSO cells (Lonza Biologics). Cells were selected for stable integration of the expression vector by culture in glutamine-free cell culture medium in the presence of 25 μM methyl-sulphoximine (MSX) as described (Bebbington C R et al., Biotechnology (NY) 1992; 10:169-175). Cells expressing CD74 were pooled and used as a semi-stable population or individual stable clones were selected and used. These cells were named N2013de1-v1-012.

Example 4

Purification of His-Tagged CD74

His CD74v1 and His CD74v2 were expressed in HEK-293F cells. The His-tag in the proteins enables purification with immobilized metal affinity chromatography. In this process, a chelator fixed onto the chromatographic resin is charged with $Co^{2+}$ cations. CD74ECDHis-containing supernatant is incubated with the resin in batch mode (i.e. solution). His-tagged protein binds strongly to the resin beads, while other proteins present in the culture supernatant do not bind strongly. After incubation, the beads are retrieved from the supernatant and packed into a column. The column is washed in order to remove weakly bound proteins. The strongly bound CD74ECDHis proteins are then eluted with a buffer containing imidazole, which competes with the binding of H is to $Co^{2+}$. The eluent is removed from the protein by buffer exchange on a desalting column.

Example 5

Immunization Procedure of Transgenic Mice

Antibodies HuMab-CD74-005, -006, -008 and -011 were derived from the immunizations of HCo17 HuMAb mice (human monoclonal antibody; Medarex Inc., San Jose, Calif., USA) which have four genetic modifications. These mice were made transgenic for the human Ig heavy and human Ig kappa light chain and double knock out for the mouse heavy and mouse kappa light chain loci. These disruptions prevent the expression of any antibodies that are completely murine. Different strains were used; HCo12, HCo12-BALB/c, HCo17 and HCo20. These differ in the number of human VH (variable region of heavy chain) and VL (variable region of light chain) genes. HCo12-BALB/c mice were derived by crossbreeding with KCo5-BALB/c (kappa light chain transgenic) mice.

Six different immunogens were used for the immunizations: TH2013-CD74v1de12-36, TH2013-CD74v2de12-36, N2013de1-v1-012, SU-DHL-4 cells (Human B cell lymphoma cell line) and H is CD74v1 or H is CD74v2 coupled to the carrier protein KLH (Keyhole Limpet Hemocyanin). Mice were immunized every fortnight, alternating with $5\times10^6$ cells or with 15 μg of protein. Eight immunizations were performed in total, four intraperitoneal (IP) and four subcutaneous (SC).

Antibodies-005, -006 and -008 were obtained from immunization of an HCo17 mouse with $5\times10^6$ TH2013-CD74v1de12-36 cells IP, alternated with 15 μg His CD74v2 SC. The first immunization was performed IP, with cells in complete Freund's adjuvant (CFA; Difco Laboratories, Detroit, Mich., USA), the following immunizations in incomplete Freund's adjuvant (IFA) (protein, SC) or in PBS (cells, IP).

Antibody -011 was obtained from the immunization of an HCo17 mouse with $5\times10^6$ TH2013-CD74v1de12-36 cells IP, alternated with 15 μg H is CD74v1 SC. The first immunization was performed with protein in CFA (IP), the following immunizations in IFA (protein, SC) or PBS (cells, IP).

When serum titers were found to be sufficient (dilution of serum of 1/50 or lower found positive in antigen-specific screening assay as described in Example 6 on at least two sequential, biweekly, screening events), mice were additionally boosted twice intravenously (IV) with 10 μg H is CD74 protein in 100 μL PBS, four and three days before fusion.

Example 6

Homogeneous Antigen-Specific Screening Assay

Mouse sera and hybridoma supernatants were analyzed in a high throughput screening (HTS) Fluorometric Micro Volume Assay Technology (FMAT assay; Applied Biosystems, Foster City, Calif., USA) for the presence of anti-CD74 antibodies. In this assay, TC2013-CD74v1de12-36 and TC2013-CD74v2de12-36 cells were used to detect human anti-CD74 antibodies. Wild type CHO-S cells were used to measure non-specific binding. Samples were added to the cells to allow binding to CD74. Subsequently, binding of HuMab was detected using a fluorescent conjugate (Goat anti-human IgG-Cy5; Jackson Immunoresearch). Mouse anti-human CD74 antibody (Becton Dickinson; IgG2a, K;

clone M-B741), labeled with Alexa-647, as described below, was used as a positive control and mouse-chrompure (Jackson Immunoresearch) labeled with Alexa-647 was used as a negative control.

Antibodies were labeled with Alexa Fluor® 647 Dye (Molecular Probes), hereinafter "Alexa-647", using the following procedure:

An antibody solution of 1 mg/mL IgG was prepared in 0.1 M sodium carbonate buffer pH 9.0 (NaHCO$_3$, Riedel de Haen, cat. no. 31437). Alexa-647 was prepared freshly, by adding 100 μL DMSO (Sigma, cat. no. D2438) and 900 μL 0.1 M sodium carbonate buffer pH 9.0 to one vial (Alexa Fluor® 647 carboxylic acid, succinimidyl ester (1 mg/vial), Molecular Probes, Leiden, The Netherlands, cat. no. A-20006). A five-times molar excess of Alexa-647, calculated as indicated below, was added to the IgG solution and incubated, while rotating, in the dark at RT for 1 hour. After labeling, unbound Alexa-647 was removed, using a PD-10 column (Amersham Biosciences, cat. no. 17-0851-01), with Tris buffer pH 8.0 (50 mM Tris [Trizma base, Sigma, cat. no. T-6066]; 100 mM NaCl [Riedel de Haen, cat. no. 31437]; 0.01% sodium azide [NaN$_3$, Riedel de Haen, cat. no. 13412]). The amount of Alexa-647 to be added to the IgG solution was calculated using the formula:

Volume Alexa-647 to be added (in μL)=(IgG conc (mg/mL)/MW IgG (Da)*ratio*volume*MW Alexa-647*1,000.

MW IgG=150,000 Da; ratio is the molar excess of Alexa-647 to be used; volume is the volume of the sample to be labeled (in mL); MW Alexa-647=1250 Da.

Protein concentration (IgG) and degree of labeling (D.O.L.) were determined by measuring OD 280 nm and 650 nm on an Ultrospec 2100 Pro (Amersham Biosciences). IgG concentration (mg/mL) was calculated using the formula:

IgG concentration=$[A_{280}-(0.03*A_{650})]$/IgG extinction coefficient.

D.O.L. was calculated using the formula:

D.O.L.=$A_{650}$/239,000/$[A_{280}-(0.03*A_{650})$/(IgG extinction coefficient*$MW$ IgG)].

239,000 is the extinction coefficient of Alexa-647 at $A_{max}$ in cm$^{-1}$M$^{-1}$; 0.03 is the correction factor ($A_{280}$ free dye/ $A_{max}$ free dye) (both provided by the manufacturer).

Bovine serum albumin (BSA; Sigma, cat. no. A 2934) was added from a 10% (w/v) solution to a final concentration of 0.1% (w/v) and labeled antibodies were stored at 5° C. In a few fusion screens, in addition to the anti-human IgG-Cy5.5, to detect human antibodies, an anti-mouse IgG Cy5.5-labeled conjugate was used, to detect specific chimeric antibodies. Samples were scanned using an Applied Biosystems 8200 Cellular Detection System (8200 CDS) and 'counts×fluorescence' was used as read-out.

Example 7

HuMab Hybridoma-Generation

HuMAb mice with sufficient (defined as above) antigen-specific titer development were sacrificed and the spleen and lymph nodes flanking the abdominal aorta and caval vein were collected. Fusion of splenocytes and lymph node cells to a mouse myeloma cell line was done by electrofusion using a CEEF 50 Electrofusion System (Cyto Pulse Sciences, Glen Burnie, Md., USA), essentially according to the manufacturer's instructions. Fused cells were seeded fusion medium containing 10% Fetal Clone I Bovine serum (Perbio), 1 mM sodium pyruvate (Cambrex), 0.5 U/mL penicillin, 0.5 U/mL streptomycin (Cambrex), 50 μM 2-mercaptoethanol (Invitrogen), 600 ng/mL interleukin 6 (IL-6) (Strathmann), 1×HAT (Sigma) and 0.5 mg/mL kanamycin (Invitrogen) in HyQ mADCF-Mab (Perbio). After ten days, supernatant was harvested and cells were refreshed with harvest medium, containing 10% Fetal Clone I Bovine serum, 0.5 U/mL penicillin, 0.5 U/mL streptomycin, 600 ng/mL IL-6 and 1×proHT (Cambrex) in HyQ mADCF-Mab. Supernatants of the hybridoma cultures were screened by primary FMAT screening assays on TC2013-CD74v1de12-36 cells and TC2013-CD74v2de12-36 cells to detect hybridomas producing human (or chimeric) anti-CD74 antibodies as described supra. The 60 best primary wells were seeded in semisolid medium made from 40% CloneMedia (Genetix, Hampshire, UK) and 60% HyQ 2×complete medium (Hyclone, Waltham, USA). From each primary well, two wells of a Genetix black 6-well plate were seeded. From each well, 33 sub clones were picked, using the ClonePix system (Genetix). The sub clones were picked in harvest medium. After seven days, the supernatants of the sub clones were screened again for CD74-specific human IgG binding and human IgG concentration was measured using Octet (Fortebio, Menlo Park, USA). From each primary well, the best sub clone was expanded in expansion medium containing only 600 ng/mL IL-6, 0.5 U/mL penicillin, 0.5 U/mL streptomycin and 1×proHT. The sub clones were expanded from one 96-well plate well to one 24-well plate well to four 24-well plate wells to six 6-well plate wells to Hyperflask (small scale production). Supernatants of the hyperflasks were screened for CD74-specific human IgG binding. Clones derived by this process were designated PC2013.

Example 8

Mass-Spectrometry of Purified Antibodies

Small aliquots of 0.8 mL antibody-containing supernatant from 6-well or Hyperflask stage were purified using PhyTip columns containing Protein G resin (PhyNexus Inc., San Jose, USA) on a Sciclone ALH 3000 workstation (Caliper Lifesciences, Hopkinton, USA). The PhyTip columns were used according to manufacturer's instructions, but buffers were replaced. PBS (B. Braun, Medical B.V., Oss, Netherlands) was used as Binding Buffer and 0.1M Glycine-HCl pH 2.7 (Fluka Riedel-de Haën, Buchs, Germany) was used as Elution Buffer. After purification, samples were neutralized with 2M Tris-HCl pH 9.0 (Sigma-Aldrich, Zwijndrecht, Netherlands). Alternatively, in some cases larger volumes of culture supernatant were purified using Protein A affinity column chromatography.

After purification, samples were placed in a 384-well plate (Waters, 100 uL square-well plate, art#186002631). Samples were de-glycosylated with N-glycosidase F (Roche cat no 11365177001) at 37° C., O/N. DTT (15 mg/mL) was added (1 μL/well) and incubated at 37° C. for 1 h. Samples (5 or 6 μL) were desalted on an Acquity UPLC™ (Waters, Milford, USA) with a BEH300 C18, 1.7 μm, 2.1×50 mm column at 60° C. MQ water and LC-MS grade acetonitrile (Biosolve, cat no 01204101, Valkenswaard, The Netherlands), both with 0.1% formic acid (Fluka, cat no 56302, Buchs, Germany), were used as Eluens A and B. Time-of-flight electrospray ionization mass spectra were recorded on-line on a micrOTOFT™ mass spectrometer (Bruker, Bremen, Germany) operating in the positive ion mode. Prior to analysis, a 900-3000 m/z scale was calibrated with ES tuning mix (Agilent Technologies, Santa Clara, USA). Mass spectra were deconvoluted with DataAnalysis™software v3.4 (Bruker) using the Maximal Entropy algorithm searching for molecular weights between 5 and 80 kDa.

After deconvolution the resulting heavy and light chain masses for all samples were compared in order to find duplicate antibodies. In the comparison of the heavy chains the possible presence of C-terminal lysine variants was taken into account. This resulted in a list of unique antibodies, where unique is defined as a unique combination of heavy and light chains. In case duplicate antibodies were found, results from other tests were used to decide which material was used to continue experiments with.

Mass spectrometry analysis of the molecular weights of heavy and light chains of 41 anti-CD74 hybridomas yielded 18 unique antibodies (unique heavy chain/light chain combination).

Example 9

Sequence Analysis of the CD74-Specific HuMab Variable Domains and Cloning in Expression Vectors Total RNA of the anti-CD74 HuMab antibodies was prepared from $5 \times 10^6$ hybridoma cells and 5'-RACE-Complementary DNA (cDNA) was prepared from 100 ng total RNA, using the SMART RACE cDNA Amplification kit (Clontech), according to the manufacturer's instructions. $V_H$ (variable region of heavy chain) and $V_L$ (variable region of light chain) coding regions were amplified by PCR. Amplified PCR products of antibodies 006, 008 and 011 were cloned into the pCR-Blunt II-TOPO vector (Invitrogen) using the Zero Blunt PCR cloning kit (Invitrogen).

Amplified $V_H$ and $V_L$ PCR products of antibody 005 were cloned in pcDNA3.3 vectors (Invitrogen) encoding G1f and Kappa constant domains. For each HuMab, 16 $V_L$ clones and 8 $V_H$ clones were sequenced. Clones with predicted heavy and light chain mass in agreement with the mass of the hybridoma-derived material of the same antibody (as determined by mass spectrometry) were selected for further study and expression. The resulting sequences are shown in the Sequence Listing and FIG. 2 herein.

Table 1 and Table 2 (below) give an overview of antibody sequence information and most homologous germline sequences.

TABLE 1

Heavy chain homologies

| Ab | V-GENE and allele | V-REGION identity, % (nt) | J-GENE and allele | D-GENE and allele | CDR-IMGT lengths |
|---|---|---|---|---|---|
| 005 | IGHV3-30-3*01 | 100.0 (288/288 nt) | IGHJ4*02 | IGHD3-10*01 | 8.8.17 |
| 006 | IGHV3-30-3*01 | 98.6 (284/288 nt) | IGHJ4*02 | IGHD3-16*02 | 8.8.17 |
| 008 | IGHV3-30-3*01 | 100.0 (288/288 nt) | IGHJ4*02 | IGHD3-16*02 | 8.8.17 |
| 011 | IGHV3-33*01 | 99.7 (287/288 nt) | IGHJ6*02 | IGHD3-10*01 | 8.8.16 |

TABLE 2

Light chain homologies

| Ab | V-GENE and allele | V-REGION identity % (nt) | J-GENE and allele | CDR-IMGT lengths |
|---|---|---|---|---|
| 005 | IGKV1D-16*01 | 99.6 (278/279 nt) | IGKJ4*01 | 6.3.9 |
| 006 | IGKV1D-16*01 | 100.0 (279/279 nt) | IGKJ4*01 | 6.3.9 |
| 008 | IGKV1D-16*01 | 100.0 (279/279 nt) | IGKJ4*01 | 6.3.9 |
| 011 | IGKV1D-16*01 | 100.0 (279/279 nt) | IGKJ4*01 | 6.3.9 |

TABLE 3

| References to the sequence listing: | |
|---|---|
| VH-region | |
| SEQ ID No: 7 | VH 005 |
| SEQ ID No: 8 | VH 005, CDR1 |
| SEQ ID No: 9 | VH 005, CDR2 |
| SEQ ID No: 10 | VH 005, CDR3 |
| SEQ ID No: 11 | VH 006 |
| SEQ ID No: 12 | VH 006, CDR1 |
| SEQ ID No: 13 | VH 006, CDR2 |
| SEQ ID No: 14 | VH 006, CDR3 |
| SEQ ID No: 15 | VH 008 |
| SEQ ID No: 16 | VH 008, CDR1 |
| SEQ ID No: 17 | VH 008, CDR2 |
| SEQ ID No: 18 | VH 008, CDR3 |
| SEQ ID No: 19 | VH 011 |
| SEQ ID No: 20 | VH 011, CDR1 |
| SEQ ID No: 21 | VH 011, CDR2 |
| SEQ ID No: 22 | VH 011, CDR3 |
| VL-region | |
| SEQ ID No: 23 | VL 005 |
| SEQ ID No: 24 | VL 005, CDR1 (=VL 011, VL 006, and VL 008 CDR1) |
| AAS | VL 005, CDR2 (=VL 011, VL 006, and VL 008 CDR2) |
| SEQ ID No: 25 | VL 005, CDR3 (=VL 011, VL 006, and VL 008 CDR3) |
| SEQ ID No: 26 | VL 006 = VL 008 = VL 011 |

Example 10

Purification of Antibodies

Culture supernatant was filtered over 0.2 μm dead-end filters, loaded on 5 mL Protein A columns (rProtein A FF, Amersham Bioscience) and eluted with 0.1 M citric acid-NaOH, pH 3. The eluate was immediately neutralized with 2M Tris-HCl, pH 9 and dialyzed to 12.6 mM $NaH_2PO_4$, 140 mM NaCl, pH 7.4 (B.Braun), O/N. After dialysis, samples were sterile-filtered over 0.2 μm dead-end filters. Purity was determined by SDS-PAGE and concentration was measured by nephelometry and absorbance at 280 nm. Purified antibodies were aliquoted and stored at −80° C. Once thawed, purified antibody aliquots were kept at 4° C. Mass spectrometry was performed to identify the molecular mass of the antibody heavy and light chains expressed by the hybridomas as described in Example 9.

Example 11

Binding of CD74-Specific HuMab Antibodies to Recombinant Extracellular Domain of two CD74 isoforms, Determined by ELISA, and to Cellular CD74 on Raji Cells, Determined by FACS Binding of anti-CD74 HuMab antibodies to two isoforms of CD74 was measured by ELISA (coated recombinant extracellular domain of CD74) and to cellular CD74 on Raji cells (ATCC, Manassas, Va.) by FACS analysis.

ELISA plates (Greiner BioOne) were coated 0/N at 4° C. with 2 µg/mL, 100 µL per well, recombinant CD74v1 or CD74v2 in PBS (B. Braun Melsungen AG). Sequences and production of the isoforms were described supra. ELISA wells were washed three times with PBS containing 0.05% Tween-20 (PBST), emptied, and blocked with 1% (w/v) BSA fraction V (Roche) in PBS at RT for 1 h while shaking (300 rpm), and emptied. Subsequently, 100 µL anti-CD74 HuMab antibodies were added in serial dilutions in 0.2% (w/v) BSA fraction V in PBST (assay buffer) and incubated while shaking at RT for 90 min. ELISA plates were washed three times with PBST, emptied, and bound HuMab antibodies were detected using HRP-conjugated goat-anti human IgG (100 µL; 1:5,000; Peroxidase Affinipure Goat anti-human IgG, F(ab')$_2$ Fragment Specific [min X Bov,Hrs, Ms Sr Prot]; Jackson Immunoresearch) in assay buffer and incubated while shaking at RT for 90 min. Plates were washed three times with PBST, emptied, and incubated with 100 µL ABTS solution (50 ml ABTS buffer [Roche] and one ABTS tablet [50 mg; Roche]). After incubation in the dark at RT for 30 min, the reaction was stopped by addition of 100 µL per well oxalic acid (2% [w/v]). Plates were measured at OD 405 nm in an ELISA reader (Biotek Instruments, EL808 Absorbance Microplate Reader).

For FACS analysis, $10^5$ cells in 100 µL FACS buffer (PBS supplemented with 0.1% BSA and 0.02% sodium azide) were seeded per well in 96-well round-bottom plates. Cells were spun down (1200 rpm, 4° C., 5 min) and supernatant was discarded. Serially diluted anti-CD74 HuMab antibodies were added (100 µL) and incubated on ice for 1 h. Cells were washed with FACS buffer, supernatants were discarded, and 100 µL of R-Phycoerythrin labeled goat anti-human IgG (R-Phycoerythrin AffiniPure F(ab')$_2$ Frag Gt Anti-Human IgG, Fcγ Frag Spec [min X Bov,Hrs,Ms Sr Prot]; Jackson Immunoresearch), diluted 1:100 in FACS buffer, was added. After 1 h on ice (in the dark), cells were washed once in FACS buffer, supernatant was discarded, and specific binding of the HuMab antibodies was detected by flow cytometry on a FACS Canto II (BD Biosciences).

Isotype control Ab IgG1-b12 was used as a negative control. Binding curves were analyzed using non-linear regression (sigmoidal dose-response with variable slope) using GraphPad Prism 5 software (GraphPad Software, San Diego, Calif., USA).

Figure 3B:
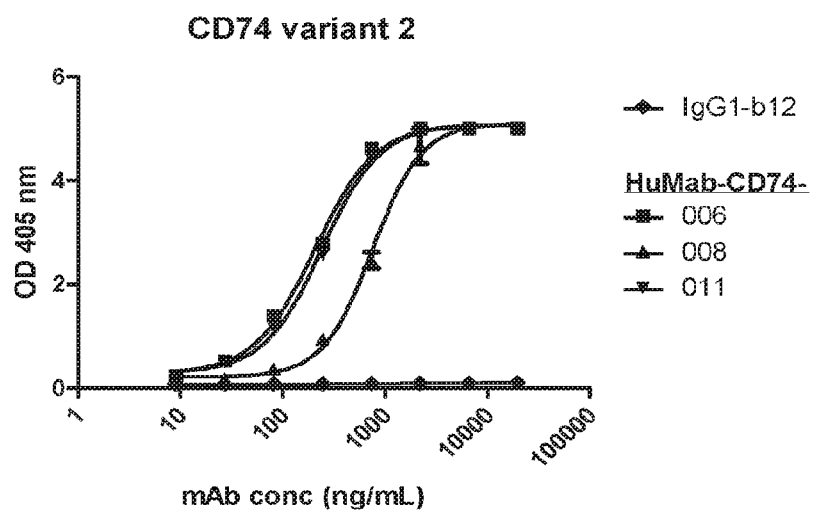

FIG. 3 shows that HuMab-CD74-006 and -011 bound with high affinity (EC$_{50}$ values between 210 and 344 ng/mL) to both isoforms of the CD74 extracellular domain. HuMab-CD74-008 bound with intermediate affinity (EC$_{50}$ between 759 and 1391 ng/mL) to both isoforms.

Figure 4:
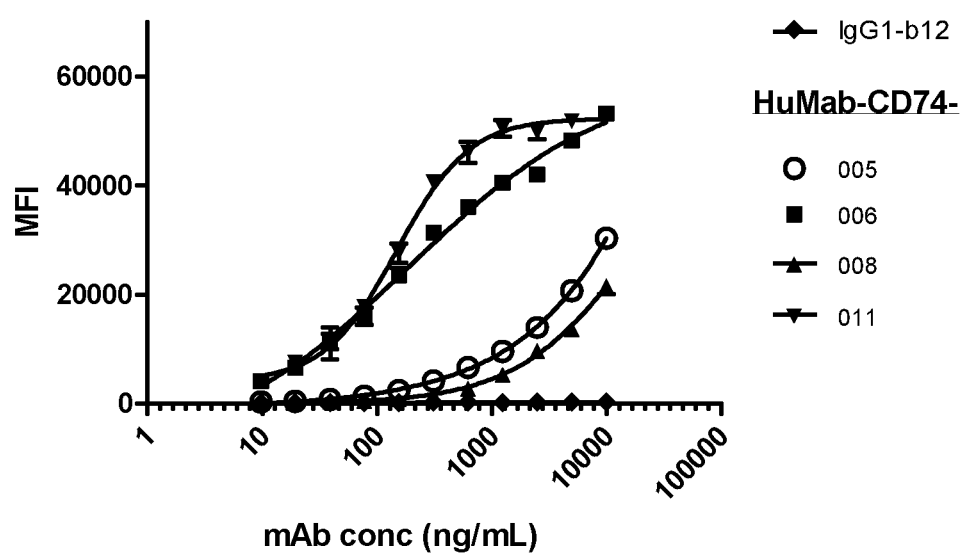
FIG. 4: Binding of CD74-specific antibodies to cellular CD74 on Raji cells, determined by FACS. All human antibodies were produced by transiently co-transfecting HEK-293F cells with relevant heavy and light chain expression vectors.

FIG. 4 shows that HuMab-CD74-006 and -011 also bound with high affinity (EC$_{50}$ between 150 and 200 ng/mL) to cellular CD74 expressed by Raji cells. HuMab-CD74-008 and -005 bound to cellular CD74 with intermediate affinity (EC$_{50}$ values could not be determined because maximum binding was not reached).

Table 4 shows EC$_{50}$ values of CD74-specific HuMab antibodies for binding to the extracellular domain of CD74v1 and CD74v2 by ELISA and to cellular CD74 by FACS on Raji cells.

TABLE 4

Overview of EC$_{50}$ values for binding of CD74 specific HuMab antibodies to the extracellular domain of CD74v1 and CD74v2, determined by ELISA, and to cellular CD74 on Raji cells, determined by FACS. All HuMab antibodies were produced by transiently co-transfecting HEK293F cells with relevant heavy and light chain expression vectors (as described supra).

| HuMab-CD74- | EC$_{50}$ (ELISA) CD74v1 | EC$_{50}$ (ELISA) CD74v2 | EC$_{50}$ (FACS) |
|---|---|---|---|
| 005 | nt | nt | nd |
| 006 | 321 | 210 | 196 |
| 008 | 1391 | 759 | nd |
| 011 | 344 | 245 | 151 |

EC$_{50}$ values are in ng/mL.
nd—could not be calculated.
nt—not tested.

Example 12

Cross-Reactivity of Anti-CD74 HuMab Antibodies to Cynomolgus Monkey Tissues

The capacity of CD74-specific HuMab antibodies to bind to cynomolgus CD74 was tested by immunohistochemistry. Immunohistochemistry with anti-CD74 HuMab antibodies was performed on frozen human tonsil and cynomolgus lymph node tissue, with anticipated CD74 expression on (follicular) B lymphocytes and macrophages. Frozen tissue sections were cut (4-6 µm thickness) and fixated in acetone. HuMab antibodies were complexed with fluorescein-isothiocyanate (FITC) by incubation with goat anti-human IgG (Fc)-FITC (Fab) (Protos) (1:1 ratio with Humab). Prior to HuMab staining (1 µg/mL), tissues were blocked for endogenous biotin, peroxidase (PO) and immunoglobulins. HuMab-Fab-FITC complex was detected by subsequent incubations with rabbit anti-FITC (Invitrogen) (diluted 1:1000) and PO-conjugated goat anti-rabbit IgG (Powervision, [rb IgG]-PO; undiluted). PO activity was visualized with amino-ethyl-carbazole (AEC) as substrate, resulting in a red color, and nuclei were visualized with hematoxylin (blue). Tissue-stainings were examined with light microscopy (Axioskop-2 plus), converted to digital pictures by an Axiocam-camera and stored as digital pictures.

Figure 5:
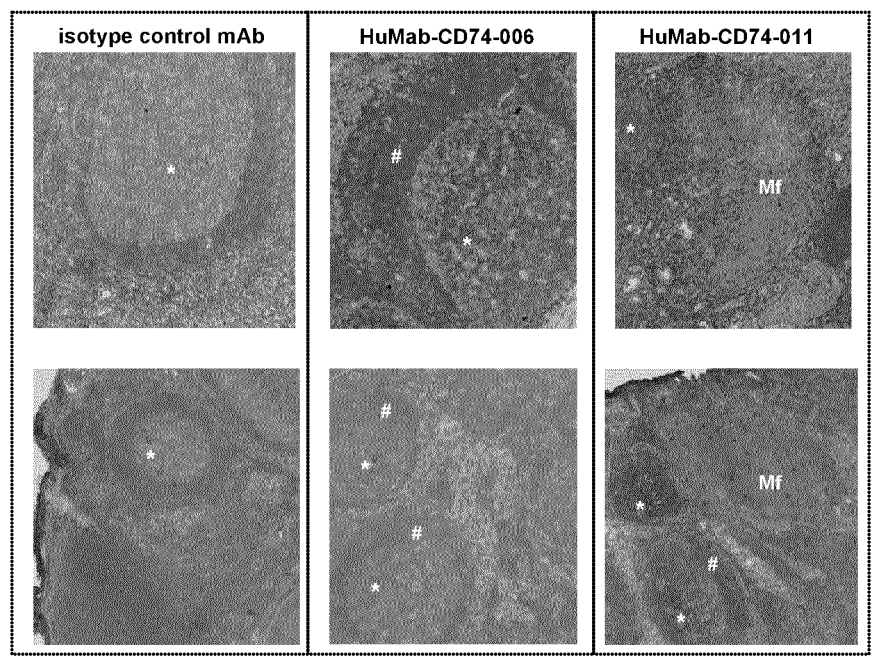
FIG. 5: Cross-reactivity of CD74-specific antibodies with cynomolgus CD74. Human tonsil (upper panel) and cynomolgus lymph nodes (lower panel) were stained with CD74-specific antibodies. *: germinal center; Mf: macrophages; #: Mantle zone B cells.

FIG. 5 shows that HuMab-CD74-006 and -011 showed cross-reactivity with cynomolgus CD74, as shown by staining of macrophages and follicular B cells (staining for isotype control is negative). The extent of cross-reactivity with cynomolgus CD74 was less for HuMab-CD74-006 than for -011, as shown by less intensive staining of cynomolgus tissue as compared with human tissue.

Example 13

Induction of ADCC and CDC

Induction of ADCC by CD74-specific HuMab antibodies was tested in a $^{51}$Cr release assay. Briefly, Raji cells were labeled with 100 pCi $^{51}$Cr and used as target cells. Peripheral blood mononuclear cells, isolated from buffy coats, were used as effector cells. Target cells were pre-incubated with anti-CD74 HuMab antibodies (RT, 30 min) and effector cells were added, resulting in an effector to target ratio of 100:1, and incubated at 37° C., 5% CO$_2$, O/N. $^{51}$Cr release in the supernatant was measured in a gamma counter. No significant induction of ADCC by anti-CD74 HuMab antibodies was detected.

Induction of CDC by anti-CD74 HuMab antibodies was tested using propidium iodide method. Briefly, Raji cells were pre-incubated with anti-CD74 HuMab antibodies (RT, 15 min) and normal human serum was added, to a final concentration of 20%, and incubated at 37° C., 5% $CO_2$ for 45 min. Plates were put on ice to stop the reaction. Propidium iodide was added and cells were analyzed by FACS analysis. No significant induction of CDC by anti-CD74 HuMab antibodies was detected.

Example 14

Antibody-Mediated Internalization and Cell Killing by Anti-CD74 HuMab Antibodies in an Anti-Kappa-ETA' Assay To evaluate the suitability of the anti-CD74 HuMab antibodies for an antibody-drug conjugate approach, a generic in vitro cell-based killing assay using kappa-directed *pseudomonas*-exotoxin A (anti-kappa-ETA') was developed. In this assay, a construct consisting of a high affinity anti-human kappa light chain domain antibody and a truncated form of the *pseudomonas*-exotoxin A plus a KDEL retention motif was used. Upon internalization, the anti-kappa-domain-antibody-ETA' construct undergoes proteolysis and disulfide-bond reduction, separating the catalytic and the binding domain. The catalytic domain is believed to be transported from the Golgi system to the endoplasmic reticulum via the KDEL retention motif, and subsequently translocated to the cytosol where it inhibits protein synthesis and induces apoptosis (Kreitman RJ. BioDrugs 2009; 23(1): 1-13).

Antibody-mediated internalization and cell killing by the toxin was tested for different anti-CD74 HuMab antibodies with Raji cells. The number of CD74 molecules expressed on the Raji cell surface was estimated to be $10^4$ molecules per cell, using QIFIKIT® method (Dako, Glostrup, Denmark). $10^4$ cells per well in cell culture medium were seeded in 96-well tissue culture plates (Greiner Bio-one). Plates were incubated at 37° C. for 1 h, to let cells settle down. To identify anti-CD74 HuMab antibodies that enable internalization of and killing by the toxin, a fixed concentration (1 μg/mL final concentration in the wells) of anti-kappa-ETA', that did not induce non-specific cell death in the absence of antibody, was pre-incubated for 30 min with a titrated amount of anti-CD74 HuMab antibodies before addition to the cells. After three days, the amount of viable cells was quantified with AlamarBlue (BioSource International, San Francisco, US), added in 10 μL per well according to the manufacturer's instructions. After incubation at 37° C. for 4 h, fluorescence was monitored using the EnVision 2101 Multilabel reader (PerkinElmer, Turku, Finland) with standard AlamarBlue settings. An isotype control antibody (IgG1-b12), pre-incubated with anti-kappa-ETA', was used as a negative control. Staurosporine (Sigma-Aldrich) was used as a control for determining background signal and added to cells at a final concentration of 1 μg/mL.

Percentage viability was calculated as follows:

$(FL_{treated} - FL_{background})/(FL_{control} - FL_{background}) \times 100\%$.

$FL_{control}$=fluorescence from untreated wells $FL_{background}$=fluorescence from staurosporine-treated wells.

Figure 6:
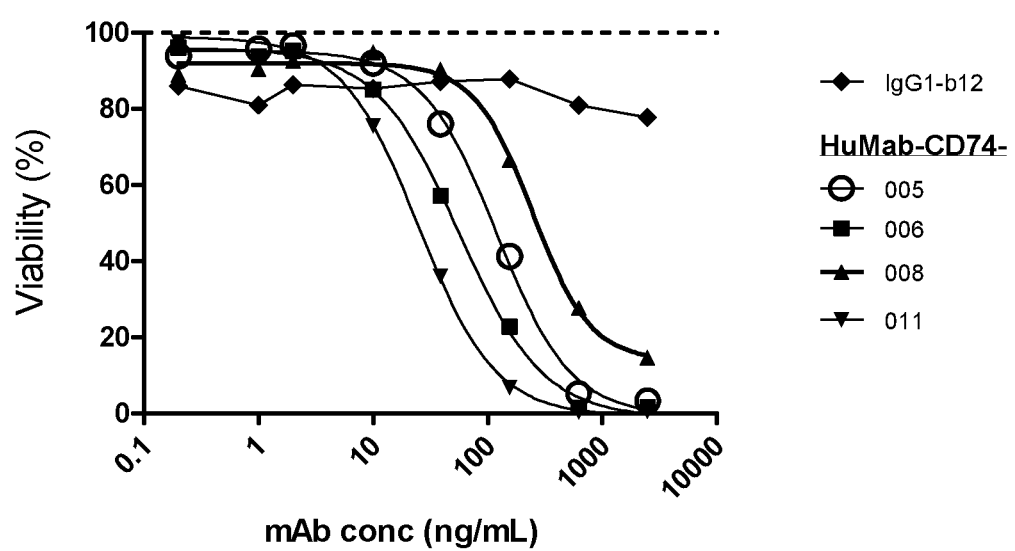
FIG. 6: Dose-dependent induction of cell killing by anti-kappa-ETA'-pre-incubated CD74-specific antibodies. A representative experiment is shown. Data shown are mean percentages viability of duplicate wells of cells treated with anti-kappa-ETA'-pre-incubated CD74 HuMab antibodies. Percentage viability was calculated as described in Example 14.

FIG. 6 and Table 5 show that all anti-kappa-ETA'-pre-incubated anti-CD74 HuMab antibodies were able to kill Raji cells in a dose-dependent manner. Anti-kappa-ETA' pre-incubated HuMab-CD74-006, -011, -005 and -008 induced efficient killing ($EC_{50}$ between 25 and 250 μg/mL and minimal percentage viability left between 0 and 15). Anti-kappa-ETA' pre-incubated control mAb IgG1-b12 did not induce cell killing.

TABLE 5

Overview of $EC_{50}$ values and percentages of cell viability left after treatment of Raji cells with anti-kappa-ETA'-pre-incubated anti-CD74 HuMab antibodies. Data shown are $EC_{50}$ values (in μg/mL) and minimal percentages viability of Raji cells treated with anti- kappa-ETA' pre-incubated anti-CD74 HuMab antibodies, measured in one representative experiment.

| Antibody (HuMab-CD74-) | % viability | $EC_{50}$ |
| --- | --- | --- |
| 005 | 3.24 | 120 |
| 006 | 1.50 | 57 |
| 008 | 14.65 | 247 |
| 011 | 0.47 | 25 |
| IgG1-b12 | 85.89 | n.d.[a] |

[a] Could not be calculated.

Example 15

Preparation of CD74-Specific ADCs

HuMab-CD74-005, HuMab-CD74-006, HuMab-CD74-011 and the negative control IgG1-b12 were produced transiently in HEK-293F cells. The antibodies were purified by Protein A chromatography according to standard procedures, finally yielding approximately 263 mg purified HuMab-CD74-005, 165 mg HuMab-CD74-006 and 720 mg HuMab-CD74-011. The amount of conjugated antibody obtained is shown in Table 6. The drug-linker vcMMAE or mcMMAF was alkylated to the cysteines of the reduced antibodies according to procedures described in literature (Sun et al. (2005) Bioconjugate Chem. 16: 1282-1290; McDonagh et al., (2006) Protein Eng. Design Sel. 19: 299-307; Alley et al., (2008) Bioconjugate Chem. 19: 759-765). The reaction was quenched by the addition of an excess of N-acetylcysteine. Any residual unconjugated drug was removed by diafiltration and the final CD74-specific antibody drug conjugates were formulated in PBS.

The CD74-specific antibody drug conjugates were subsequently analyzed for concentration (by absorbance at 280 nm), the drug-to-antibody ratio ('DAR') by reverse phase chromatography (RP-HPLC) and hydrophobic interaction chromatography (HIC), the amount of unconjugated drug (by reverse phase chromatography), the percentage aggregation (by size-exclusion chromatography, SEC-HPLC) and the endotoxin levels (by *Limulus Amebocyte* Lysate (LAL) endotoxin test). The results are shown in Table 7.

TABLE 6

Amount of ADC obtained

| HuMab-CD74- | Linker-drug | Amount of ADC (mg) |
| --- | --- | --- |
| 005 | vcMMAE | 94 |
| 005 | mcMMAF | 91 |
| 006 | vcMMAE | 63 |
| 006 | mcMMAF | 60 |
| 011 | vcMMAE | 276 |
| 011 | mcMMAF | 293 |
| b12 | vcMMAE | 174 |
| b12 | mcMMAF | 245 |

TABLE 7

Analysis of antibody-drug conjugates

| Assay | HuMab-CD74-005 | | HuMab-CD74-006 | | HuMab-CD74-011 | | IgG1-b12 | |
|---|---|---|---|---|---|---|---|---|
| | vcMMAE | mcMMAF | vcMMAE | mcMMAF | vcMMAE | mcMMAF | vcMMAE | mcMMAF |
| Concentration (mg/mL) | 7.2 | 6.4 | 6.4 | 6.2 | 8.2 | 8.1 | 6.6 | 9.1 |
| DAR by RP-HPLC | 3.9 | 3.9 | 4.0 | 3.7 | 3.8 | —* | 3.2 | 3.9 |
| DAR by HIC | 4.0 | 4.0 | 4.0 | 4.1 | 3.9 | 3.9 | 3.3 | 4.0 |
| % unconjugated drug | <0.5 | <0.5 | <0.5 | <0.5 | <0.5 | <0.5 | <0.5 | <0.5 |
| % aggregate by SEC-HPLC | 1.3 | 1.2 | 0.7 | 0.3 | 0.7 | 0.3 | 0.8 | 1.0 |
| Endotoxin (EU/mg) | 0.199 | 0.152 | 0.101 | 0.085 | 0.200 | 0.083 | 0.078 | 0.104 |

*DAR could not be assigned because of co-elution of peaks

Example 16

Binding of Anti-CD74 ADCs to Recombinant Extracellular Domain of CD74v1, Determined by ELISA Binding of CD74-specific ADCs to CD74 was measured by ELISA (coated recombinant extracellular domain of CD74v1) and compared with binding of unconjugated CD74-specific HuMab antibodies.

ELISA plates (Greiner BioOne) were coated with 2 µg/mL, 100 µL per well, recombinant CD74ECDHis in PBS (B. Braun Melsungen AG) at 4° C., 0/N. ELISA plates were emptied and blocked with 200 µL/well PBS containing 0.05% Tween-20 (PBST) while shaking (300 rpm), at RT for 1 hour, washed three times with 300 µL PBST and emptied. Subsequently, 100 µL anti-CD74 ADCs or unconjugated CD74-specific HuMab antibodies were added in serial dilutions in PBST and incubated while shaking at RT for 2 hours. ELISA plates were washed with PBST and emptied. Bound anti-CD74 ADCs and unconjugated HuMab antibodies were detected by addition of HRP-conjugated mouse-anti human IgG1 (100 µL; 0.015 µg/mL; Sanquin; # M1328) in PBST and incubation while shaking, at RT for 2 hours. Plates were washed with PBST, emptied and incubated with 100 µL ABTS solution (50 ml ABTS buffer [Roche] and one ABTS tablet [50 mg; Roche]). After incubation in the dark while shaking, at RT for 30 min, the reaction was stopped by incubation with 100 µL per well oxalic acid (2% [w/v]; Riedel de Haen) in the dark while shaking, for 10 min. Plates were measured at OD 405 nm in an ELISA reader (Biotek Instruments, EL808 Absorbance Microplate Reader).

IgG1-b12, an antibody binding to a non-related antigen, was used as a negative control (both unconjugated as well as in ADC format). Binding curves were analyzed by non-linear regression (sigmoidal dose-response with variable slope) using GraphPad Prism 5 software (GraphPad Software, San Diego, Calif., USA).

Figure 7A:
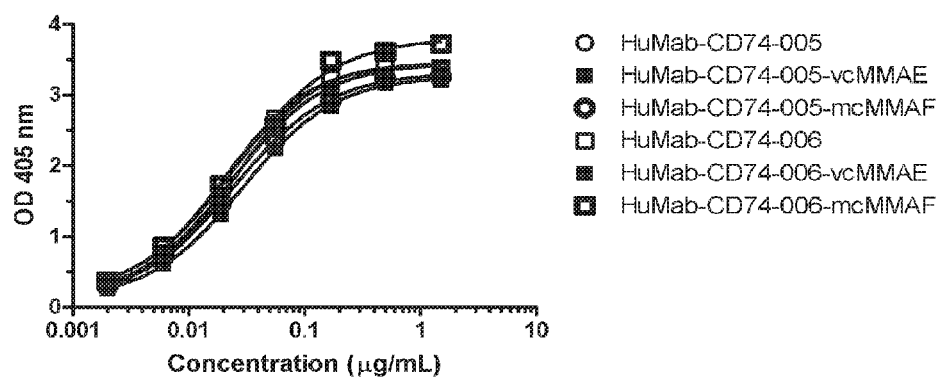
FIGS. 7A and 7B: Binding of CD74 HuMab antibodies 005 and 006 (FIG. 7A) and 011 (FIG. 7B) and the corresponding ADCs to recombinant protein of the CD74v1 extracellular domain, as determined by ELISA. One representative experiment is shown.
Figure 7B:
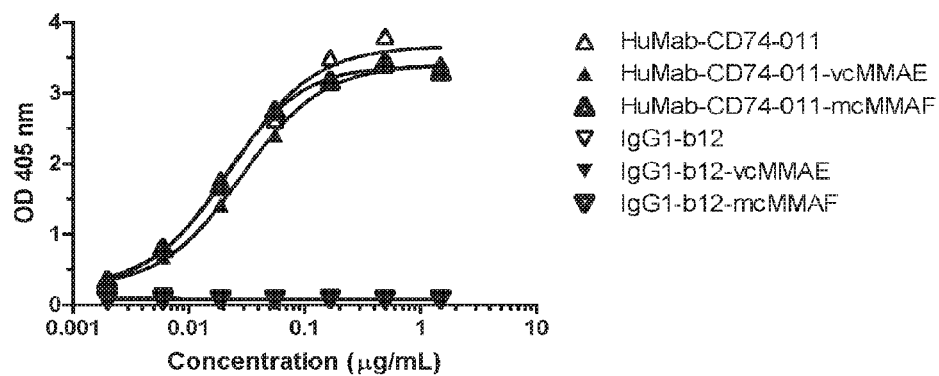

All anti-CD74 HuMab antibodies and ADCs bound within a similar range to the CD74v1 extracellular domain in an ELISA ($EC_{50}$ values between 0.02 and 0.04 µg/mL), as demonstrated by the binding curves in FIG. 7. Table 8 shows $EC_{50}$ values of CD74-specific HuMab antibodies and ADCs for binding to the extracellular domain of CD74.

TABLE 8

Overview of $EC_{50}$ values for binding of CD74-specific HuMab antibodies and ADCs to the extracellular domain of CD74v1, determined by ELISA. $EC_{50}$ values are in µg/mL. Data shown are mean $EC_{50}$ values calculated from four independent experiments.

| | $EC_{50}$ (ELISA) | | |
|---|---|---|---|
| HuMab-CD74- | Unconjugated | vcMMAE | mcMMAF |
| 005 | 0.03 | 0.04 | 0.04 |
| 006 | 0.02 | 0.03 | 0.02 |
| 011 | 0.02 | 0.03 | 0.02 |

Example 17

Binding of CD74-Specific ADCs to Surface-Expressed CD74, Determined by FACS Analysis on Daudi Cells Binding of anti-CD74 ADCs to surface-expressed CD74 was measured by FACS analysis on Daudi cells and compared with binding of unconjugated anti-CD74 HuMab antibodies.

$1 \times 10^5$ Daudi cells in 100 µL PBS containing 0.1% bovine serum albumin (BSA) (Roche, cat. no. 10735086001) and 0.02% sodium azide (Sigma-Aldrich, cat. no. 13412) (FACS buffer) were seeded per well in 96-well round-bottom plates (Greiner bio-one, cat. no. 650101). Cells were spun down (1200 rpm, 4° C., 3 min) and supernatant was discarded. Serially diluted anti-CD74 HuMab antibodies or ADCs were added (100 µL) and incubated on ice for 30 min. Cells were washed twice with 150 µL FACS buffer and 100 µL rabbit anti-human IgG-FITC (cat. nr. F0185, Dako), diluted 1:100 in FACS buffer, was added. After 30 min on ice (in the dark), cells were washed twice in 150 µL FACS buffer and specific binding of the HuMab antibodies and ADCs was detected by flow cytometry on a FACS Canto II (BD Biosciences).

Isotype control antibody IgG1-b12, an antibody binding to a non-related antigen, was used as a negative control (both unconjugated and as an ADC). Binding curves were analyzed using non-linear regression (sigmoidal dose-response with variable slope) using GraphPad Prism 5 software (GraphPad Software, San Diego, Calif., USA).

Figure 8A:
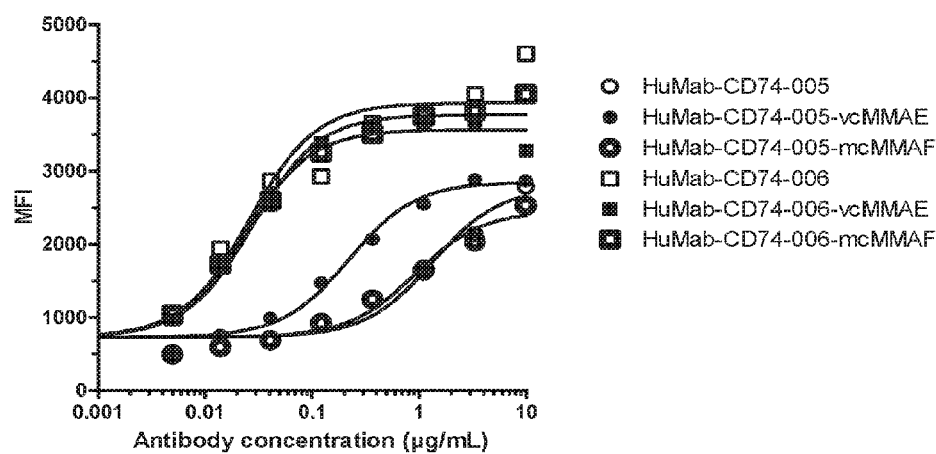
FIGS. 8A and 8B: Binding of CD74 HuMab antibodies 005 and 006 (FIG. 8A) and 011 (FIG. 8B) and the corresponding ADCs to surface-expressed CD74, determined by FACS analysis on Daudi cells. Data shown are mean fluorescence intensities (MFI), calculated from three independent experiments.
Figure 8B:
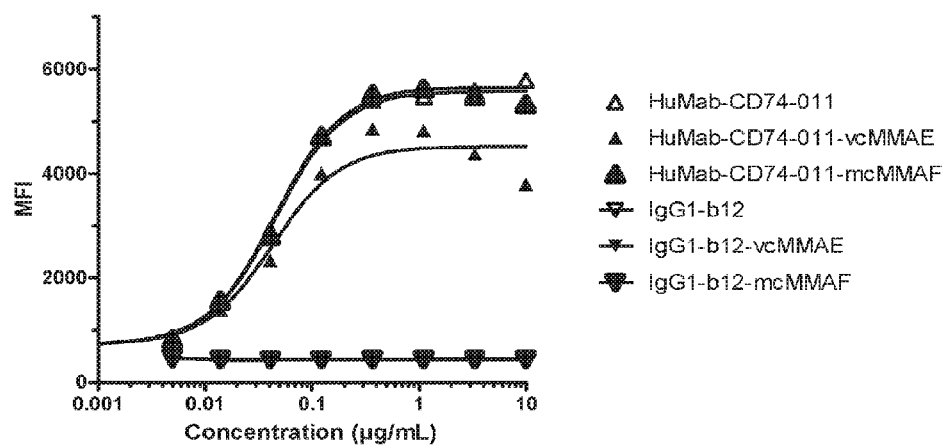
Figure 9A:
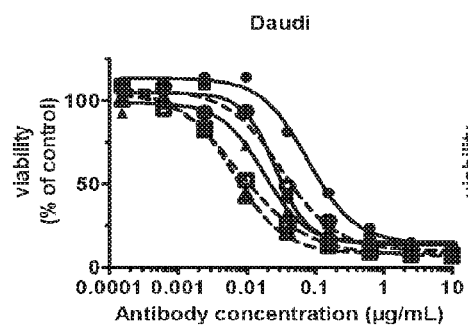
FIGS. 9A-9D: Dose-dependent induction of cell killing by CD74-specific ADCs. One representative experiment is shown for each of the following cell lines: Daudi (FIG. 9A), Raji (FIG. 9B), M4A4 (FIG. 9C) and NCI-H747 (FIG. 9D) cells. Data shown are percentages survival of duplicate wells of cells treated with CD74-specific ADCs.
Figure 9B:
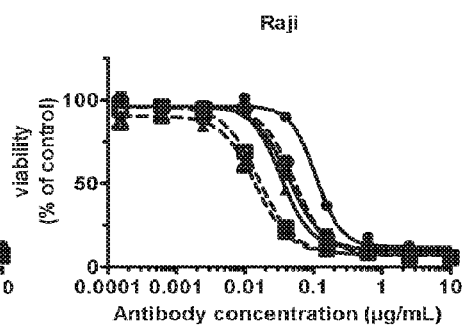
Figure 9C:
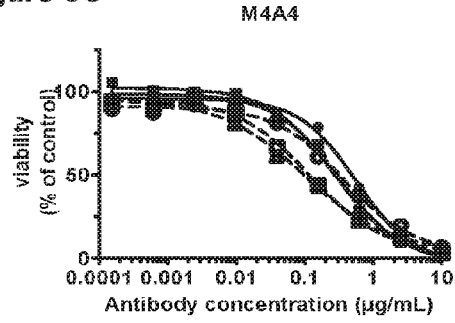
Figure 9D:
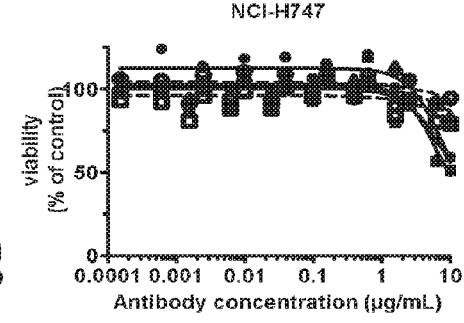

FIG. 8 shows binding curves and Tables 9 and 10 show $EC_{50}$ values and maximal mean fluorescence intensities for binding to surface-expressed CD74 of anti-CD74 HuMab antibodies and ADCs. All but one conjugated anti-CD74 HuMab antibodies bound to surface-expressed CD74 on Daudi cells with an affinity similar to the corresponding unconjugated HuMab antibodies. The vcMMAE-conjugate of HuMab-CD74-005 bound with higher affinity (lower $EC_{50}$ value) than the unconjugated HuMab. HuMab-CD74-005 and its mcMMAF-conjugate bound with lower affinity than HuMab-CD74-006 and -011 and their conjugates. Maximal binding was lower for vcMMAE-conjugated HuMab-CD74-006 and -011 than for the corresponding unconjugated HuMab antibodies.

TABLE 9

Overview of $EC_{50}$ values for binding of CD74-specific HuMab antibodies and ADCs to surface-expressed CD74, determined by FACS analysis on Daudi cells. $EC_{50}$ values are in μg/mL. Data shown are mean $EC_{50}$ values calculated from three independent experiments.

| HuMab-CD74- | $EC_{50}$ (FACS) | | |
|---|---|---|---|
| | Unconjugated | vcMMAE | mcMMAF |
| 005 | 1.27 | 0.26 | 1.05 |
| 006 | 0.04 | 0.03 | 0.03 |
| 011 | 0.05 | 0.05 | 0.05 |

TABLE 10

Overview of mean fluoresencence intensities at 10 μg/mL of CD74-specific HuMab antibodies and ADCs, determined by FACS analysis on Daudi cells. Data shown are mean maximal MFI values as measured at 10 μg/mL of HuMab-CD74 mAbs and ADCs. Mean maximal MFI values were calculated from three independent experiments.

| HuMab-CD74- | Maximal binding (FACS) | | |
|---|---|---|---|
| | Unconjugated | vcMMAE | mcMMAF |
| 005 | 2784 | 2863 | 2526 |
| 006 | 4599 | 3277 | 4050 |
| 011 | 5782 | 3791 | 5330 |

Example 18

Antibody-Mediated Internalization and Cell Killing by Anti-CD74 ADCs in an In Vitro Killing Assay To determine the capacity of anti-CD74 ADCs to induce cytotoxicity, an in vitro cell-based killing assay was performed.

Cell killing of four cell lines was tested for the different anti-CD74 ADCs. All cell lines were obtained from American Tissue Culture Collection (ATCC, Manassas, Va., USA): Raji (cat. no. CCL-86), Daudi (cat. no. CCL-213), M4A4 (cat. no. CRL-2914; derived from the human cell line MDA MB 435) and NCI-H747 cells (cat. no. CCL-252, derived from colorectal adenocarcinoma metastasis). Cells were seeded in optimal concentration (Raji: $1 \times 10^4$ cells/well; Daudi: $1 \times 10^3$ cells/well, M4A4: $2 \times 10^3$ cells/well, NCI-H747 $3 \times 10^3$ cells/well) in 100 μL cell culture medium (for Daudi and Raji; RPMI 1640 [Lonza, cat. no. BE12-115F] supplemented with 10% Cosmic Calf Serum [Perbio Science Nederland B.V., cat. no. SH30087.04], 2 mM L-glutamin [Lonza, cat. no. BE17-605F] and 1 mM Sodium Pyruvate [Lonza, cat. no. BE13-115E]; for NCI-H747: RPMI 1640 supplemented with 10% Cosmic Calf Serum, 1 mM Sodium Pyruvate, 0.15% Sodium Bicarbonate [Lonza, cat. no. BE17-613E] and 0.5% Glucose [Sigma, cat. no. G8769]; and for M4A4: DMEM [Lonza, cat. no. BE12-709F] supplemented with 10% Cosmic Calf Serum) in 96-well tissue culture plates (Greiner Bio-one) and allowed to adhere. Serial dilutions of anti-CD74 ADCs were added and incubated at 37° C. for three (Raji, Daudi) or five (M4A4, NCI-H747) days. The amount of viable cells was quantified with AlamarBlue (cat. nr. DAL1100, BioSource International, San Francisco, US), according to the manufacturer's instructions. Fluorescence was monitored using the EnVision 2101 Multilabel reader (PerkinElmer, Turku, Finland) with standard AlamarBlue settings. IgG1-b12 (an antibody binding to a non-related antigen) ADCs were used as negative controls. Staurosporine (Sigma, # S6942) was used to induce maximal cell killing. The amount of CD74 molecules on cell lines was determined by QIFIKIT® (Dako, Glostrup, Denmark), according to the manufacturer's instructions, using mouse IgG1 anti-CD74 (clone By2; Santa Cruz, cat. no. SC-20062) and isotype control (CLB, cat. no. M1415) antibody. Both antibodies were used at a concentration of 10 μg/mL. It was determined that Raji and Daudi cells express ~20,000; and M4A4 cells ~11,000 CD74 molecules on the cell surface.

FIG. 9 and Table 11 show that all anti-CD74 ADCs were able to kill Raji, Daudi and M4A4 cells in a dose-dependent manner. $IC_{50}$ values for all conjugates were about 5-12 times higher on M4A4 cells (i.e. lower efficacy), expressing about six-fold lower levels of CD74. NCI-H747 cells were only killed at the highest dose of ADCs tested (10 μg/mL). For HuMab-CD74-006 and -011 mcMMAF conjugates were slightly more efficient in inducing killing of Daudi and Raji cells than vcMMEA conjugates (-006: on Daudi cells three-fold lower and on Raji cells five-fold lower $IC_{50}$; -011: on Daudi cells two-fold lower and on Raji cells four-fold lower $IC_{50}$).

TABLE 11

Overview of $IC_{50}$ values and percentages of cell killing induced by anti-CD74 ADCs. Data shown are mean $IC_{50}$ values (in μg/mL) and mean maximal percentages kill (at a concentration of 10 μg/mL) of the indicated cell lines treated with anti-CD74 ADCs. Data were calculated from three independent experiments. Percentage of cell killing (% kill) was calculated as follows:
$(MFI_{untreated} - MFI_{anti-CD74\ ADC-treated})/(MFI_{untreated} - MFI_{stauroporine-treated}) \times 100\%$.

| ADC | Raji | | Daudi | | M4A4 | | NCI-H747 | |
|---|---|---|---|---|---|---|---|---|
| | % kill | $IC_{50}$ | % kill | $IC_{50}$ | % kill | $IC_{50}$ | % kill | $IC_{50}$ |
| 005-vcMMAE | 88 | 0.11 | 85 | 0.08 | 100 | 0.56 | 41 | 7.48 |
| 005-mcMMAF | 92 | 0.05 | 90 | 0.03 | 97 | 0.38 | 5 | N.A.[a] |
| 006-vcMMAE | 90 | 0.05 | 85 | 0.03 | 100 | 0.28 | 49 | 6.12 |
| 006-mcMMAF | 93 | 0.01 | 93 | 0.01 | 97 | 0.12 | 21 | N.A.[a] |

TABLE 11-continued

Overview of IC$_{50}$ values and percentages of cell killing induced by anti-CD74 ADCs. Data shown are mean IC$_{50}$ values (in μg/mL) and mean maximal percentages kill (at a concentration of 10 μg/mL) of the indicated cell lines treated with anti-CD74 ADCs. Data were calculated from three independent experiments. Percentage of cell killing (% kill) was calculated as follows:
(MFI$_{untreated}$ − MFI$_{anti-CD74\ ADC-treated}$)/(MFI$_{untreated}$ − MFI$_{staurosporine-treated}$) × 100%.

|  | Raji | | Daudi | | M4A4 | | NCI-H747 | |
|---|---|---|---|---|---|---|---|---|
| ADC | % kill | IC$_{50}$ | % kill | IC$_{50}$ | % kill | IC$_{50}$ | % kill | IC$_{50}$ |
| 011-vcMMAE | 89 | 0.04 | 86 | 0.02 | 100 | 0.32 | 40 | 7.91 |
| 011-mcMMAF | 92 | 0.01 | 92 | 0.01 | 96 | 0.10 | 17 | N.A.[a] |

[a]Could not be calculated since plateau level of curve was not reached.

Example 19

Therapeutic Treatment of Daudi Tumor Xenografts in SCID Mice with CD74-Specific ADCs The in vivo efficacy of HuMab-CD74-011 ADCs was determined in established intravenous (i.v.) Daudi (Burkitt's lymphoma) xenograft tumors in SCID mice.

Daudi cells were transfected by electroporation with gWIZ luciferase (Aldevron, Fargo, N. Dak., USA) and pPur vector (BD Biosciences, Alphen a/d Rijn, The Netherlands) in a 4:1 ratio. After 48 h, puromycin was added for selection of a stably transfected clone (Daudi-luc). Daudi-luc #1E3 cells were cultured in RPMI supplemented with 10% cosmic calf serum (cat. no. SH30087.04, Hyclone), 1% penicillin/streptomycin (cat. no. DE17-603, Cambrex, Germany), 1% sodium pyruvate and 1 μg/mL puromycin (cat. no. P-8833, Sigma, Zwijndrecht, The Netherlands). 2.5×10$^6$ Daudi-luc tumor cells in 100 μL PBS were injected i.v. in the tail vein of female SCID mice. Mice were imaged directly after tumor inoculation, followed by imaging at weekly intervals starting on day 14. For imaging, mice were anesthetized using isoflurane, followed by intraperitoneal (i.p.) administration of 2.5 mg D-luciferin (acid form, cat.no. BT11-1000; Biothema, Haninge, Sweden) in 200 μL 10 mg/mL TRIS (cat. no. T60666-1 kg, Sigma). Bioluminescence imaging (BLI), from the back side (dorsal view), started 10 min after administration of D-luciferin, 5 min exposure time, on a Biospace Imager. Black and white images were made for anatomical reference. Mice were treated twice weekly with 60 μg (~3 mg/kg) HuMab-CD74-011 and control antibody (IgG1-b12), both as ADC and as unconjugated IgG1, in 100 μL PBS from day 21 after tumor inoculation, four times in total. Before treatment, mice were divided in groups of seven mice each, each group having equal average BLI signals and equal variances.

Figure 10:
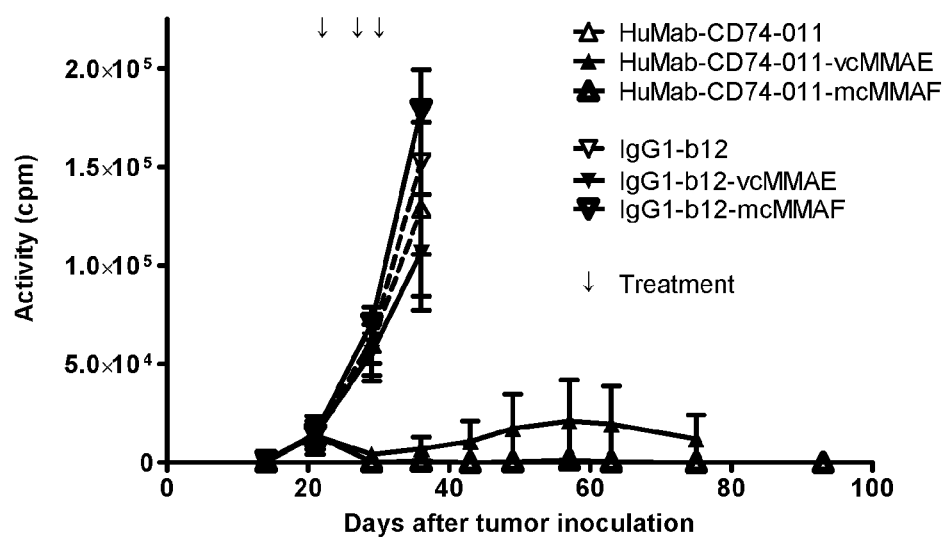
FIG. 10: In vivo efficacy of CD74-specific ADCs in therapeutic treatment of Daudi-luc xenografts in SCID mice. Mice with established Daudi-luc tumors were treated with CD74-specific ADCs. Data shown are mean bioluminescence imaging (BLI) signals±S.E.M. per group (n=7 mice per group).

FIG. 10 shows that both HuMab-CD74-011-vcMMAE and -mcMMAF were effective in reducing the size of i.v. Daudi-luc tumors. As shown in FIG. 10, there was an apparent tendency for a higher tumor growth inhibition in the case of unconjugated HuMab-CD74-011 as compared to the control antibody group, although the differences were not significant.

Example 20

Therapeutic Treatment of Raji Tumor Xenografts in SCID Mice with Anti-CD74 ADCs

The in vivo efficacy of anti-CD74 ADCs was also determined in an i.v. Raji xenograft tumor model in SCID mice.

Raji cells were transfected by electroporation with gWIZ luciferase (Aldevron, Fargo, N. Dak., USA) and pPur vector (BD Biosciences, Alphen a/d Rijn, The Netherlands) in a 4:1 ratio. After 48 h, puromycin was added for selection of a stably transfected clone (Raji-luc). Raji-luc #2D1 cells were cultured in RPMI supplemented with 10% cosmic calf serum (cat. no. SH30087.04, Hyclone), 1% penicillin/streptomycin (cat. no. DE17-603, Cambrex, Germany), 1% sodium pyruvate and 1 μg/mL puromycin (cat. no. P-8833, Sigma, Zwijndrecht, The Netherlands). 2.5×10$^6$ Raji-luc tumor cells in 100 μL PBS were injected i.v. in the tail vein of female SCID mice. Mice were imaged directly after tumor inoculation, followed by imaging twice weekly from day 7 onwards. For imaging, mice were anesthetized using isoflurane, followed by i.p. administration of 2.5 mg D-luciferin (acid form, cat. no. BT11-1000; Biothema, Haninge, Sweden) in 200 μL 10 mg/mL TRIS (cat. no. T60666-1 kg, Sigma). Bioluminescence imaging (BLI), from the back side (dorsal view), started 10 min after administration of D-luciferin, 5 min exposure time, on a Biospace Imager. Black and white images were made for anatomical reference. Mice were treated twice weekly with 60 μg (~3 mg/kg) HuMab-CD74-011 or control antibody (IgG1-b12), both as ADC and as unconjugated IgG, in 100 μL PBS, from day 11 after tumor inoculation, four times in total. Before treatment, mice were divided in groups of seven mice each, each group having equal average BLI signals and equal variances.

Figure 11:
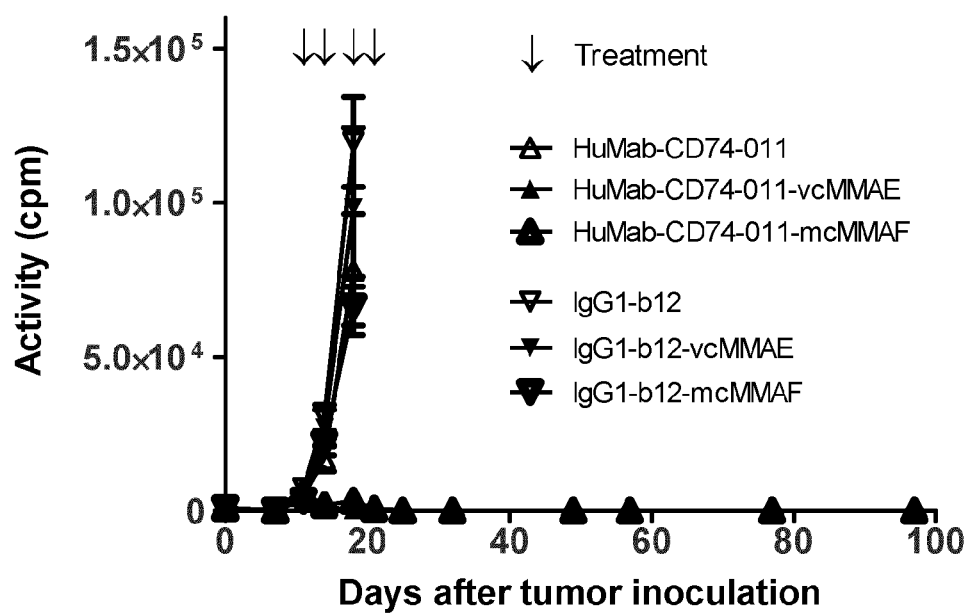
FIG. 11: In vivo efficacy of CD74-specific ADCs in therapeutic treatment of Raji-luc xenografts in SCID mice. Mice with established Raji-luc tumors were treated with CD74-specific ADCs. Data shown are mean BLI signals±S.E.M. per group (n=7 mice per group).

FIG. 11 shows that both HuMab-CD74-011-vcMMAE and -mcMMAF eliminated virtually all Raji-luc tumors. As shown in FIG. 11, there was an apparent tendency for a higher tumor growth inhibition in the case of unconjugated HuMab-CD74-011 as compared to the control antibody group, although the differences were not significant.

Example 21

Therapeutic Treatment of Raji Tumor Xenografts in SCID Mice with Anti-CD74 ADCs

The in vivo efficacy of anti-CD74 ADCs was also determined in established subcutaneous (s.c.) Raji (Burkitt's lymphoma) xenograft tumors in SCID mice.

5×10$^6$ Raji-luc #2D1 tumor cells (obtained as described Example 20) in 200 μL PBS were injected s.c. in the right flank of female SCID mice, followed by two injections with anti-CD74 ADCs or controls (IgG1-b12; both as ADC and as unconjugated IgG1), one when tumor sizes were on average ~400 mm$^3$, on day 17, and the other four days later, on day 21 (per injection 60 μg/mouse, ~3 mg/kg, in 100 μL, intraperitoneally). Before the first treatment, mice with tumor growth were divided into groups with equal tumor volume distribution. Tumor volume was determined at least two times per week. Tumor volumes (mm$^3$) were calculated from caliper (PLEXX) measurements as: 0.52×(length)× (width).

Figure 12:
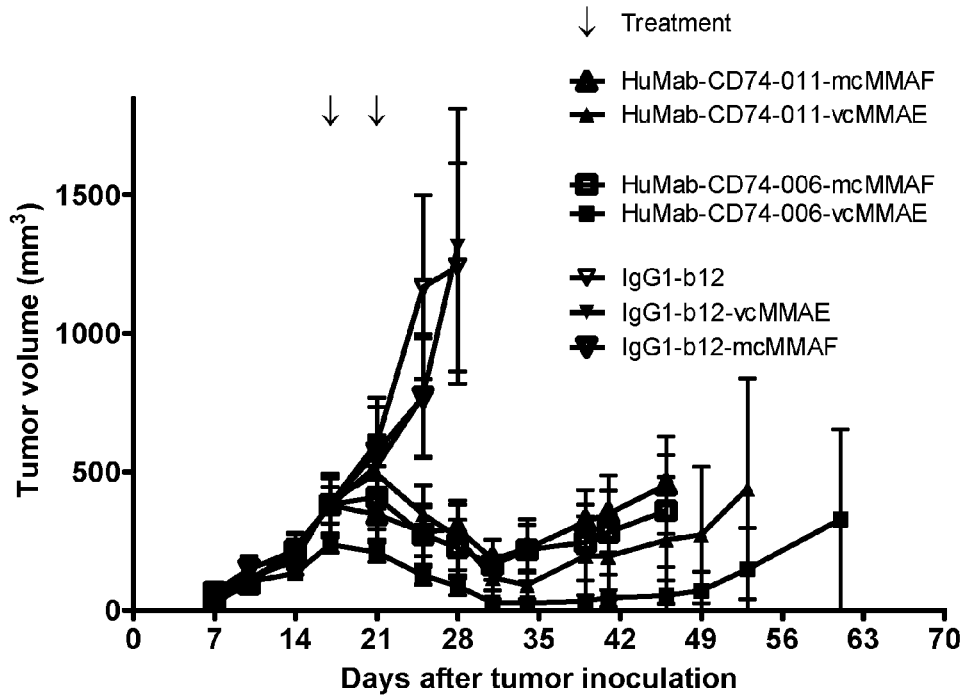
FIG. 12: In vivo efficacy of CD74-specific ADCs in therapeutic treatment of Raji xenografts in SCID mice. Mice with established s.c. Raji tumors were treated with CD74-specific ADCs. Data shown are mean tumor volumes±S.E.M. per group (n=6 mice per group).

FIG. 12 shows that all anti-CD74 ADCs effectively reduced the size of established s.c. Raji-luc tumors. Tumors in mice treated with IgG1-b12, both as ADC and unconjugated, continued to grow.

Example 22

Therapeutic Treatment of M4A4 Tumor Xenografts in SCID Mice with Anti-CD74 ADCs

The in vivo efficacy of anti-CD74 ADCs was also determined in established subcutaneous (s.c.) M4A4 xenograft tumors in SCID mice. M4A4 melanoma cells (cat. no. CRL-2914; American Tissue Culture Collection, ATCC; derived from the human cell line MDA-MB-435) were cultured in DMEM (cat. no. BE12-709F, Cambrex, Germany) containing 10% cosmic calf serum (cat. no. SH30087.04, Hyclone, The Netherlands) and 1% penicillin/streptomycin (cat. no. DE17-603, Cambrex, Germany). $10^7$ M4A4 tumor cells in 200 μL PBS were injected s.c. in the right flank of female SCID mice, followed by four injections with anti-CD74 ADCs or controls (IgG1-b12; both as ADC and as unconjugated IgG1), starting when tumor sizes were ~200 mm$^3$: day 11, day 14, day 18 and day 21 (per injection 60 μg/mouse, ~3 mg/kg, in 100 μL, intraperitoneally). Before the first treatment, mice were divided in groups with equal average tumor volume and equal variance in tumor volume. Tumor volume was determined at least two times per week. Tumor volumes (mm$^3$) were calculated from caliper (PLEXX) measurements as: 0.52×(length)×(width).

Figure 13:
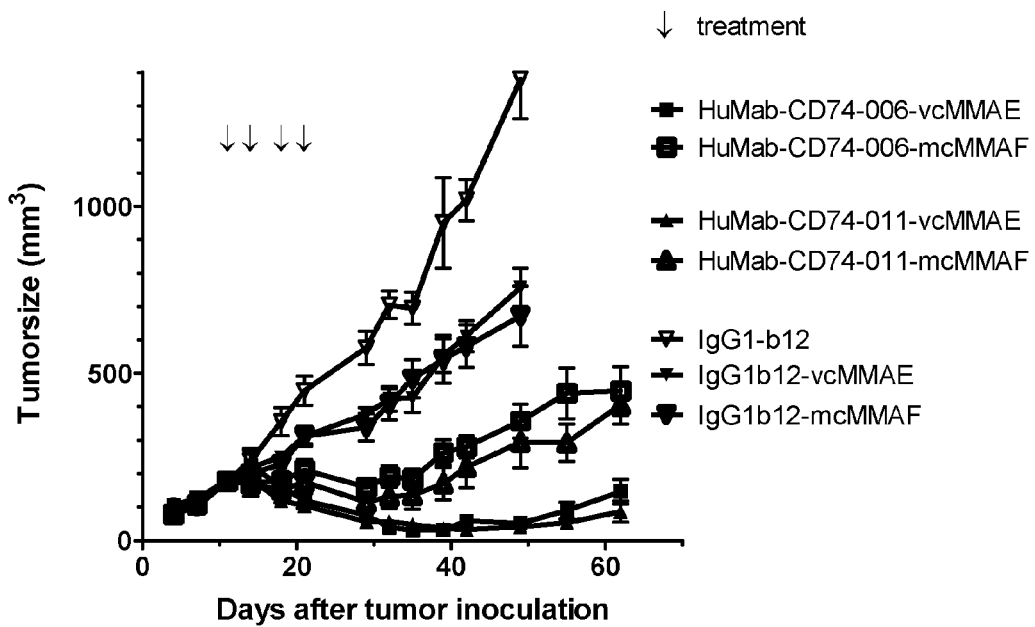
FIG. 13: In vivo efficacy of anti CD74 ADCs in therapeutic treatment of M4A4 xenografts in SCID mice. Mice with established M4A4 tumors were treated with anti CD74 ADCs. Data shown are mean tumor volumes±S.E.M. per group (n=7 mice per group).

FIG. 13 shows that, whereas all anti-CD74 ADCs inhibited tumor growth of established s.c. M4A4 tumors, the vcMMAE conjugates strongly reduced the tumor size. Compared with unconjugated IgG1-b12, the ADCs of IgG1-b12 slightly inhibited tumor growth.

Example 23

Determination of the Off-Rate of Anti-CD74 HuMab Antibodies on Daudi Cells

This Example describes determination of the off-rates of anti-CD74 HuMab antibodies in binding to Daudi cells.

Antibodies were labeled with Alexa Fluor® 488 Dye (Molecular Probes), hereinafter "Alexa-488", using the following procedure:

An antibody solution of 1 mg/mL IgG was prepared in 0.1 M sodium carbonate buffer pH 9.0 (NaHCO$_3$, Riedel de Haen, cat. no. 31437). Alexa-488 was prepared freshly, by adding 100 μL DMSO (Sigma, cat. no. D2438) to one vial (Alexa Fluor® 488 carboxylic acid, succinimidyl ester (1 mg/vial), Molecular Probes, Leiden, The Netherlands, cat. no. A-20000). A 25-times molar excess of Alexa-488, calculated as indicated below, was added to the IgG solution and incubated, while rotating, in the dark at RT for 1 hour. After labeling, unbound Alexa-488 was removed, using a PD-10 column (Amersham Biosciences, cat. no. 17-0851-01), with Tris buffer pH 8.0 (50 mM Tris [Trizma base, Sigma, cat. no. T-6066]; 100 mM NaCl [Riedel de Haen, cat. no. 31437]; 0.01% sodium azide [NaN$_3$, Riedel de Haen, cat. no. 13412]). The amount of Alexa-488 to be added to the IgG solution was calculated using the formula:

Volume Alexa-488 to be added (in μL)=(IgG conc (mg/mL)/MW IgG (Da)*ratio*volume*MW Alexa-488*100.

MW IgG=150,000 Da; ratio is the molar excess of Alexa-488 to be used; volume is the volume of the sample to be labeled (in mL); MW Alexa-488=643 Da.

Protein concentration (IgG) and degree of labeling (D.O.L.) were determined by measuring OD 280 nm and 495 nm on an Ultrospec 2100 Pro (Amersham Biosciences). IgG concentration (mg/mL) was calculated using the formula:

IgG concentration=[$A_{280}$−(0.11*$A_{495}$)]/IgG extinction coefficient.

D.O.L. was calculated using the formula:

D.O.L.=$A_{495}$/71,000/[$A_{280}$−(0.11*$A_{495}$)/(IgG extinction coefficient*MW IgG)].

71,000 is the extinction coefficient of Alexa-488 at $\lambda_{max}$ in cm$^{-1}$M$^{-1}$; 0.11 is the correction factor ($A_{280}$ free dye/$A_{max}$ free dye) (both provided by the manufacturer).

Bovine serum albumin (BSA; Sigma, cat. no. A 2934) was added from a 10% (w/v) solution to a final concentration of 0.1% (w/v) and labeled antibodies were stored at 5° C.

Daudi cells were incubated with Alexa-488-labeled anti-CD74 HuMab antibodies. Daudi cells were washed twice with ice cold PBS. $10^5$ cells per well in ice-cold FACS buffer were seeded in 96-well round-bottom tissue culture plates (Greiner Bio-one). 0.5 μg/mL (HuMab-CD74-006 and -011; final concentration) or 1 μg/mL (HuMab-CD74-008; final concentration) Alexa-488-labeled anti-CD74 HuMab was added in ice-cold FACS buffer. After incubation on ice for 30 min, 50 μg/mL (HuMab-CD74-006 and -011; final concentration) or 100 μg/mL (HuMab-CD74-008; final concentration) unlabeled anti-CD74 HuMab was added and incubated on ice for different time intervals ranging from 15 to 180 min. Total incubation time with unlabeled antibody is indicated below the graphs. To determine maximal binding, Daudi cells were incubated with Alexa-488-labeled HuMab antibodies on ice for 30 min. As a negative control, cells were incubated with isotype control antibody IgG1-b12 (0.5 μg/mL final concentration), followed by unlabeled IgG1-b12 (50 μg/mL final concentration). After antibody incubation, cells were washed once in FACS buffer and bound Alexa-labeled anti-CD74 HuMab antibodies were detected by flow cytometry on a FACS Canto II (BD Biosciences).

Figure 14:
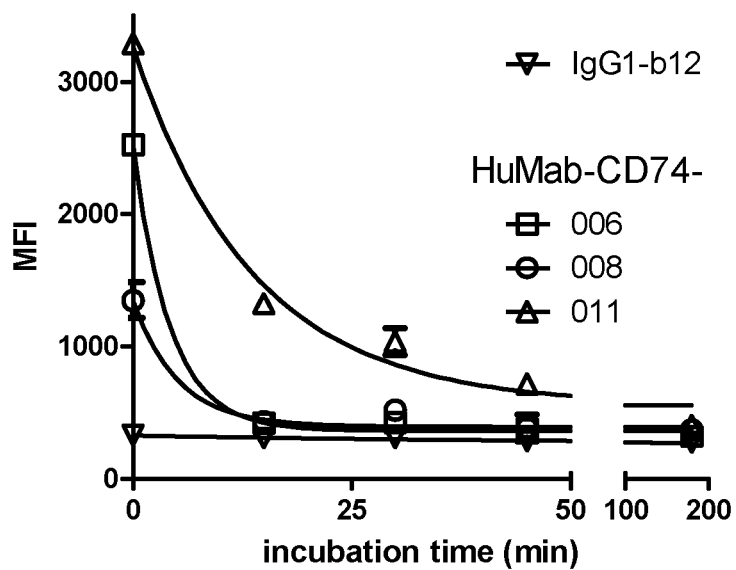
FIG. 14: Determination of off-rates of CD74-specific HuMab antibodies. One representative experiment is shown. Data shown are mean fluorescence intensities (MFI) of triplicate wells of cells incubated with Alexa Fluor 488® Dye-labeled CD74 HuMab antibodies, followed by incubation with unlabeled CD74 HuMab antibodies for the indicated time intervals.

FIG. 14 shows that off-rates of HuMab-CD74-006 and -008 measured at 0° C. were quite rapid (half of the bound Alexa-488-labeled antibodies were replaced with unlabeled antibodies within ~3 and ~4 min at 0° C., K values were 0.24 and 0.20 min$^{-1}$; [K=$k_{off}$]), whereas off-rate of -011 measured at 0° C. was a little bit slower (half of the bound Alexa 488 labeled antibodies were replaced with unlabeled antibodies within ~10 min at 0° C., K value was 0.07 min$^{-1}$).

Example 24

Internalization and Accumulation of Anti-CD74 HuMab Antibodies

To determine whether anti-CD74 HuMab antibodies are suitable for an antibody-drug conjugate approach, internalization and accumulation of antibodies was studied by FACS analysis after incubation of different anti-CD74 HuMab antibodies with Daudi cells. $10^5$ cells per well in cell culture medium were seeded in 96-well round-bottom tissue culture plates (Greiner Bio-one). 10 μg/mL (final concentration) Alexa-488-labeled anti-CD74 HuMab antibodies were added at different time points and incubated at 4° C. (to measure binding to cell surface expressed CD74) or at 37° C. (to measure binding and internalization). Total incubation time with antibody is indicated below the graphs. Internalization and accumulation at 37° C. was also tested using Raji and M4A4 cells with a final concentration of 3 μg/mL Alexa-488-labeled anti-CD74 HuMab antibodies. After incubation with antibody, cells were put on ice and plates were washed twice with FACS buffer. Cell-associated labeled antibodies were detected by flow cytometry on a FACS Canto II (BD Biosciences).

Figure 15A:
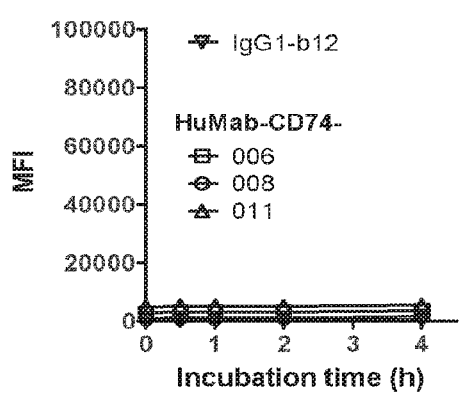
FIGS. 15A-15D: Time-dependent internalization and accumulation of anti-CD74 HuMab antibodies. One representative experiment is shown for each cell line. Data shown are mean fluorescence intensities (MFI) of duplicate wells of cells incubated with Alexa-488-labeled anti-CD74 HuMab antibodies. Daudi cells were incubated with Alexa-488-labeled anti-CD74 HuMab antibodies at 4° C.
Figure 15B:
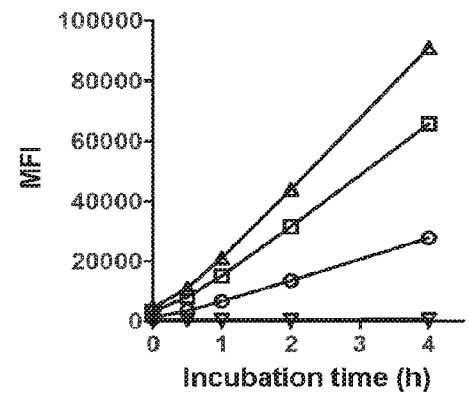
Figure 15C:
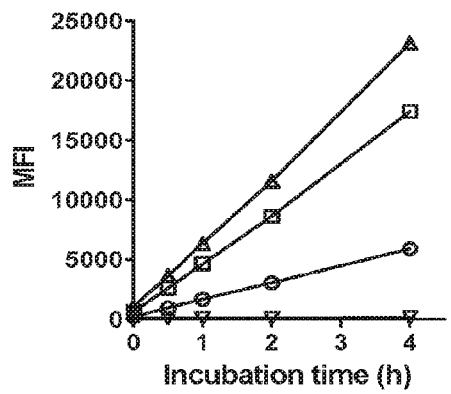
Figure 15D:
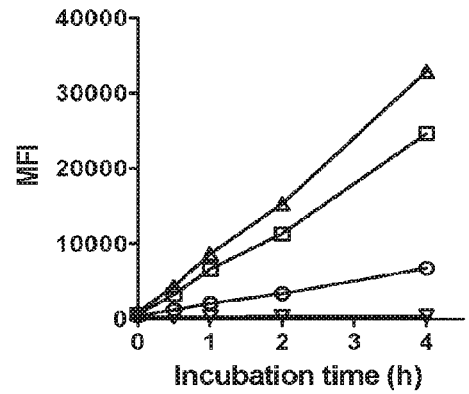

FIG. 15A shows that only low levels of binding of Alexa-488-labeled anti-CD74 HuMab antibodies to the cell surface of Daudi were detected after incubation at 4° C. at any time point. Therefore, the observed fluorescence intensities measured after incubation at 37° C. represent internalized antibody. FIG. 15B shows that all anti-CD74 HuMab antibodies tested were internalized, but with different efficacies. Internalization was most rapid for HuMab-CD74-011, slower for HuMab-CD74-006 and most slow for HuMab-CD74-008. The same was observed for internalization and accumulation in Raji cells (15C) and M4A4 cells (15D).

Example 25

Prophylactic treatment of Daudi tumor Xenografts in SCID Mice with Anti CD74 HuMab Antibodies The in vivo efficacy of anti-CD74 HuMab antibodies was determined in an intravenous (i.v.) Daudi (Burkitt's lymphoma) xenograft tumor model in SCID mice. Daudi cells were transfected by electroporation with gWIZ luciferase (Aldevron, Fargo, N. Dak., USA) and pPur vector (BD Biosciences, Alphen a/d Rijn, The Netherlands) in a 4:1 ratio. After 48 h, puromycin was added for selection of a stably transfected clone (Daudi-luc). Daudi luc #1E3 cells were cultured in RPMI supplemented with 10% cosmic calf serum (cat. no. SH30087.04, Hyclone), 1% penicillin/streptomycin (cat. no. DE17 603, Cambrex, Germany), 1% sodium pyruvate and 1 µg/mL puromycin (cat. no. P 8833, Sigma, Zwijndrecht, The Netherlands). $2.5 \times 10^6$ Daudi luc tumor cells in 100 µL PBS were injected i.v. in the tail vein of female SCID mice (7 mice per group). Mice were treated at the day of tumor inoculation with 100 µg (~5 mg/kg) HuMab-CD74-005, -006 or -011 or control antibody (IgG1b12), in 200 µL PBS, intraperitoneally (i.p.). Mice were imaged directly after tumor inoculation, followed by imaging at weekly intervals starting on day 14. For imaging, mice were anesthetized using isoflurane, followed by i.p. administration of 2.5 mg D luciferin (acid form, cat. no. BT11 1000; Biothema, Haninge, Sweden) in 200 µL 10 mg/mL TRIS (cat. no. T60666-1 kg, Sigma). Bioluminescence imaging (BLI), from the back side (dorsal view), started 10 min after administration of D luciferin, 5 min exposure time, on a Biospace Imager. Black and white images were made for anatomical reference.

Figure 16:
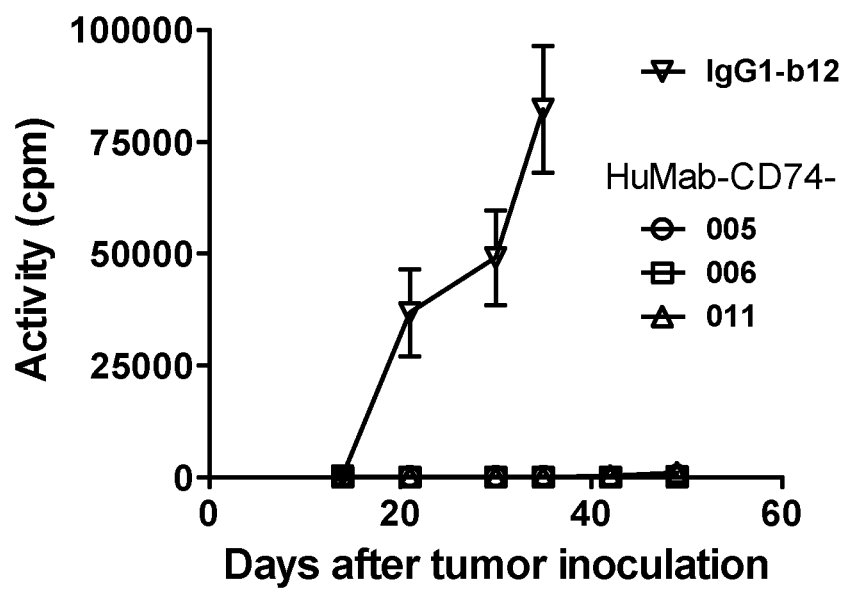
FIG. 16: In vivo efficacy of anti-CD74 HuMab antibodies in prophylactic treatment of Daudi luc xenografts in SCID mice. Mice were treated with anti CD74 HuMab antibodies within one hour after intravenous inoculation of Daudi luc tumors. Data shown are mean BLI signals±S.E.M. per group (n=7 mice per group).

FIG. 16 shows that all tested anti-CD74 HuMab antibodies almost completely prevented the outgrowth of i.v. Daudi luc tumors.

EQUIVALENTS

Those skilled in the art will recognize, or be able to ascertain using no more than routine experimentation, many equivalents of the specific embodiments of the invention described herein. Such equivalents are intended to be encompassed by the following claims. Any and all combination of embodiments disclosed in dependent claims is also contemplated to be within the scope of the invention.

The invention claimed is:

1. An antibody which binds to CD74 variants 1 and 2 and comprises a $V_L$ region comprising the CDR1, 2 and 3 sequences set forth in SEQ ID NO:24, SEQ ID NO:27, and SEQ ID NO:25, respectively, and
   a) a $V_H$ region comprising the CDR1, 2 and 3 sequences set forth in SEQ ID NO: 20, 21 and 22, respectively;
   b) a $V_H$ region comprising the CDR1, 2 and 3 sequences set forth in SEQ ID NOS:8, 9 and 10, respectively;
   c) a $V_H$ region comprising the CDR1, 2 and 3 sequences set forth in SEQ ID NO: 12, 13 and 14, respectively; or
   d) a $V_H$ region comprising the CDR1, 2 and 3 sequences set forth in SEQ ID NO: 16, 17 and 18, respectively.

2. The antibody of claim 1, which
   (a) binds to the extracellular domain of CD74 variant 1 with an $EC_{50}$ of less than about 500 ng/mL;
   (b) binds to the extracellular domain of CD74 variant 2 with an $EC_{50}$ of less than about 400 ng/mL; or
   (c) both of (a) and (b),
when determined by enzyme-linked immunosorbent assay.

3. The antibody of claim 1, which binds to CD74 on Raji cells with an $EC_{50}$ of less than about 400 ng/mL when determined by enzyme-linked immunosorbent assay.

4. The antibody of claim 1, which binds to cynomolgous CD74.

5. The antibody of claim 1, which is internalized after binding to CD74 expressed on the surface of a cell.

6. The antibody of claim 5, wherein the cell is a Raji cell.

7. The antibody of claim 1, which has an $EC_{50}$ of less than about 60 ng/mL in inducing killing of Raji cells in an anti-kappa ETA assay.

8. The antibody of claim 1, which has an off-rate at 0° C. of 0.02 to 1.0 min$^{-1}$.

9. The antibody of claim 1, which is a human monoclonal antibody.

10. The antibody of claim 1, which has an isotype selected from IgG1 and IgG4.

11. An antibody of claim 1, which is conjugated to a therapeutic moiety.

12. The antibody of claim 11, which is conjugated to the therapeutic moiety via a linker attached to sulphydryl residues in the antibody, obtained by at least partial reduction of the antibody.

13. The antibody of claim 11, wherein the therapeutic moiety is a cytotoxic moiety, a radioisotope, a chemotherapeutic agent, a lytic peptide or a cytokine.

14. The antibody of claim 13, which is conjugated to a cytotoxic moiety.

15. The antibody of claim 14, wherein the cytotoxic moiety is selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; maytansine or an analog or derivative thereof; an auristatin or a functional peptide analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite; 6 mercaptopurine; 6 thioguanine; cytarabine; fludarabin; 5 fluorouracil; decarbazine; hydroxyurea; asparaginase; gemcitabine; cladribine; an alkylating agent; a platinum derivative; duocarmycin A; duocarmycin SA; rachelmycin (CC-1065) or an analog or derivative thereof; an antibiotic; pyrrolo[2,1-c][1,4]-benzodiazepines (PDB); diphtheria toxin; ricin toxin; cholera toxin; a Shiga-like toxin; LT toxin; C3 toxin; Shiga toxin; pertussis toxin; tetanus toxin; soybean Bowman-Birk protease inhibitor; *Pseudomonas* exotoxin; alorin; saporin; modeccin; gelanin; abrin A chain; modeccin A chain; alpha-sarcin; Aleurites fordii proteins; dianthin proteins; *Phytolacca americana* proteins; *momordica charantia* inhibitor; curcin; crotin; sapaonaria officinalis inhibitor; gelonin; mitogellin; restrictocin; phenomycin; enomycin toxins; ribonuclease (RNase); DNase I; Staphylococcal enterotoxin A; pokeweed antiviral protein; diphtherin toxin; and *Pseudomonas* endotoxin.

16. The antibody of claim 14, wherein the cytotoxic moiety is selected from the group consisting of an anthracycline, a pyrrolo[2,1-c][1,4]-benzodiazepine, maytansine, calicheamicin, duocarmycin, rachelmycin (CC-1065), dolastatin 10 or 15, irinotecan, or from an analog, derivative, or prodrug of any thereof.

17. The antibody of claim 14, wherein the cytotoxic moiety is an auristatin or a functional peptide analog or derivate thereof.

18. The antibody of claim 11, which has an $IC_{50}$ of less than about 0.5 μg/mL in inducing killing of Raji, Daudi or M4A4 cells, when determined after incubating the Raji, Daudi or M4A4 cells with an anti-CD74 antibody-drug conjugate for three days and staining for viable cells with AlamarBlue.

19. The antibody of claim 13, which is conjugated to a cytokine selected from the group consisting of IL-2, IL-4, IL-6, IL-7, IL-10, IL-12, IL-13, IL-15, IL-18, IL-23, IL-24, IL-27, IL-28a, IL-28b, IL-29, KGF, IFNα, IFNβ, IFNγ, GM-CSF, CD40L, Flt3 ligand, stem cell factor, ancestim, and TNFα.

20. A recombinant eukaryotic or prokaryotic host cell which produces the antibody of claim 1.

21. A pharmaceutical composition comprising the antibody of claim 1 and a pharmaceutically acceptable carrier.

22. A method of treating cancer comprising administering to a subject in need thereof an antibody according to claim 1.

23. A method of reducing the risk of cancer progression or reducing the risk of recurrence of a cancer in remission in a subject comprising administering to the subject an antibody according to claim 1.

24. The method of claim 22, wherein the cancer is selected from the group consisting of breast cancer, colorectal cancer, endometrial/cervical cancer, gastric cancer, head and neck cancer, lung cancer, malignant glioma, malignant melanoma, ovarian cancer, pancreatic cancer, prostate cancer, renal cancer, liver cancer, thymus cancer, malignant fibrous histiosarcoma, acoustic schwannoma, pituitary adenoma, and an adenoma.

25. The method of claim 22, wherein the cancer is selected from the group consisting of malignant lymphoma, B cell chronic lymphocytic leukemia (B-CLL), chronic myeloid leukemia (CML) in blast phase, non-Hodgkin's lymphoma (NHL), multiple myeloma (MM), monocytiod B cell lymphoma (MBCL), hairy-cell leukemia (HCL), and T cell lymphoma.

26. The method of claim 25, wherein the cancer is NHL.

27. The method of claim 25, wherein the cancer is MM.

28. The method of claim 24, wherein the cancer is ovarian cancer.

29. The method of claim 24, wherein the cancer is breast cancer.

30. The method of claim 24, wherein the cancer is pancreatic cancer.

31. The method of claim 24, wherein the cancer is selected from the group consisting of prostate cancer, gastric cancer, and colorectal cancer.

32. The method of claim 22, wherein at least one further therapeutic agent is administered.

33. The method of claim 32, wherein the at least one further therapeutic agent is selected from the group consisting of a second antibody or ADC; a chemotherapeutic agent; an inhibitor of angiogenesis, neovascularization, and/or other vascularization; an anti-cancer immunogen; a cytokine or chemokine; a cell cycle control or apoptosis regulator; a hormonal regulating agent; an anti-anergic agent; a virus or viral proteins; immune system cells; a differentiation inducing agent; -IFN-γ; an anti-inflammatory, immunosuppressive and/or immunomodulatory agent; and a combination of any thereof.

34. The method of claim 33, wherein the at least one therapeutic agent is selected from the group consisting of a CD20-specific antibody, a CD138-specific antibody, a CD38-specific antibody, an anti-VEGF-A antibody, melphalanan, lenalidomide, bortezomib, fluorouracil, gemticabine, irinotecan, cisplatin, and a derivative or analog thereof.

35. A method of treating an autoimmune disease comprising administering to a subject in need thereof an antibody according to claim 1.

36. A method for inducing cell death, inhibiting growth, and/or inhibiting proliferation of a cell expressing CD74, comprising contacting the cell with the antibody of claim 1.

37. An antibody which binds to CD74 variants 1 and 2 and comprises:
(a) a $V_H$ region comprising the sequence of SEQ ID NO: 19 and a $V_L$ region comprising the sequence of SEQ ID NO: 26;
(b) a $V_H$ region comprising the sequence of SEQ ID NO: 7 and a $V_L$ region comprising the sequence of SEQ ID NO: 26;
(c) a $V_H$ region comprising the sequence of SEQ ID NO: 7 and a $V_L$ region comprising the sequence of SEQ ID NO: 23;
(d) a $V_H$ region comprising the sequence of SEQ ID NO: 11 and a $V_L$ region comprising the sequence of SEQ ID NO: 26; or
(d) a $V_H$ region comprising the sequence of SEQ ID NO: 15 and a $V_L$ region comprising the sequence of SEQ ID NO: 26.

38. An anti-idiotypic antibody against the antibody of claim 37.

39. A multispecific antibody, comprising a first antigen-binding region of an antibody selected from the group consisting of:
(a) an antibody comprising a VH region comprising the sequence of SEQ ID NO:19 and a VL region comprising the sequence of SEQ ID NO:26;
(b) an antibody comprising a VH region comprising the sequence of SEQ ID NO:7 and a VL region comprising the sequence of SEQ ID NO:23;
(c) an antibody comprising a VH region comprising the sequence of SEQ ID NO:11 and a VL region comprising the sequence of SEQ ID NO:26; and
(d) an antibody comprising a VH region comprising the sequence of SEQ ID NO:15 and a VL region comprising the sequence of SEQ ID NO:26, and
at least one second antigen-binding region having a different binding specificity.

40. The antibody of claim 39, which is a bispecific antibody.

41. The antibody of claim 39, which is a bispecific antibody wherein
the first antigen-binding region is linked to a first Fc-region having an amino acid substitution at a position selected from the group consisting of 366, 368, 370, 399, 405, 407 and 409, and the second antigen-binding region is linked to a second Fc-region having an amino acid substitution at a position selected from the group consisting of 366, 368, 370, 399, 405, 407 and 409, and
the first and second Fc-regions are not substituted in the same positions.

42. An expression vector comprising a nucleotide sequence encoding one or more of the amino acid sequences selected from the group consisting of SEQ ID NOs: 7, 11, 15, 19, and 23, or any combination thereof.

43. An expression vector according to claim 42, further comprising a nucleotide sequence encoding the constant region of a human antibody light chain, of a human antibody heavy chain, or both.

* * * * *